US009228225B2

(12) United States Patent
Reddington et al.

(10) Patent No.: US 9,228,225 B2
(45) Date of Patent: *Jan. 5, 2016

(54) XANTHENE DYES

(75) Inventors: Mark Reddington, San Francisco, CA (US); Matt Lyttle, San Rafael, CA (US)

(73) Assignee: BIOSEARCH TECHNOLOGIES, INC., Petaluma, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/941,931

(22) Filed: Nov. 8, 2010

(65) Prior Publication Data

US 2011/0054165 A1   Mar. 3, 2011

Related U.S. Application Data

(63) Continuation of application No. 12/036,926, filed on Feb. 25, 2008, now abandoned, which is a continuation of application No. 10/824,175, filed on Apr. 13, 2004, now Pat. No. 7,344,701.

(60) Provisional application No. 60/541,686, filed on Feb. 3, 2004.

(51) Int. Cl.
| | |
|---|---|
| A61B 10/00 | (2006.01) |
| A61B 8/00 | (2006.01) |
| A61B 5/00 | (2006.01) |
| C12Q 1/37 | (2006.01) |
| C07D 311/90 | (2006.01) |
| C07D 405/14 | (2006.01) |
| C07F 9/655 | (2006.01) |
| C07F 9/6558 | (2006.01) |
| G01N 33/58 | (2006.01) |

(52) U.S. Cl.
CPC ............... *C12Q 1/37* (2013.01); *C07D 311/90* (2013.01); *C07D 405/14* (2013.01); *C07F 9/65522* (2013.01); *C07F 9/65586* (2013.01); *G01N 33/582* (2013.01)

(58) Field of Classification Search
CPC ........... A61K 49/0032; A61K 49/0056; A61K 49/0021; A61K 41/0057; A61K 41/0033; C07D 311/86; C07D 311/00; C07D 311/02; C07D 311/82; C07D 311/84; C07D 311/90; C07D 405/14; C12Q 1/37; C07F 9/65522; C07F 9/65586; G01N 33/582
USPC ............ 424/1.11, 1.49, 1.65, 1.69, 1.73, 9.1, 424/9.6, 9.2; 549/200, 223, 224, 225, 356, 549/220, 226, 227, 388, 394; 536/28.52; 435/6.12, 7.1; 534/551; 544/317, 361; 546/16, 23, 25; 548/525
See application file for complete search history.

(56) References Cited

U.S. PATENT DOCUMENTS

| | | | | |
|---|---|---|---|---|
| 3,939,350 | A * | 2/1976 | Kronick et al. | 250/365 |
| 4,290,955 | A | 9/1981 | Cincotta et al. | |
| 4,329,461 | A | 5/1982 | Khanna et al. | |
| 4,647,675 | A | 3/1987 | Mayer et al. | |
| 4,900,686 | A | 2/1990 | Arnost et al. | |
| 4,935,059 | A | 6/1990 | Mayer et al. | |
| 5,538,848 | A * | 7/1996 | Livak et al. | 435/6.16 |
| 5,610,151 | A * | 3/1997 | Glombik et al. | 514/172 |
| 5,723,591 | A * | 3/1998 | Livak et al. | 536/22.1 |
| 5,814,297 | A * | 9/1998 | Dean et al. | 424/1.69 |
| 6,080,852 | A | 6/2000 | Lee et al. | |
| 6,399,392 | B1 | 6/2002 | Haugland et al. | |
| 6,552,007 | B2 * | 4/2003 | Chen et al. | 514/100 |
| 6,750,003 | B2 | 6/2004 | Takizawa | |
| 6,750,357 | B1 | 6/2004 | Chiarello et al. | |
| 7,183,405 | B2 | 2/2007 | Chiarello et al. | |
| 7,344,701 | B2 * | 3/2008 | Reddington et al. | 424/1.73 |
| 2004/0054195 | A1 * | 3/2004 | Gao et al. | 549/223 |

FOREIGN PATENT DOCUMENTS

| | | |
|---|---|---|
| EP | 0805190 A | 11/1997 |
| WO | 97/39064 A1 | 10/1997 |
| WO | WO 9736064 A | 10/1997 |
| WO | WO 0064988 A | 11/2000 |
| WO | 02/055512 A1 | 7/2002 |
| WO | WO 02005512 A | 7/2002 |
| WO | WO 03002715 | 1/2003 |
| WO | WO 03028724 A | 4/2003 |
| WO | WO 2004055117 A2 | 7/2004 |
| WO | WO 2005085470 A | 9/2005 |

OTHER PUBLICATIONS

Adamczyk, Maciej, et al., "Efficient Florescein Spriolactam and Bis-Spirolactam Synthesis," Synthetic Communications, 2001, vol. 31, No. 17; pp. 2681-2690.

Crespo, L. et al., "Peptide Dendrimers based on Polyproline Helices", 2002, J. Am. Chem. Soc. vol. 124, pp. 8876-8883.

Slais, K., et al., :Fluorescein-based p/markers for capillary isoelectric focusing with lase-induced fluorescence detection, Electrophoresis, 2002, vol. 23, pp. 1682-1688.

Walton, Troy A., et al., "Evaluation of New Linkers and Synthetic Methods for Internal Modified Oligonucleotides," Bioconjugate Chemistry, 2002, vol. 13, pp. 1155-1158.

* cited by examiner

*Primary Examiner* — D L Jones
(74) *Attorney, Agent, or Firm* — Morgan, Lewis & Bockius LLP; Jeffry S. Mann

(57) ABSTRACT

The invention provides a novel class of xanthene dyes, some of which are functionalized to allow their coupling to conjugation partners of interest, e.g. biomolecules, drugs, toxins and the like. Also provided are conjugates of the dyes, methods of preparing and using the dyes and their conjugates and kits including the dyes and their conjugates.

37 Claims, 17 Drawing Sheets

FIG. 1A

| Parent Xanthene Dye | DNA Synthesis Reagent |
|---|---|
| Rhodamine B | |
| | |
| | |
| Rhodamine 6G | |

SEQUENCE LISTING

<160> NUMBER OF SEQ ID NOS: 9

<210> SEQ ID NO 1
<211> LENGTH: 14
<212> TYPE: DNA
<213> ORGANISM: Artificial
<220> FEATURE:
<223> OTHER INFORMATION: synthetic DNA fragment

<400> SEQUENCE: 1
gatctgaata gctt                                                    14

<210> SEQ ID NO 2
<211> LENGTH: 10
<212> TYPE: DNA
<213> ORGANISM: Artificial
<220> FEATURE:
<223> OTHER INFORMATION: synthetic DNA fragment

<400> SEQUENCE: 2

```
tttttttttt                                                              10

<210> SEQ ID NO 3
<211> LENGTH: 15
<212> TYPE: DNA
<213> ORGANISM: Artificial
<220> FEATURE:
<223> OTHER INFORMATION: synthetic DNA fragment

<400> SEQUENCE: 3
tttttttttt ttttt                                                        15

<210> SEQ ID NO 4
<211> LENGTH: 19
<212> TYPE: DNA
<213> ORGANISM: Artificial
<220> FEATURE:
<223> OTHER INFORMATION: human Telomerase Reverse Transcriptase

<400> SEQUENCE: 4
caggtggaga ccctgagaa                                                    19

<210> SEQ ID NO 5
<211> LENGTH: 21
<212> TYPE: DNA
<213> ORGANISM: Artificial
<220> FEATURE:
<223> OTHER INFORMATION: human Telomerase Reverse Transcriptase

<400> SEQUENCE: 5
acacctttgg tcactccaaa t                                                 21

<210> SEQ ID NO 6
<211> LENGTH: 20
<212> TYPE: DNA
<213> ORGANISM: Artificial
<220> FEATURE:
<223> OTHER INFORMATION: human Telomerase Reverse Transcriptase

<400> SEQUENCE: 6
tcccagagct cccagggtcc                                                   20

<210> SEQ ID NO 7
<211> LENGTH: 23
<212> TYPE: DNA
<213> ORGANISM: Artificial
<220> FEATURE:
<223> OTHER INFORMATION: human Apolipoprotein B

<400> SEQUENCE: 7
tgaaggtgga ggacattcct cta                                               23

<210> SEQ ID NO 8
<211> LENGTH: 22
<212> TYPE: DNA
<213> ORGANISM: Artificial
<220> FEATURE:
<223> OTHER INFORMATION: human Apolipoprotein B

<400> SEQUENCE: 8
ctggaattgc gatttctggt aa                                                22

<210> SEQ ID NO 9
<211> LENGTH: 26
<212> TYPE: DNA
<213> ORGANISM: Artificial
```

```
<220> FEATURE:
<223> OTHER INFORMATION: human Apolipoprotein B
<400> SEQUENCE: 9
cgagaatcac cctgccagac ttccgt                                              26
```

XANTHENE DYES

CROSS-REFERENCE TO RELATED APPLICATIONS

This application is a continuation of U.S. patent application Ser. No. 12/036,926, now abandoned, filed on Feb. 25, 2008, which is a continuation of U.S. patent application Ser. No. 10/824,175, filed on Apr. 13, 2004, issued as U.S. Pat. No. 7,344,701, which claims priority under 35 U.S.C. §119(e) to U.S. Provisional Patent Application No. 60/541,686, filed on Feb. 3, 2004, the disclosures of which are incorporated by reference herein in their entirety for an purposes.

REFERENCE TO SEQUENCE LISTING SUBMITTED ELECTRONICALLY

The sequence listing contained in the file named "5011US2SequenceListing.txt", created on Nov. 8, 2010 and having a size of 2 kilobytes, has been submitted electronically herewith via EFS-Web, and the contents of the txt file are hereby incorporated by reference in their entirety.

FIELD OF INVENTION

The present invention relates generally to the synthesis of fluorescent compounds that are analogues of xanthene dyes. The compounds of the invention are fluorophores that are derivatized to allow their facile attachment to a carrier molecule.

BACKGROUND

There is a continuous and expanding need for rapid, highly specific methods of detecting and quantifying chemical, biochemical and biological substances as analytes in research and diagnostic mixtures. Of particular value are methods for measuring small quantities of nucleic acids, peptides, saccharides, pharmaceuticals, metabolites, microorganisms and other materials of diagnostic value. Examples of such materials include narcotics and poisons, drugs administered for therapeutic purposes, hormones, pathogenic microorganisms and viruses, peptides, e.g., antibodies and enzymes, and nucleic acids, particularly those implicated in disease states.

The presence of a particular analyte can often be determined by binding methods that exploit the high degree of specificity that characterizes many biochemical and biological systems. Frequently used methods are based on, for example, antigen-antibody systems, nucleic acid hybridization techniques and protein-ligand systems. In these methods, the existence of a complex of diagnostic value is typically indicated by the presence or absence of an observable "label" which is attached to one or more of the interacting materials. The specific labeling method chosen often dictates the usefulness and versatility of a particular system for detecting an analyte of interest. Preferred labels are inexpensive, safe, and capable of being attached efficiently to a wide variety of chemical, biochemical, and biological materials without significantly altering the important binding characteristics of those materials. The label should give a highly characteristic signal, and should be rarely, and preferably never, found in nature. The label should be stable and detectable in aqueous systems over periods of time ranging up to months. Detection of the label is preferably rapid, sensitive, and reproducible without the need for expensive, specialized facilities or the need for special precautions to protect personnel. Quantification of the label is preferably relatively independent of variables such as temperature and the composition of the mixture to be assayed.

A wide variety of labels have been developed, each with particular advantages and disadvantages. For example, radioactive labels are quite versatile, and can be detected at very low concentrations, such labels are, however, expensive, hazardous, and their use requires sophisticated equipment and trained personnel. Thus, there is wide interest in non-radioactive labels, particularly in labels that are observable by spectrophotometric, spin resonance and luminescence techniques, and reactive materials, such as enzymes that produce such molecules.

Labels that are detectable using fluorescence spectroscopy are of particular interest, because of the large number of such labels that are known in the art. Moreover, as discussed below, the literature is replete with syntheses of fluorescent labels that are derivatized to allow their attachment to other molecules and many such fluorescent labels are commercially available.

In addition to being directly detected, many fluorescent labels operate to quench the fluorescence of an adjacent second fluorescent label. Because of its dependence on the distance and the magnitude of the interaction between the quencher and the fluorophore, the quenching of a fluorescent species provides a sensitive probe of molecular conformation and binding, as well as or other interactions. An excellent example of the use of fluorescent reporter quencher pairs is found in the detection and analysis of nucleic acids.

Fluorescent nucleic acid probes are important tools for genetic analysis, in both genomic research and development, and in clinical medicine. As information from the Human Genome Project accumulates, the level of genetic interrogation mediated by fluorescent probes will expand enormously. One particularly useful class of fluorescent probes includes self-quenching probes, also known as fluorescence energy transfer probes, or FET probes. The design of different probes using this motif may vary in detail. In an exemplary FET probe, both a fluorophore and a quencher are tethered to a nucleic acid. The probe is configured such that the fluorophore is proximate to the quencher and the probe produces a signal only as a result of its hybridization to an intended target. Despite the limited availability of FET probes, techniques incorporating their use are rapidly displacing alternative methods.

Probes containing a fluorophore-quencher pair have been developed for nucleic acid hybridization assays where the probe forms a hairpin structure, i.e., where the probe hybridizes to itself to form a loop such that the quencher molecule is brought into proximity with the reporter molecule in the absence of a complementary nucleic acid sequence to prevent the formation of the hairpin structure (see, for example, WO 90/03446; European Patent Application No. 0 601 889 A2). When a complementary target sequence is present, hybridization of the probe to the complementary target sequence disrupts the hairpin structure and causes the probe to adopt a conformation where the quencher molecule is no longer close enough to the reporter molecule to quench the reporter molecule. As a result, the probes provide an increased fluorescence signal when hybridized to a target sequence than when they are unhybridized.

Assays have also been developed for detecting a selected nucleic acid sequence and for identifying the presence of a hairpin structure using two separate probes, one containing a reporter molecule and the other a quencher molecule (see, Meringue, et al., *Nucleic Acids Research*, 22: 920-928 (1994)). In these assays, the fluorescence signal of the reporter molecule decreases when hybridized to the target sequence due to the quencher molecule being brought into proximity with the reporter molecule.

One particularly important application for probes including a reporter—quencher molecule pair is their use in nucleic acid amplification reactions, such as polymerase chain reactions (PCR), to detect the presence and amplification of a target nucleic acid sequence. In general, nucleic acid amplification techniques have opened broad new approaches to genetic testing and DNA analysis (see, for example, Arnheim et al. *Ann. Rev. Biochem.*, 61: 131-156 (1992)). PCR, in particular, has become a research tool of major importance with applications in, for example, cloning, analysis of genetic expression, DNA sequencing, genetic mapping and drug discovery (see, Arnheim et al., supra; Gilliland et al., *Proc. Natl. Acad. Sci. USA,* 87: 2725-2729 (1990); Bevan et al., *PCR Methods and Applications,* 1: 222-228 (1992); Green et al., *PCR Methods and Applications,* 1: 77-90 (1991); Blackwell et al., *Science,* 250: 1104-1110 (1990)).

Commonly used methods for detecting nucleic acid amplification products require that the amplified product be separated from unreacted primers. This is typically achieved either through the use of gel electrophoresis, which separates the amplification product from the primers on the basis of a size differential, or through the immobilization of the product, allowing free primer to be washed away. However, a number of methods for monitoring the amplification process without prior separation of primer have been described; all of them are based on FET, and none of them detect the amplified product directly. Instead, the methods detect some event related to amplification. For that reason, they are accompanied by problems of high background, and are not quantitative, as discussed below.

One method, described in Wang et al. (U.S. Pat. No. 5,348, 853; and *Anal. Chem.,* 67: 1197-1203 (1995)), uses an energy transfer system in which energy transfer occurs between two fluorophores on the probe. In this method, detection of the amplified molecule takes place in the amplification reaction vessel, without the need for a separation step.

A second method for detecting an amplification product without prior separation of primer and product is the 5'-nuclease PCR assay (also referred to as the TaqMan™ assay) (Holland et al., *Proc. Natl. Acad. Sci. USA,* 88: 7276-7280 (1991); Lee et al., *Nucleic Acids Res.,* 21: 3761-3766 (1993)). This assay detects the accumulation of a specific PCR product by hybridization and cleavage of a doubly labeled fluorogenic probe (the "TaqMan" probe) during the amplification reaction. The fluorogenic probe consists of a nucleic acid labeled with both a fluorescent reporter dye and a quencher dye. During PCR, this probe is cleaved by the 5'-exonuclease activity of DNA polymerase if, and only if, it hybridizes to the segment being amplified. Cleavage of the probe generates an increase in the fluorescence intensity of the reporter dye.

Yet another method of detecting amplification products that relies on the use of energy transfer is the "beacon probe" method described by Tyagi et al. (*Nature Biotech.,* 14: 303-309 (1996)) which is also the subject of U.S. Pat. No. 5,312, 728 to Lizardi et al. This method employs nucleic acid hybridization probes that can form hairpin structures. On one end of the hybridization probe (either the 5'- or 3'-end) there is a donor fluorophore, and on the other end, an acceptor moiety. In this method, the acceptor moiety is a quencher, absorbing energy from the donor. Thus when the beacon is in the open conformation, the fluorescence of the donor fluorophore is detectable, whereas when the beacon is in hairpin (closed) conformation, the fluorescence of the donor fluorophore is quenched. When employed in PCR, the molecular beacon probe, which hybridizes to one of the strands of the PCR product, is in "open conformation," and fluorescence is detected, while those that remain unhybridized will not fluoresce. As a result, the amount of fluorescence will increase as the amount of PCR product increases, and thus can be used as a measure of the progress of the PCR.

The probes discussed above are most generally configured such that the quencher and fluorophore are on the 3'- and 5'-ends of the probe (Lyamichev et al., *Science,* 260:778-783 (1993)). This spacing of the fluorophore and quencher may impede fluorescent energy transfer: fluorescence energy transfer decreases as the inverse sixth power of the distance between the fluorophore and quencher. Thus, if the quencher is not close enough to the reporter to achieve efficient quenching the background emissions from the probe can be quite high.

For the xanthene dye to be useful as a label it must posses a chemical functional group the will permit it to bind to, or react with, a substrate of interest. The incorporation of such reactive chemical functionality into xanthene dyes usually requires additional synthetic steps and/or difficult to implement purification methods. In particular, separation of structural isomers of fluoresceins and rhodamines, which are the most commonly used xanthene labeling reagents for biological and medical applications, is tedious and is to be avoided if possible.

The core chemical structure of many fluorescein and rhodamine dyes includes a carboxylic acid group in the ortho position of the benzene ring attached to the xanthene residue; some others posses a sulfonic acid group at this site. The carboxylic acid group has not been widely utilized as a site for conjugation of the dye to substrates due to its low reactivity and due to side reactions that render the dye non-fluorescent. Although the carboxylic acid can be activated and reacted with alcohols to form esters or with amines to form amides, the ester linkage is of insufficient stability to be useful when preparing compounds that are stably labeled with a fluorophore.

The amide linkage is stable to hydrolysis but while some amides prepared from the activated carboxylic acid and primary amines are reported to be colored (Mayer et al., U.S. Pat. No. 4,647,675) others are reported to undergo a spirolactamization reaction in which the dye loses its color and is rendered non-fluorescent (Adamczyk et al., *Synthetic Commun.* 31: 2681-2690 (2001); and Cincotta et al., U.S. Pat. No. 4,290,955)). In contrast, secondary amines react with the activated carboxylic acid to create an amide link that cannot undergo spirolactamization, providing a xanthene dye that retains its color and fluorescence (Gao et al., WO 02/055512). Menchen et al. disclose xanthene dyes in which the ortho carboxyl moiety is activated and coupled to another species. Other amide derivatized xanthene dyes are disclosed in Haugland et al., U.S. Pat. No. 6,399,392; and Mayer et al., U.S. Pat. No. 4,935,059.

Xanthene dyes that posses a sulfonic acid group in the ortho position can be activated and reacted with alcohols and with amines in a manner similar to xanthene dyes with ortho carboxylic acid groups to yield sulfonate esters and sulfonamides, respectively. The sulfonate esters are not stable under aqueous conditions and are of little use as linker functionality for preparing oligonucleotides. The sulfonamides are stable and have been used to prepare reactive xanthene dyes such as succinimidyl esters, maleimides and phosphoramidites.

None of the above-described references discloses or suggests the modification of the fluorophore nucleus with a versatile amide-linked moiety that allows for the facile variation of the composition, length and degree of branching of the linker. Furthermore, none of the references suggest a linker that provides a locus for attaching the fluorophore to a solid support, nor do the references describe a branched linker moiety that tethers both a phosphoramidite and a dimethoxytrityl ether to a single endocyclic nitrogen atom.

Attaching quenchers or fluorophores to sites other than the readily accessible 5'-OH group generally requires the synthesis of fluorescent labels that are of use to attach the fluorophore to a single reactive residue of a carrier molecule or a selected reactive functional group on that residue; reacting the same fluorophore with a different functional group of the carrier generally requires a new modification of the fluorescent core. Similarly, modifying the structure or composition of the linker arm requires a modification to the fluorophore nucleus. Thus, a xanthene label that provides a versatile entry point for an array of synthetic modifications would represent a significant advance in the art.

BRIEF SUMMARY OF THE INVENTION

The inventors have prepared a class of xanthene-based fluorophores modified with a versatile linker arm, the structure of which is readily alterable, allowing the conjugation of the label to a variety of positions, through diverse functional groups, on a carrier molecule. The xanthene-based labels are readily attached to a carrier molecule using techniques well known in the art, or modifications of such techniques that are well within the abilities of those of skill in the art. The versatility of the labels set forth herein provides a marked advantage over currently utilized xanthene labels, probes assembled using these labels and methods relying upon such labels and probes. Moreover, the present invention provides a class of chemically versatile labels in which the fluorophore can be engineered to have a desired light emission profile.

In an exemplary embodiment, the fluorescent nucleus is functionalized through the ortho carboxylic acid group of the phenyl moiety attached to the xanthene nucleus, requiring fewer chemical synthesis steps and eliminating the need to separate structural isomers. Additionally, many xanthene dyes possessing the ortho carboxy functional group are commercially available at low cost for use as starting materials.

Thus, in a first aspect, the present invention provides a fluorescent compound having the formula:

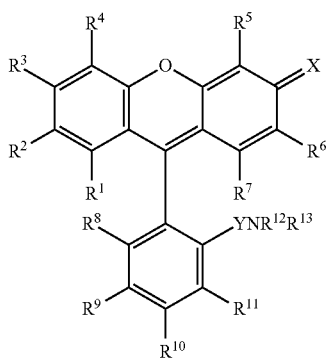

in which $R^1$, $R^2$ and $R^4$-$R^{11}$ are each independently selected from groups such as substituted or unsubstituted alkyl, substituted or unsubstituted heteroalkyl, substituted or unsubstituted aryl, substituted or unsubstituted heteroaryl, substituted or unsubstituted heterocycloalkyl, halogen, H, $NO_2$, CN and $C(Z^1)R^{14}$, $NR^{15}R^{16}$ and $Z^2R^{16}$. $R^3$ is selected from $Z^2R^{16}$ and $NR^{15}R^{16}$.

$Z^1$ represents O, S or NH. $Z^2$ is either O or S. Groups corresponding to $R^{15}$ include H, substituted or unsubstituted alkyl, and substituted or unsubstituted heteroalkyl. $R^{16}$ is selected from H, substituted or unsubstituted alkyl and substituted or unsubstituted heteroalkyl and $C(Z^3)R^{17}$. $R^{15}$ and $R^{16}$, together with the nitrogen to which they are attached, can also be any nitrogen-containing reactive group. Exemplary groups include —$NHNH_2$, —N=C=S and —N=C=O.

$Z^3$ represents O, S or NH. The symbol $R^{17}$ represents groups such as substituted or unsubstituted alkyl, substituted or unsubstituted heteroalkyl, $OR^{18}$, and $NR^{19}R^{20}$. $R^{18}$ represents H, substituted or unsubstituted alkyl, substituted or unsubstituted heteroalkyl, substituted or unsubstituted aryl, substituted or unsubstituted heteroaryl and $C(O)R^{21}$. $R^{19}$ and $R^{20}$ are symbols representing groups independently selected from H, substituted or unsubstituted alkyl and substituted or unsubstituted heteroalkyl. $R^{21}$ is substituted or unsubstituted alkyl or substituted or unsubstituted heteroalkyl.

The symbol Y represents either C(O) or $S(O)_2$. X is $(NR^{22}R^{23})$ or (O). $R^{22}$ and $R^{23}$ are independently selected and are members selected from H, substituted or unsubstituted alkyl and substituted or unsubstituted heteroalkyl.

$R^{12}$ or $R^{13}$ are independently selected from substituted or unsubstituted alkyl, substituted or unsubstituted heteroalkyl, substituted or unsubstituted heterocycloalkyl, substituted or unsubstituted aryl and substituted or unsubstituted heteroaryl, with the proviso that at least one of $R^{12}$ or $R^{13}$ comprises an oxygen-containing reactive group a carrier molecule or solid support to which the dye of the invention is conjugated through a moiety produced by reaction of the oxygen-containing reactive group with a reactive group on the carrier molecule of complementary reactivity. $R^{12}$ and $R^{13}$, together with the nitrogen atom to which they are attached are optionally joined to form a ring. Exemplary rings include 4-6-membered heterocylic and heteroaryl rings. When $R^{12}$ and $R^{13}$, together with the nitrogen to which they are attached form a piperazine ring in which the second nitrogen atom is functionalized with an alkyl moiety bearing an oxygen-containing reactive group, the reactive group is preferably a phosphoramidite.

The bond formed between through the reactive oxygen-containing functional group and the group of complementary reactivity is, for example, a bond to a carrier molecule, a bond to a linker bound to a carrier molecule, a bond to a solid support, a bond to a linker bound to a solid support, a bond to a fluorescence quencher, and a bond to a linker bound to a fluorescence quencher.

The substituents on the aryl ring nuclei can be joined to form rings. For example, in one embodiment in which $R^3$ is $NR^{15}R^{16}$, $R^2$, $R^4$ and $R^{15}$ and $R^{16}$, together with the nitrogen atom to which they are bound, are fused with the phenyl moiety to which $NR^{15}R^{16}$, $R^2$ and $R^4$ are bound, forming a substituted or unsubstituted ring system having the general formula:

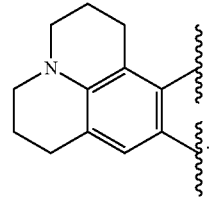

In yet another embodiment in which X is $NR^{22}R^{23}$, $R^5$, $R^6$ and $R^{22}$ and $R^{23}$, together with the nitrogen atom to which they are bound, are fused with the unsaturated 6-member ring to which NR$^{22}$R$^{23}$, R$^5$ and R$^6$ are bound, forming a substituted or unsubstituted ring system having the general formula:

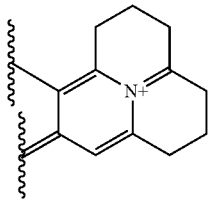

The present invention also provides a conjugate between a carrier molecule, e.g., a nucleic acid, and a fluorescent compound of the invention, which is covalently or ionically bound to a moiety of the carrier molecule. When the carrier molecule is a nucleic acid, representative moieties at which the fluorescent compounds of the invention are attached include the sugar moiety, at O- and/or C-centers; endo- and/or exo-cyclic amines, carbon atoms of nucleobase moieties, and internucleotide bridges. In still a further exemplary embodiment, the conjugate between the compound of the invention and the carrier molecule includes at least one moiety that quenches the fluorescence emission of the compound of the invention.

Also provided are assays utilizing one or more compound of the invention or a conjugate between a compound of the invention and a carrier molecule. In exemplary assays the carrier molecule includes both a dye of the invention and a species that quenches fluorescence emission from the dye.

Other aspects, embodiments and objects of the present invention will be apparent from the detailed description that follows.

BRIEF DESCRIPTION OF THE DRAWINGS

FIGS. 1A and 1B displays representative compounds of the invention.

DETAILED DESCRIPTION OF THE INVENTION

Abbreviations

Figure 1B:
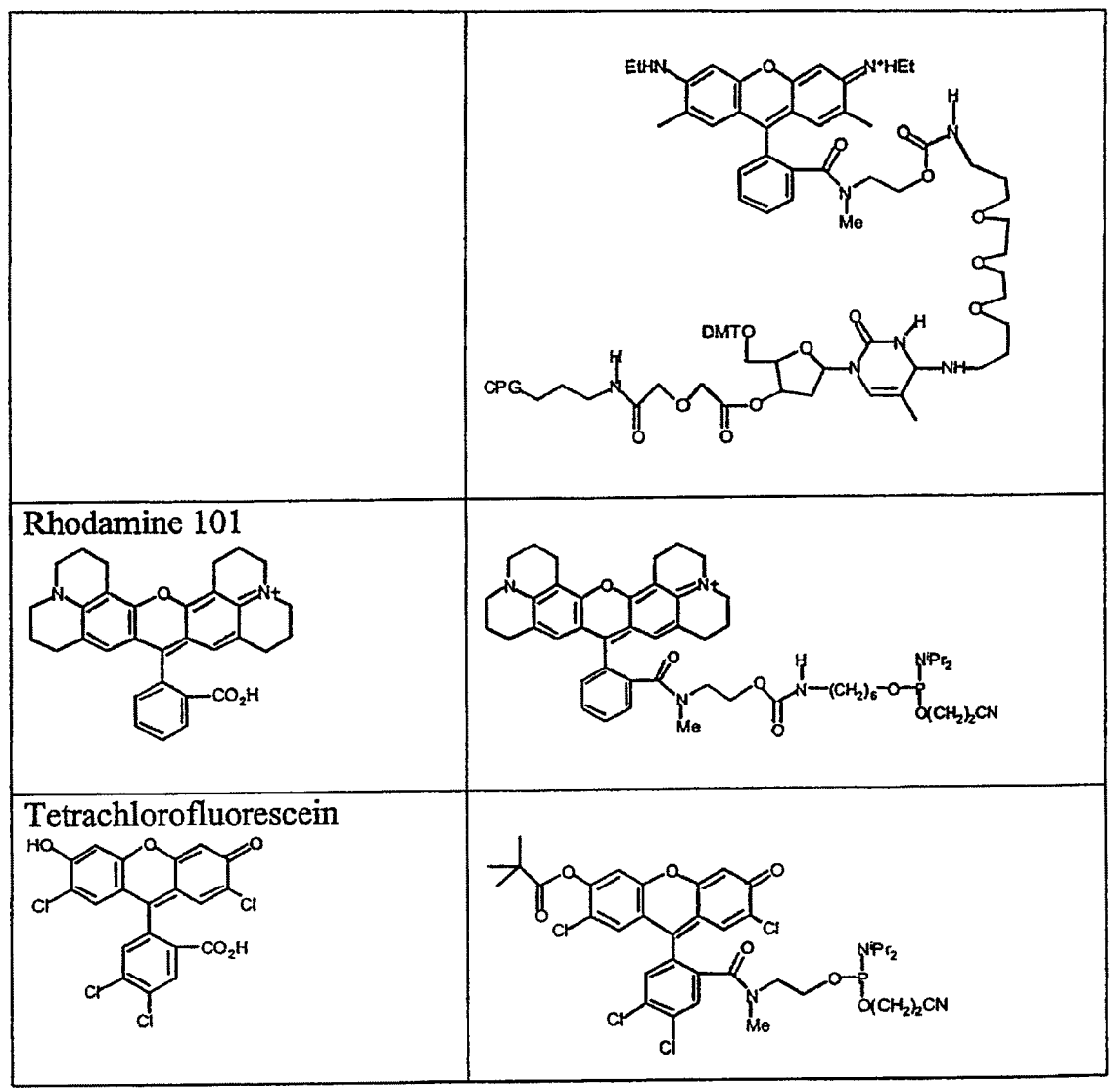

"FET," as used herein, refers to "Fluorescence Energy Transfer."

"FRET," as used herein, refers to "Fluorescence Resonance Energy Transfer." These terms are used herein to refer to both radiative and non-radiative energy transfer processes. For example, processes in which a photon is emitted and those involving long-range electron transfer are included within these terms. Throughout this specification, both of these phenomena are subsumed under the general term "donor-acceptor energy transfer."

Definitions

Where chemical moieties are specified by their conventional chemical formulae, written from left to right, they equally encompass the moiety which would result from writing the structure from right to left, e.g., —CH$_2$O— is intended to also recite —OCH$_2$—; —NHS(O)$_2$— is also intended to represent —S(O)$_2$HN—, etc.

As used herein, "nucleic acid" means any natural or non-natural nucleoside, or nucleotide and oligomers and polymers thereof, e.g., DNA, RNA, single-stranded, double-stranded, triple-stranded or more highly aggregated hybridization motifs, and any chemical modifications thereof. Modifications include, but are not limited to, conjugation with a compound of the invention or a construct that includes a compound of the invention covalently attached to a linker that tethers the compound to the nucleic acid, and those providing the nucleic acid with a group that incorporates additional charge, polarizability, hydrogen bonding, electrostatic interaction, fluxionality or functionality to the nucleic acid. Exemplary modifications include the attachment to the nucleic acid, at any position, of one or more hydrophobic or hydrophilic moieties, minor groove binders, intercalating agents, quenchers, chelating agents, metal chelates, solid supports, and other groups that are usefully attached to nucleic acids.

Exemplary modified nucleic acids include, but are not limited to, peptide nucleic acids (PNAs), those with phosphodiester group modifications (e.g., replacement of O$^-$ with OR, NR, or SR), 2'-, 3'- and 5'-position sugar modifications, modifications to the base moiety, e.g., 5-position pyrimidine modifications, 8-position purine modifications, modifications at exocyclic amines, substitution of 4-thiouridine, substitution of 5-bromo or 5-iodo-uracil; backbone modifications, i.e., substitution of P(O)O$_3$ with another moiety, methylations, unusual base-pairing combinations such as the isobases, iso-cytidine and isoguanidine and the like. Nucleic acids can also include non-natural bases, e.g., nitroindole. Non-natural bases include bases that are modified with a compound of the invention or a linker-compound of the invention construct, a minor groove binder, an intercalating agent, a hybridization enhancer, a chelating agent, a metal chelate, a quencher, a fluorophore, a fluorogenic compound, etc. Modifications within the scope of "nucleic acid" also include 3' and 5' modifications with one or more of the species described above.

"Nucleic acid" also includes species that are modified at one or more internucleotide bridge (e.g., P(O)O$_3$) by replacing or derivatizing an oxygen of the bridge atom with a compound of the invention or a species that includes a compound of the invention attached to a linker. For example, "nucleic acid" also refers to species in which the P(O)O$_2$ moiety (the O$^-$ moiety remains unchanged or is converted to "OR") of a natural nucleic acid is replaced with a non-natural linker species, e.g., —ORP(O)O—, —ROP(O)R—, —ORP(O)OR— —ROP(O)OR— or —RP(O)R— in which the symbol "-" indicates the position of attachment of the linker to the 2'-, 3'- or 5'-carbon of a nucleotide sugar moiety, thus allowing the placement of the exemplified, and other, non-natural linkers between adjacent nucleoside sugar moieties. Exemplary linker subunits ("R") include substituted or unsubstituted alkyl and substituted or unsubstituted heteroalkyl moieties. "R" can include a compound of the invention or a construct of a linker and a compound of the invention.

Furthermore, "nucleic acid" includes those species in which one or more internucleotide bridge does not include phosphorus: the bridge being optionally modified with a compound of the invention or a linker arm-xanthene dye construct. An exemplary bridge includes a substituted or unsubstituted alkyl or substituted or unsubstituted heteroalkyl moiety in which a carbon atom is the locus for the interconnection of two nucleoside sugar residues (or linker moieties attached thereto) and a compound of the invention or a linker construct that includes a compound of the invention. The discussion above is not limited to moieties that include a carbon atom as the point of attachment; the locus can also be another appropriate linking atom, such as nitrogen or another atom.

Those of skill in the art will understand that in each of the "nucleic acid" compounds described above, the structure corresponding to the term "compound of the invention" can be interchanged with a quencher, a hybridization enhancer, and intercalator, a minor groove binder, a chelating agent, a metal chelate or other moiety that is usefully conjugated to a nucleic acid, optionally being present in tandem with species that include a compound of the invention or a derivative thereof.

As used herein, "quenching group" refers to any fluorescence-modifying group of the invention that can attenuate at least partly the light emitted by a fluorescent group. This attenuation is referred to herein as "quenching". Hence, illumination of the fluorescent group in the presence of the quenching group leads to an emission signal that is less intense than expected, or even completely absent. Quenching typically occurs through energy transfer between the fluorescent group and the quenching group.

"Peptide" refers to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. Commonly encountered amino acids that are not gene-encoded may also be used in the present invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

"Bioactive species," refers to molecules that, when administered to an organism, affect that organism. Exemplary bioactive species include pharmaceuticals, pesticides, herbicides, growth regulators and the like. Bioactive species encompasses small molecules (i.e., approximately <1000 daltons), oligomers, polymers and the like. Also included are nucleic acids and their analogues, peptides and their analogues and the like.

"Carrier molecule," as used herein refers to any molecule to which a compound of the invention is attached. Representative carrier molecules include a protein (e.g., enzyme, antibody), glycoprotein, peptide, saccharide (e.g., mono-oliogo- and poly-saccharides), hormone, receptor, antigen, substrate, metabolite, transition state analog, cofactor, inhibitor, drug, dye, nutrient, growth factor, etc., without limitation. "Carrier molecule" also refers to species that might not be considered to fall within the classical definition of "a molecule," e.g., solid support (e.g., synthesis support, chromatographic support, membrane), virus and microorganism.

"Activated derivatives of hydroxyl moieties," and equivalent species, refer to compounds in which an oxygen-containing leaving group is formally derived from a hydroxyl moiety.

"Activated derivatives of carboxyl moieties," and equivalent species, refer to compounds in which an oxygen-containing leaving group is formally derived from a carboxyl moiety.

The term "alkyl," by itself or as part of another substituent, means, unless otherwise stated, a straight or branched chain, or cyclic hydrocarbon radical, or combination thereof, which may be fully saturated, mono- or polyunsaturated and can include mono-, di- and multivalent radicals, having the number of carbon atoms designated (i.e. $C_1$-$C_{10}$ means one to ten carbons). Examples of saturated alkyl radicals include, but are not limited to, groups such as methyl, methylene, ethyl, ethylene, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, includes "alkylene" and those derivatives of alkyl defined in more detail below, such as "heteroalkyl." Alkyl groups, which are limited to hydrocarbon groups, are termed "homoalkyl".

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Also included are di- and multi-valent species such as "cycloalkylene." Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, species such as trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent, which can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Also included are di- and multi-valent linker species, such as "arylene." Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) ("alkyl group substituents") can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR"', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups ("aryl group substituents") are varied and are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl.

"Analyte," "target," "substance to be assayed", and "target species," as utilized herein refer to the species of interest in an assay mixture. The terms refer to a substance, which is detected qualitatively or quantitatively using a material, process or device of the present invention. Examples of such substances include cells and portions thereof, enzymes, antibodies, antibody fragments and other biomolecules, e.g., antigens, polypeptides, glycoproteins, polysaccharides, complex glycolipids, nucleic acids, effector molecules, receptor molecules, enzymes, inhibitors and the like and drugs, pesticides, herbicides, agents of war and other bioactive agents.

More illustratively, such substances include, but are not limited to, tumor markers such as α-fetoprotein, carcinoembryonic antigen (CEA), CA 125, CA 19-9 and the like; various proteins, glycoproteins and complex glycolipids such as β$_2$-microglobulin (β$_2$ m), ferritin and the like; various hormones such as estradiol (E$_2$), estriol (E$_3$), human chorionic gonadotropin (hCG), luteinizing hormone (LH), human placental lactogen (hPL) and the like; various virus-related antigens and virus-related antibody molecules such as HBs antigen, anti-HBs antibody, HBc antigen, anti-HBc antibody, anti-HCV antibody, anti-HIV antibody and the like; various allergens and their corresponding IgE antibody molecules; narcotic drugs and medical drugs and metabolic products thereof; and nucleic acids having virus- and tumor-related polynucleotide sequences.

The term, "assay mixture," refers to a mixture that includes the analyte and other components. The other components are, for example, diluents, buffers, detergents, and contaminating species, debris and the like that are found mixed with the target. Illustrative examples include urine, sera, blood plasma, total blood, saliva, tear fluid, cerebrospinal fluid, secretory fluids from nipples and the like. Also included are solid, gel or sol substances such as mucus, body tissues, cells and the like suspended or dissolved in liquid materials such as buffers, extractants, solvents and the like.

The term "drug" or "pharmaceutical agent," refers to bioactive compounds that cause an effect in a biological organism. Drugs used as affinity moieties or targets can be neutral or in their salt forms. Moreover, the compounds can be used in the present method in a prodrug form. Prodrugs are those compounds that readily undergo chemical changes under physiological conditions to provide the compounds of interest in the present invention.

Introduction

The present invention provides a class of reactive fluorescent compounds that are based upon the xanthene nucleus. Also provided are conjugates of the xanthene dyes with carrier molecules, including biological, non-biological and biologically active species. Selected xanthene labels described herein include a functionalized linker arm that is readily converted into an array of reactive derivatives without requiring a modification of the xanthene nucleus. Accordingly, the compounds of the invention provide an as yet undisclosed advantage, allowing facile access to an array of conjugates between the linker arm-derivatized xanthene nucleus and carrier molecules.

Residing in the field of fluorescent labels, the present invention provides benefits of particular note. Fluorescent labels have the advantage of requiring few precautions in handling, and being amenable to high-throughput visualization techniques (optical analysis including digitization of the image for analysis in an integrated system comprising a computer). Exemplary labels exhibit one or more of the following characteristics: high sensitivity, high stability, low background, low environmental sensitivity and high specificity in labeling. Many fluorescent labels based upon the xanthene nucleus are commercially available from the SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.), as well as many other commercial sources known to one of skill. Furthermore, those of skill in the art will recognize how to select an appropriate xanthene-based fluorophore for a particular application and, if it not readily available commercially, will be able to synthesize the necessary fluorophore de novo or synthetically modify commercially available xanthene compounds to arrive at the desired fluorescent label.

The compounds, probes and methods discussed in the following sections are generally representative of the compositions of the invention and the methods in which such compositions can be used. The following discussion is intended as illustrative of selected aspects and embodiments of the present invention and it should not be interpreted as limiting the scope of the present invention.

Description Of The Embodiments

In a first aspect, the present invention provides a fluorescent compound having the formula:

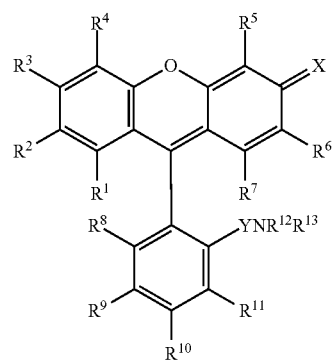

in which $R^1$, $R^2$ and $R^4$-$R^{11}$ are each independently selected from groups such as substituted or unsubstituted alkyl, substituted or unsubstituted heteroalkyl, substituted or unsubstituted aryl, substituted or unsubstituted heteroaryl, substituted or unsubstituted heterocycloalkyl, halogen, H, $NO_2$, CN and $C(Z^1)R^{14}$, $NR^{15}R^{16}$ and $Z^2R^{16}$. $R^3$ is selected from $Z^2R^{16}$ and $NR^{15}R^{16}$.

$Z^1$ represents O, S or NH. $Z^2$ is either O or S. Groups corresponding to $R^{15}$ include H, substituted or unsubstituted alkyl, and substituted or unsubstituted heteroalkyl. $R^{16}$ is selected from H, substituted or unsubstituted alkyl and substituted or unsubstituted heteroalkyl and $C(Z^3)R^{17}$. $R^{15}$ and $R^{16}$, together with the nitrogen to which they are attached, can also be any nitrogen-containing reactive group. Exemplary groups include $-NHNH_2$, $-N=C=S$ and $-N=C=O$.

$Z^3$ represents O, S or NH. The symbol $R^{17}$ represents groups such as substituted or unsubstituted alkyl, substituted or unsubstituted heteroalkyl, $OR^{18}$, and $NR^{19}R^{20}$. $R^{18}$ represents H, substituted or unsubstituted alkyl, substituted or unsubstituted heteroalkyl, substituted or unsubstituted aryl, substituted or unsubstituted heteroaryl and $C(O)R^{21}$. $R^{19}$ and $R^{20}$ are symbols representing groups independently selected from H, substituted or unsubstituted alkyl and substituted or unsubstituted heteroalkyl. $R^{21}$ is substituted or unsubstituted alkyl or substituted or unsubstituted heteroalkyl.

The symbol Y represents either C(O) or $S(O)_2$. X is $(NR^{22}R^{23})$ or (O). $R^{22}$ and $R^{23}$ are independently selected and are members selected from H, substituted or unsubstituted alkyl and substituted or unsubstituted heteroalkyl.

$R^{12}$ or $R^{13}$ are independently selected from substituted or unsubstituted alkyl, substituted or unsubstituted heteroalkyl, substituted or unsubstituted heterocycloalkyl, substituted or unsubstituted aryl and substituted or unsubstituted heteroaryl, with the proviso that at least one of $R^{12}$ or $R^{13}$ includes an oxygen-containing reactive group or a carrier molecule to which the dye of the invention is conjugated through a moiety produced by reaction of the oxygen-containing reactive group with a reactive group on the carrier molecule of complementary reactivity. $R^{12}$ and $R^{13}$, together with the nitrogen atom to which they are attached are optionally joined to form a ring. Exemplary rings include 4-8-membered heterocylic and heteroaryl rings. When $R^{12}$ and $R^{13}$, together with the nitrogen to which they are attached ("first nitrogen") form a piperazine ring in which the second nitrogen atom is functionalized with an alkyl moiety bearing an oxygen-containing reactive group, the reactive group is preferably a phosphoramidite. A piperazinyl-xanthene can be conjugated to another species, e.g., a nucleic acid, saccharide, or a lipid, through oxygen-containing reactive groups other than a phosphoramidite, e.g, an activated carboxylic acid, a carbonate, a reactive hydroxyl moiety, i.e., —OH, and R—X in which R is a linker or bond to the xanthene and —X is a leaving group, e.g., a sulfonate, or halide.

The substituents on the aryl ring nuclei can be joined to form rings. For example, in one embodiment in which $R^3$ is $NR^{15}R^{16}$, $R^2$, $R^4$ and $R^{15}$ and $R^{16}$, together with the nitrogen atom to which they are bound, are fused with the phenyl moiety to which $NR^{15}R^{16}$, $R^2$ and $R^4$ are bound, forming a substituted or unsubstituted ring system having the general formula:

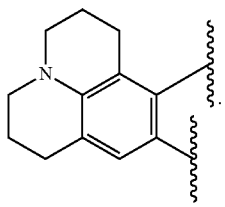

In yet another embodiment in which X is $NR^{22}R^{23}$, $R^5$, $R^6$ and $R^{22}$ and $R^{23}$, together with the nitrogen atom to which they are bound, are fused with the unsaturated 6-member ring to which $NR^{22}R^{23}$, $R^5$ and $R^6$ are bound, forming a substituted or unsubstituted ring system having the general formula:

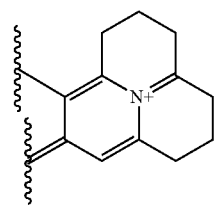

The present invention also provides a conjugate between a carrier molecule, e.g., a nucleic acid, and a fluorescent compound of the invention, which is covalently or ionically bound to a moiety of the carrier molecule. When the carrier molecule is a nucleic acid, representative moieties at which the fluorescent compounds of the invention are attached include the sugar moiety, at O- and/or C-centers; endo- and/or exo-cyclic amines, carbon atoms of nucleobase moieties, and internucleotide bridges. In still a further exemplary embodiment, the conjugate between the compound of the invention and the carrier molecule includes at least one moiety that quenches the fluorescence emission of the compound of the invention.

The compounds of the invention include a linker moiety as a component of either or both $R^{12}$ and $R^{13}$. An exemplary linker is a substituted or unsubstituted alkyl or substituted or unsubstituted heteroalkyl moiety that includes a reactive group at the terminus of the linker. In the conjugates of the invention, the reactive group is converted to a linking moiety by reaction with a group of complementary reactivity on the species to which the dye is conjugated.

In a representative embodiment, the invention provides a xanthene dye, as set forth above, in which $R^{12}$ and/or $R^{13}$ includes a linker arm moiety having the formula:

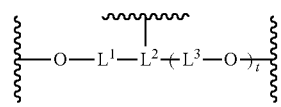

wherein $L^1$, $L^2$ and $L^3$ are members independently selected from a bond, substituted or unsubstituted alkyl and substituted or unsubstituted heteroalkyl. The index "t" is 0 or 1. Exemplary linker arms according to this formula include one or more amide, urethane, ether, ester, urea, sulfonamide, sulfoxide, amine, sulfide, phosphate, or keto moiety. In another exemplary linker of use in the invention, one or more of $L^1$, $L^2$ or $L^3$ includes from 1 to 6 ethylene glycol moieties. The points of attachment shown above represent members independently selected from H, substituted or unsubstituted alkyl and substituted or unsubstituted heteroalkyl, a hydroxyl-protecting group, a phosphate moiety, a phosphodiester moiety, a phosphorus-containing internucleotide bridge, a solid support, a carrier molecule and a reactive functional group, e.g., $-OP(O)(OR^\circ)(N(R^pR^q))_2$. The groups represented by the symbols $R^o$, $R^p$ and $R^q$ are members independently selected from H, substituted or unsubstituted $C_1$-$C_6$ alkyl and substituted or unsubstituted $C_1$-$C_6$ heteroalkyl; and the index "s" is an integer from 1 to 20. In an exemplary embodiment, $R^o$ is $CH_2CH_2CN$.

A subset of $R^{12}$ and $R^{13}$ moieties according to the motif set forth above has the formula:

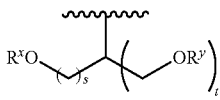

in which the symbols $R^x$ and $R^y$ represent groups that are independently selected from H, substituted or unsubstituted alkyl and substituted or unsubstituted heteroalkyl, a hydroxyl-protecting group, a phosphate moiety, a phosphodiester moiety, a phosphorus-containing internucleotide bridge, a solid support, a carrier molecule and a reactive functional group, e.g., $-OP(O)(OR^o)(N(R^pR^q))_2$. The groups represented by the symbols $R^o$, $R^p$ and $R^q$ are members independently selected from H, substituted or unsubstituted $C_1$-$C_6$ alkyl and substituted or unsubstituted $C_1$-$C_6$ heteroalkyl; and the index "s" is an integer from 1 to 20. In an exemplary embodiment, $R^o$ is $CH_2CH_2CN$.

The invention also provides fluorescent compounds in which at least one of $R^x$ and $R^y$ comprises a moiety having the formula:

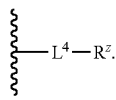

$L^4$ is a member selected from a bond, substituted or unsubstituted alkyl and substituted or unsubstituted heteroalkyl; and $R^z$ is a member selected from a reactive functional group, solid support, or a carrier molecule, e.g., a nucleic acid, a saccharide and a peptide.

In selected compounds of the invention, $L^4$ comprises a moiety having the formula:

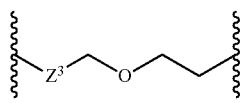

wherein the symbol $Z^3$ represents either $CH_2$ or $C=O$.

In another embodiment, the invention provides xanthene dyes in which one of the substituents on the xanthene nucleus, preferably $R^{12}$, includes a moiety having the structure:

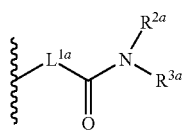

in which $L^{1a}$ is a member selected from substituted or unsubstituted alkyl, and substituted or unsubstituted heteroalkyl groups. The symbols $R^{2a}$ and $R^{3a}$ represent groups that are independently selected from H, substituted or unsubstituted alkyl, and substituted or unsubstituted heteroalkyl. The groups $R^2$ and $R^3$, together with the nitrogen to which they are attached, are optionally joined to form a ring. Preferred ring structures include substituted or unsubstituted $C_5$-$C_7$ cycloalkyl and substituted or unsubstituted 5-7-membered heterocycloalkyl.

An exemplary linker species according to the motif presented above includes an $NR^{12}R^{13}$ moiety that has the formula:

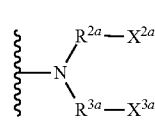

in which $R^{2a}$ and $R^{3a}$ are members independently selected from substituted or unsubstituted alkyl and substituted or unsubstituted heteroalkyl. The symbols $X^{2a}$ and $X^{3a}$ represent groups that are independently selected from H, substituted or unsubstituted lower alkyl, substituted or unsubstituted heteroalkyl, reactive functional groups, a bond to a solid support and a bond to a carrier molecule. When the carrier molecule is a nucleic acid, the bond can be to a nucleobase (e.g., to C or N), sugar (e.g., to C or O) or internucleotide bridge (e.g., to P, O, S, C or N).

Exemplary identities for $X^{2a}$ and $X^{3a}$ include $-CH_3$, $-OX$, $-COOX$, $-NHX$, $-SX$, halogen and $-OP(O)(OR^o)(N(R^pR^q))_2$. X is H or an activating group, e.g., N-hydroxysuccinimide, or sulfonate ester. The groups represented by the symbols $R^o$, $R^p$ and $R^q$ are members independently selected from H, substituted or unsubstituted $C_1$-$C_6$ alkyl and substituted or unsubstituted $C_1$-$C_6$ heteroalkyl; and the index "s" is an integer from 1 to 20. In an exemplary embodiment, $R^o$ is $CH_2CH_2CN$.

When $X^{2a}$ or $X^{3a}$ is a component of a linkage between a species of the invention and a carrier molecule or solid support, it is modified in a manner that satisfies the rules of valence, e.g., $-OH$ becomes $-O-$; COOH becomes COOR, CONRR', etc.

In another preferred embodiment, a member selected from $R^{2a}$, $R^{3a}$ and combinations thereof comprises a polyether. Preferred polyethers include, for example, poly(ethylene glycol), poly(propyleneglycol) and copolymers thereof. The polyether may be internal to the $R^{2a}$ or $R^{3a}$ group or it may form the free terminus of the group. When the polyether is at the terminus of the group, the terminal $-O-$ moiety is present as $-OH$, alkoxy or one of a variety of the groups referred to herein as substituents for alkyl moieties. See, for example, Shearwater Polymers, Inc. Catalog of Poly(ethylene glycol) Derivatives 2002.

In a further exemplary embodiment, $NR^{12}R^{13}$ has the formula:

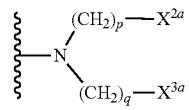

in which the indexes p and q are integers independently selected from 1 to 20, inclusive, preferably from 2 to 16, inclusive. $X^{2a}$ and $X^{3a}$ are as described above.

In yet another exemplary embodiment, $NR^{12}R^{13}$ has the formula:

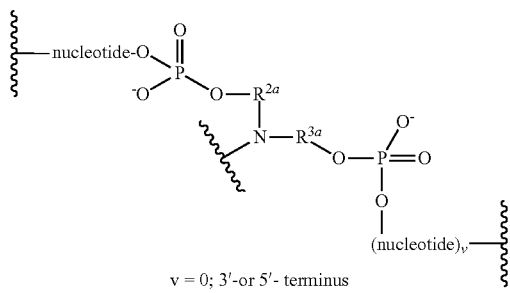

v = 0; 3'- or 5'- terminus in which the index "v" is 0 or 1. $R^{2a}$ and $R^{3a}$ are independently selected from a bond, substituted or unsubstituted alkyl or substituted or unsubstituted heteroalkyl moieties (e.g., ethers, polyethers). When "v" is 0, the resulting phosphate in the structure above can alternatively be OH (i.e., 3'- or 5'-hydroxyl). In other words, although represented as interposed between two nucleotides, the fluorescent label of the invention can be placed at any point between two nucleoside or nucleotide subunits in a nucleic acid. Thus, exemplary compounds include $NR^{12}R^{13}$ at an internal position of the nucleic acid. In other exemplary embodiments, $NR^{12}R^{13}$ is tethered to the nucleic acid at the linkage between the 5' and 5'-1 residues and/or the linkage between the 3' and 3'-1 residues.

In a further exemplary embodiment, $NR^{12}R^{13}$ has the formula:

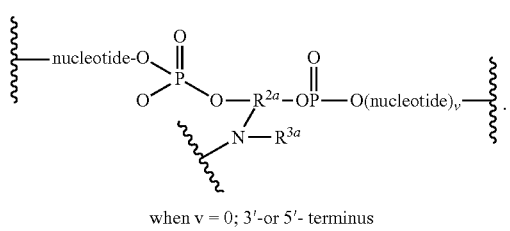

when v = 0; 3'-or 5'- terminus

When "v" is 0, the resulting phosphate in the structure above can alternatively be OH (i.e., 3"- or 5'-hydroxyl).

The invention also provides nucleic acid derivatives in which a compound of the invention is conjugated to a sugar moiety of the nucleic acid. An exemplary species according to this motif has the formula:

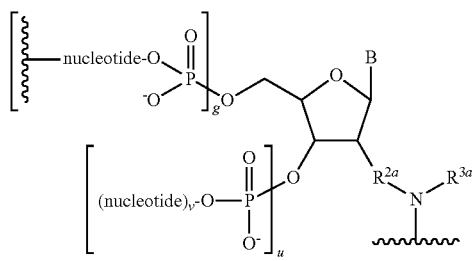

in which the index u and the index g independently represent 0, 1 or a number greater than one, with the proviso that at least one of u and g is preferably non-zero. Although shown attached to the 2' carbon of the 3'-terminus of the nucleic acid, those of skill will appreciate that a similar structure tethered to the 5'-terminus, or an internal site of the nucleic acid is within the scope of the invention. Moreover, the group can be tethered through the O atom of a 2'-hydroxyl. When "u" is 0, the phosphate/phosphodiester group is optionally OH.

Moreover, the agents of the invention can be conjugated through the 3'- and/or 5'-hydroxyl moiety of a nucleic acid.

In another exemplary embodiment, $NR^{12}R^{13}$ has the formula:

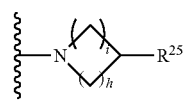

in which h and i are members independently selected from integers such that the sum (h+i) is from 4-8. $R^{25}$ is a reactive functional group, e.g., an oxygen-containing reactive functional group, or a substituted or unsubstituted alkyl or substituted or unsubstituted heteroalkyl moiety bearing an oxygen-containing reactive functional group. In an exemplary embodiment, $R^{25}$ is a phosphoramidite or a species that includes a phosphoramidite. In a further exemplary embodiment, h and i are both 2.

Representative compounds of the invention are set forth in FIG. 1.

Synthesis

The compounds of the invention are synthesized by an appropriate combination of generally well-known synthetic methods. Techniques useful in synthesizing the compounds of the invention are both readily apparent and accessible to those of skill in the relevant art. The discussion below is offered to illustrate certain of the diverse methods available for use in assembling the compounds of the invention, it is not intended to define the scope of reactions or reaction sequences that are useful in preparing the compounds of the present invention.

The compounds of the invention can be prepared as a single isomer or a mixture of isomers, including, for example cis-isomers, trans-isomers, diastereomers and stereoisomers. In a preferred embodiment, the compounds are prepared as substantially a single isomer. Isomerically pure compounds are prepared by using synthetic intermediates that are isomerically pure in combination with reactions that either leave the stereochemistry at a chiral center unchanged or result in its complete inversion. Alternatively, the final product or intermediates along the synthetic route can be resolved into a single isomer. Techniques for inverting or leaving unchanged a particular stereocenter, and those for resolving mixtures of stereoisomers are well known in the art and it is well within the ability of one of skill in the art to choose an appropriate resolution or synthetic method for a particular situation. See, generally, Furniss et al. (eds.) VOGEL'S ENCYCLOPEDIA OF PRACTICAL ORGANIC CHEMISTRY 5$^{TH}$ ED., Longman Scientific and Technical Ltd., Essex, 1991, pp. 809-816; and Heller, *Acc. Chem. Res.* 23: 128 (1990).

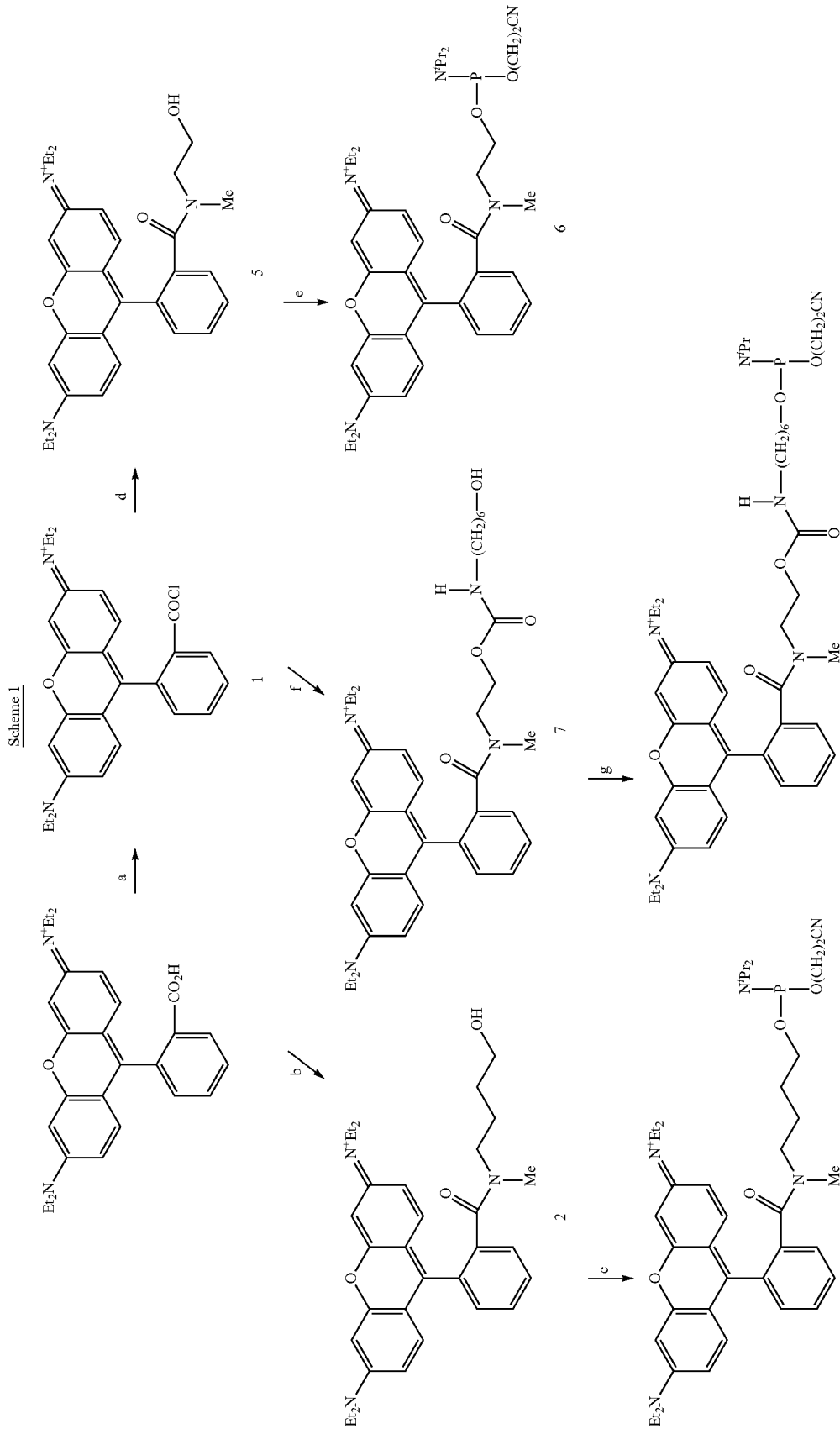

An exemplary synthetic route to compounds of the invention is set forth in Scheme 1. Rhodamine B acid chloride 1 is prepared by the action of phosphorus oxychloride on the precursor dye carboxylic acid. The activated dye is reacted with selected aminoalcohols to form corresponding amides 2 and 5. The linker arm is readily extended by activating the hydroxyl moiety of 5 and forming urethane 7 with an appropriate amino alcohol. The dyes bearing the hydroxyl terminated linker arms are converted to the corresponding phosphoramidites 3, 6 and 8.

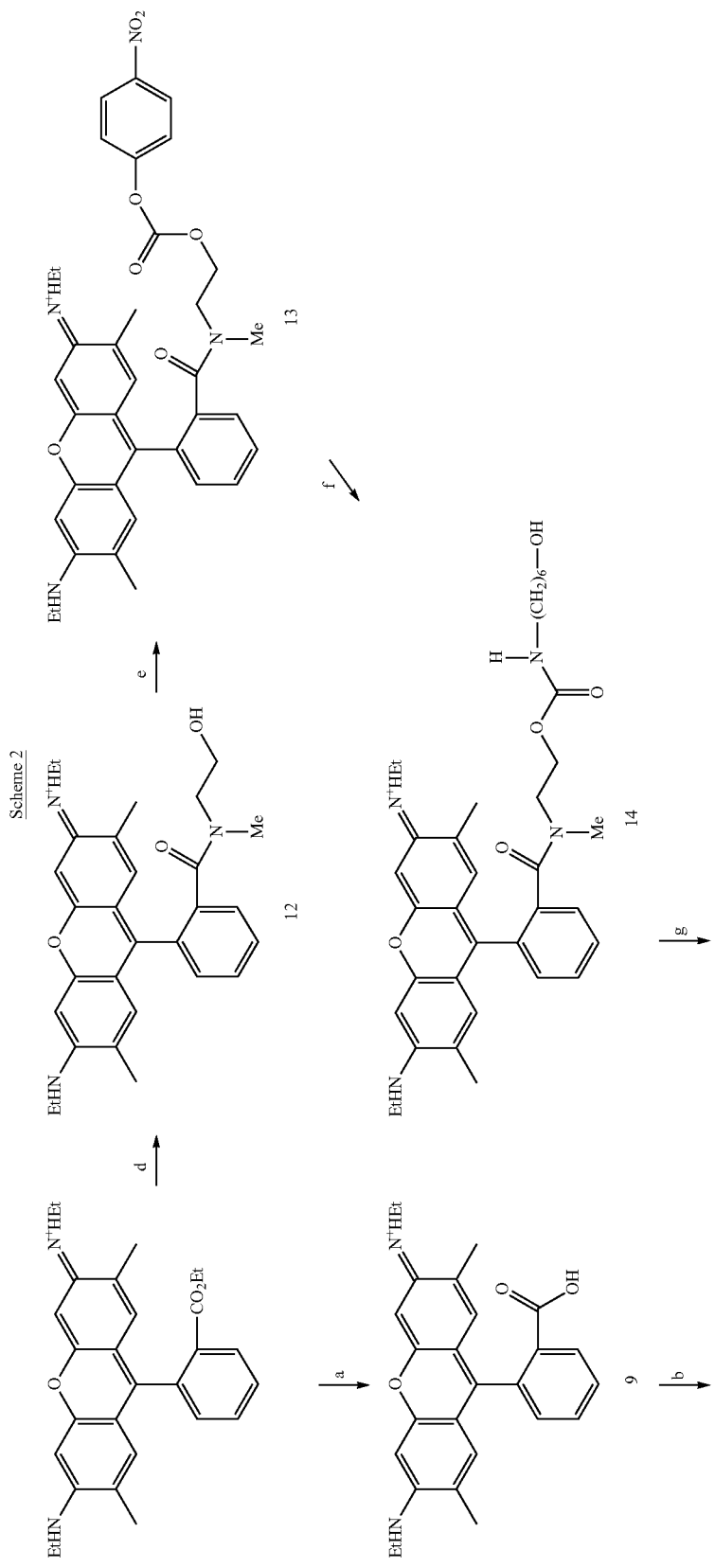
Scheme 2

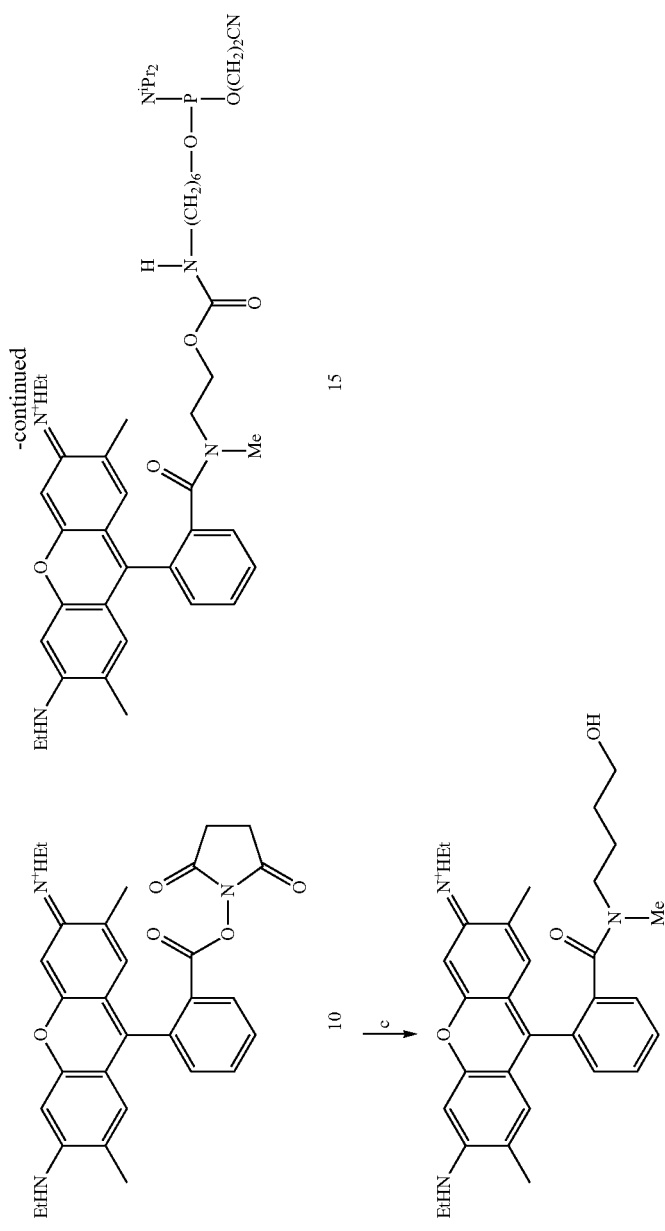
a. DMSO/1N NaOH(aq).; b. N,N,N'N'-tetramethyl-O-(N-succinimidyl) uronium tetrafluoroborate, diisopropylethylamine, DMF: c. N-methylethanolamine, DMF: d. N-methylaminobutanol, 120° C.: e. p-nitrophenyl chloroformate, pyridine, dioxane: f. 6- amino-1-hexanol, aqueous Na₂CO₃, THF: g. N,N,N'N'-tetraisopropyl-β-cyanoethylphosphane, 1-H tetrazole, MeCN, DCM.

Scheme 2 outlines the preparation of a series of linker arm derivatized xanthene dyes of the invention. The ethyl ester of Rhodamine 6G was hydrolyzed in base, affording the corresponding acid 9, which was activated as the N-hydroxysuccinimide ester 10 and converted to the corresponding hydroxyl-terminated alkyl amide 11. Alternatively, the ester is aminolysed with an aminoalcohol, producing amide 12. The amide is activated as the p-nitrophenylchloroformate 13 and coupled with 6-amino-1-hexanol, affording 14, which is readily converted to the corresponding phosphoramidite 15.

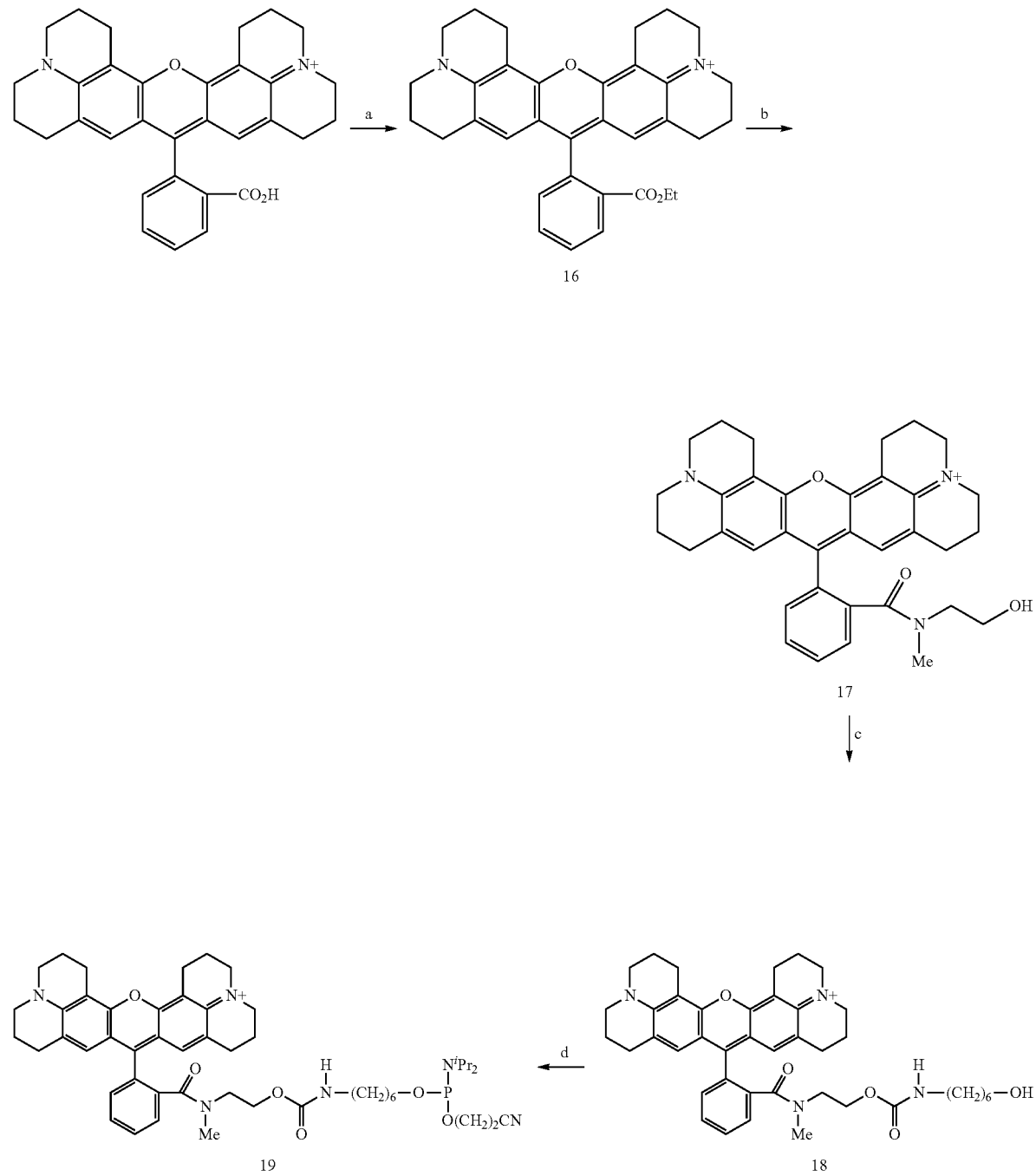

Scheme 3 a. EtOH, ClSiMe$_3$, reflux: b. N-methylethanolamine, 120° C.: c. p-nitrophenyl chloroformate, pyridine, dioxane: d. 6-amino-1-hexanol, aqueous Na$_2$CO$_3$, THF: e. N,N,N'N'-tetraisopropyl-β-cyanoethylphosphane, 1-H tetrazole, MeCN, DCM.

Scheme 3 sets out an exemplary route for preparing a linker arm derivatized dye and the corresponding phosphoramidite from rhodamine 101. The dye-linker arm conjugate 17 is formed by aminolysis of ester 16 with N-methylaminoethanol. The p-nitrophenylcarbonate activated analogue of 17 is reacted with 6-amino-1-hexanol, providing urethane 18, which is converted to phosphoramidite 19.

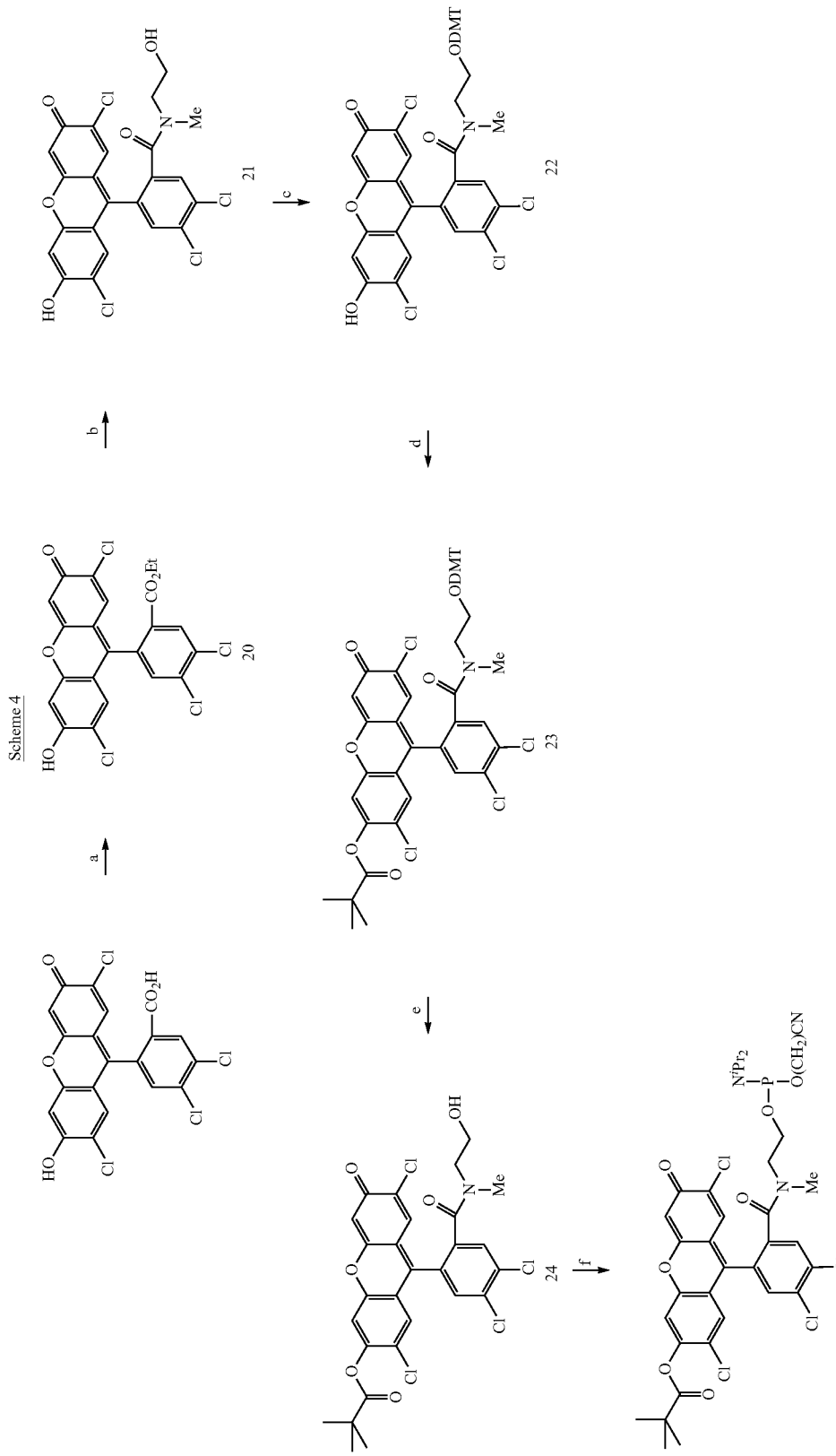
a. EtOH, ClSiMe₃, reflux; b. N-methyl-ethanolamine, 120° C.; c. dimethoxytrityl chloride, pyridine; d. Me₃C(O)Cl, pyridine; e. 3% Cl₂CHCOOH; f. N,N,N',N'-tetraisopropyl-β-cyanoethylphosphane, 1-H tetrazole, MeCN, DCM.

In Scheme 4, ethyl ester 20 is formed by the action of chlorotrimethylsilane and ethanol on the parent compound. Aminolysis of the ester with N-methylaminoethanol affords amide 21. Protection of the hydroxyl moiety as the DMT ether provides 22, and protection of the phenol-like hydroxyl as the t-butylacetyl group results in 23. The DMT moiety is removed with dichloroacetic acid and the resulting alcohol 24 is converted to the phosphoramidite 25.

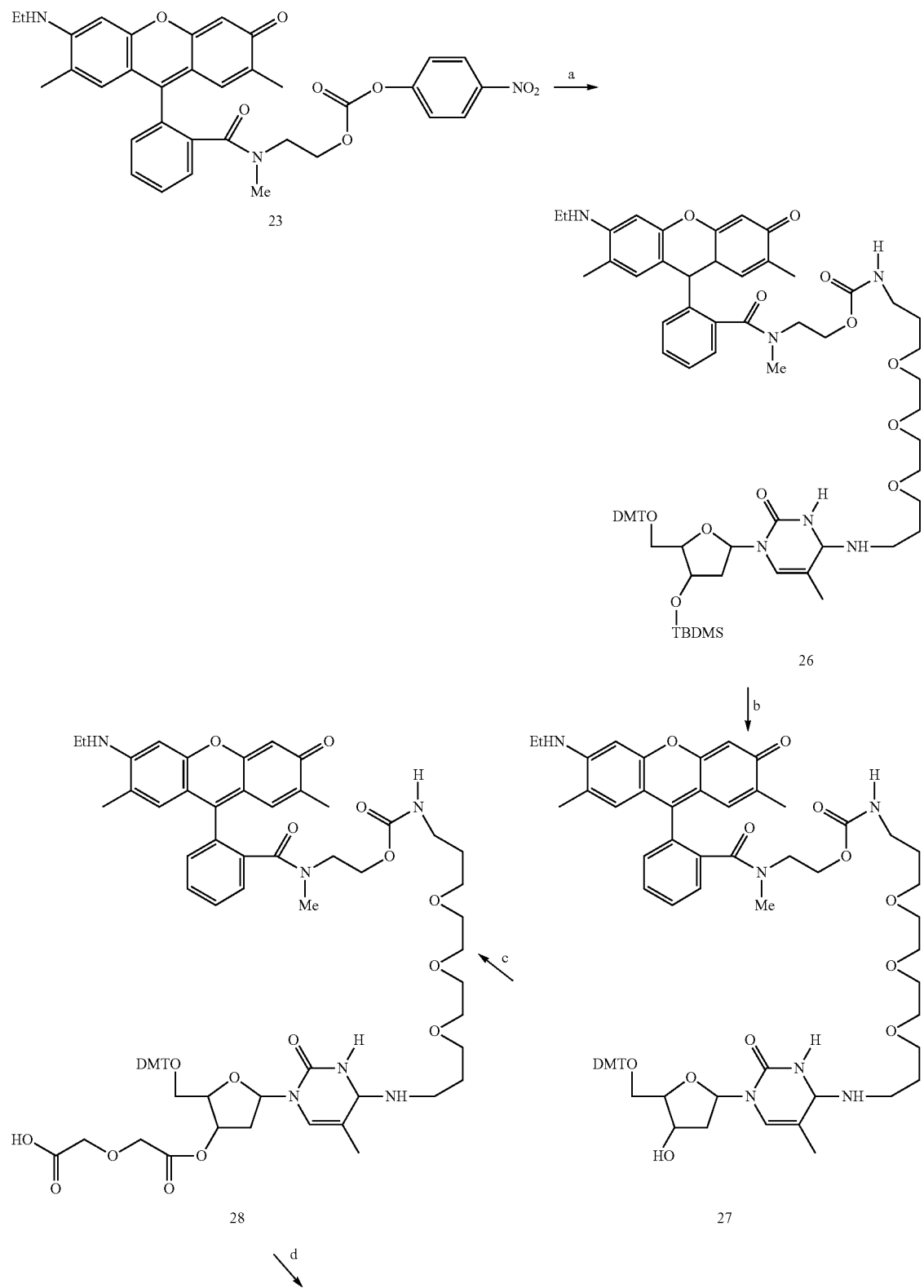

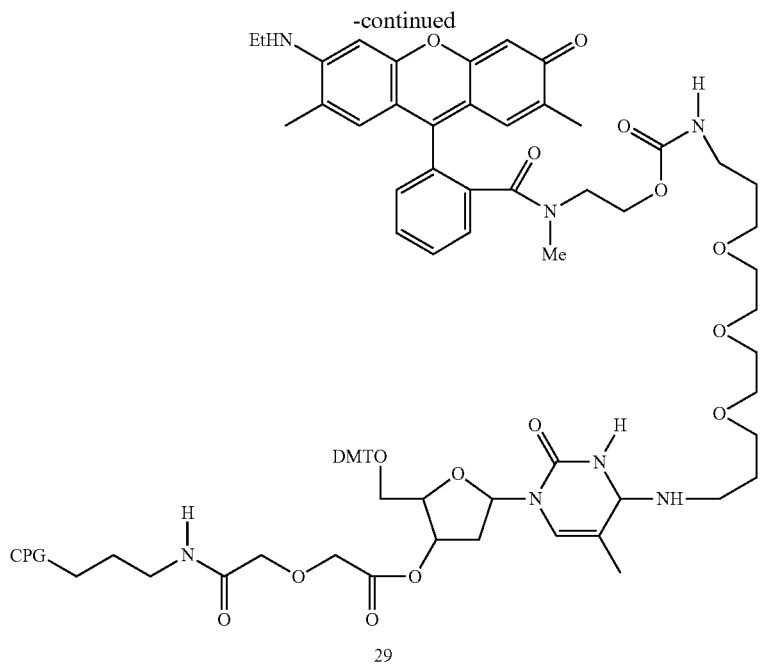

29 a. N⁴-(2-(4,7,10-trioxa-1,13-tridecanediamine)-5-methyl-5'-(4,4'-dimethoxy-trityl)-3'-O-tert-butyldimethylsilyl-2'deoxycytidine, NaHCO₃, THF: b. tetrabutylammonium fluoride, THF: c diglycolic anhydride, N-methylimidazole, pyridine: d. CPG, Bop, N-methylmorpholine, THF.

As shown in Scheme 5, p-nitrophenylcarbonate 13 is converted to urethane 26 with N⁴-(2-(4,7,10-trioxa-1,13-tridecanediamine)-5-methyl-5'-(4,4'-dimethoxytrityl)-3'-O-tert-butyldimethylsilyl-2'deoxycytidine. The TBDMS group is removed from the urethane and the resulting product 27 is reacted with diglycolic anhydride to afford the acid 28 which is conjugated to activated controlled pore glass, affording 29.

Each of the phosphoramidites described above and the CPG-immobilized conjugate 29 are of use in the synthesis of nucleic acids. The phosphoramidites are cleanly coupled to a nucleic acid as demonstrated by chromatographic analysis of TTCGATAAGTCTAG, labeled at the 5'-G moiety with a compound of the invention.

Figure 2:
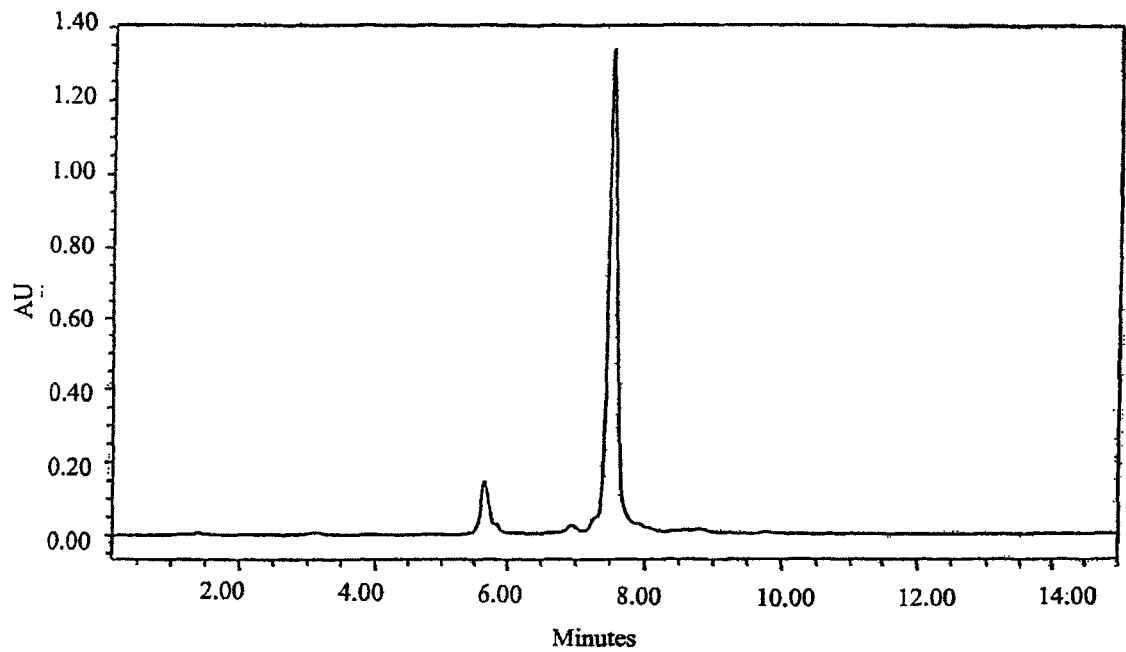
FIG. 2 is a representative reverse phase HPLC trace of 3'-TTCGATAAGTCTAG-5', 5' labeled with 15.
Figure 3:
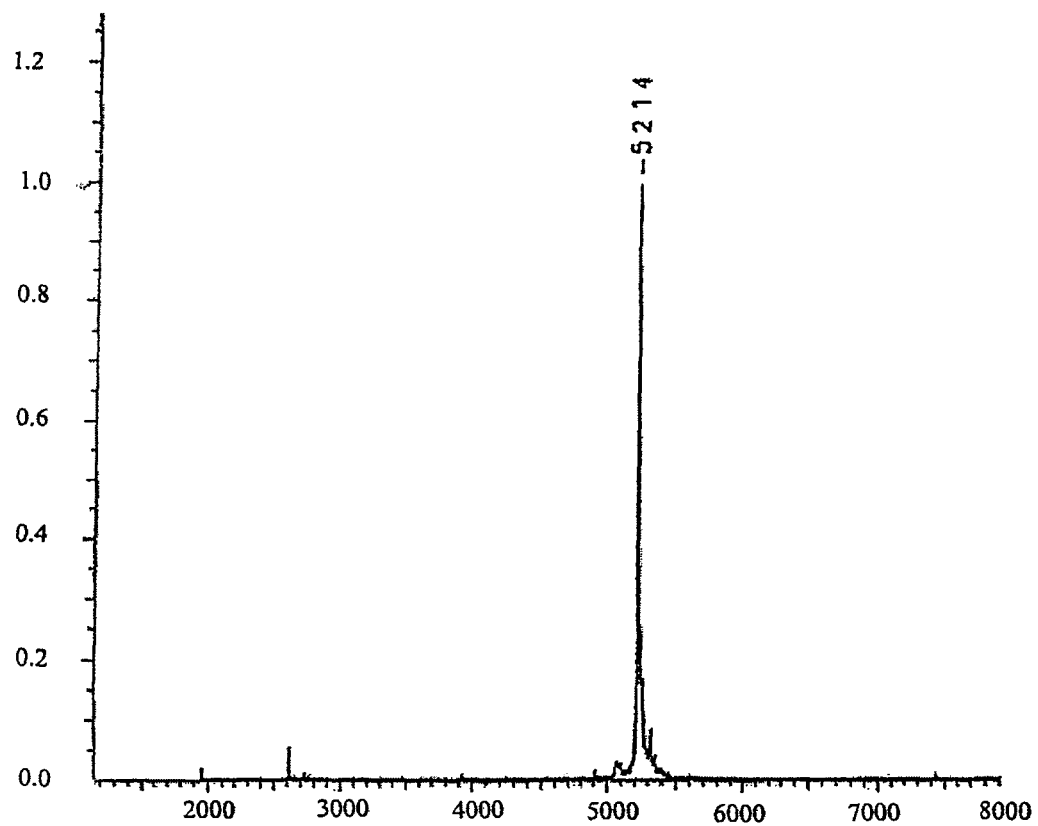
FIG. 3 is a representative mass spectrum of 3'-TTCGATAAGTCTAG-5', 5' labeled with 15.
Figure 4:
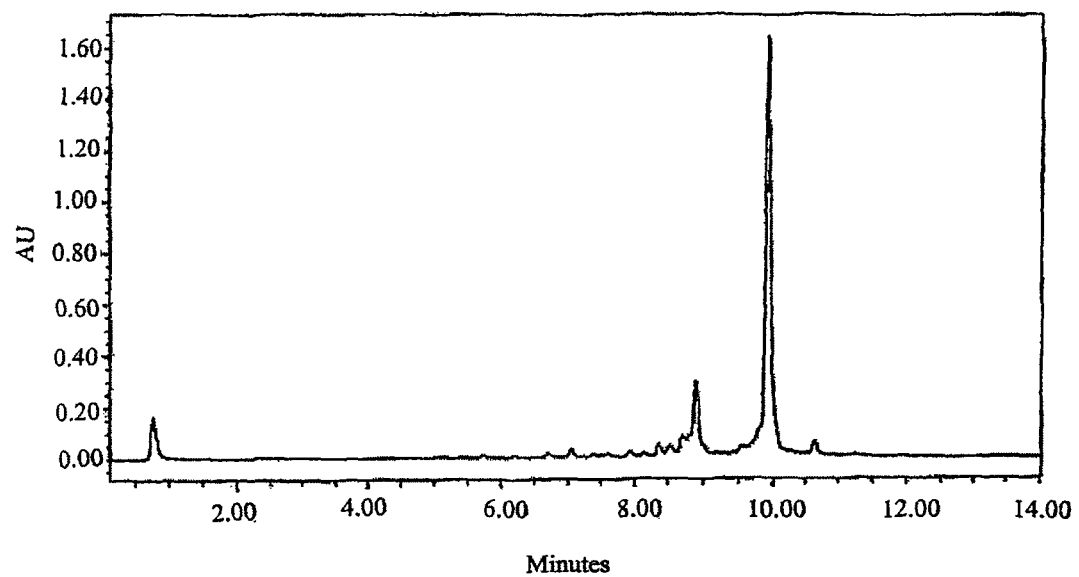
FIG. 4 is a representative anion exchange HPLC trace of 3'-TTCGATAAGTCTAG-5', 5' labeled with 25.
Figure 5:
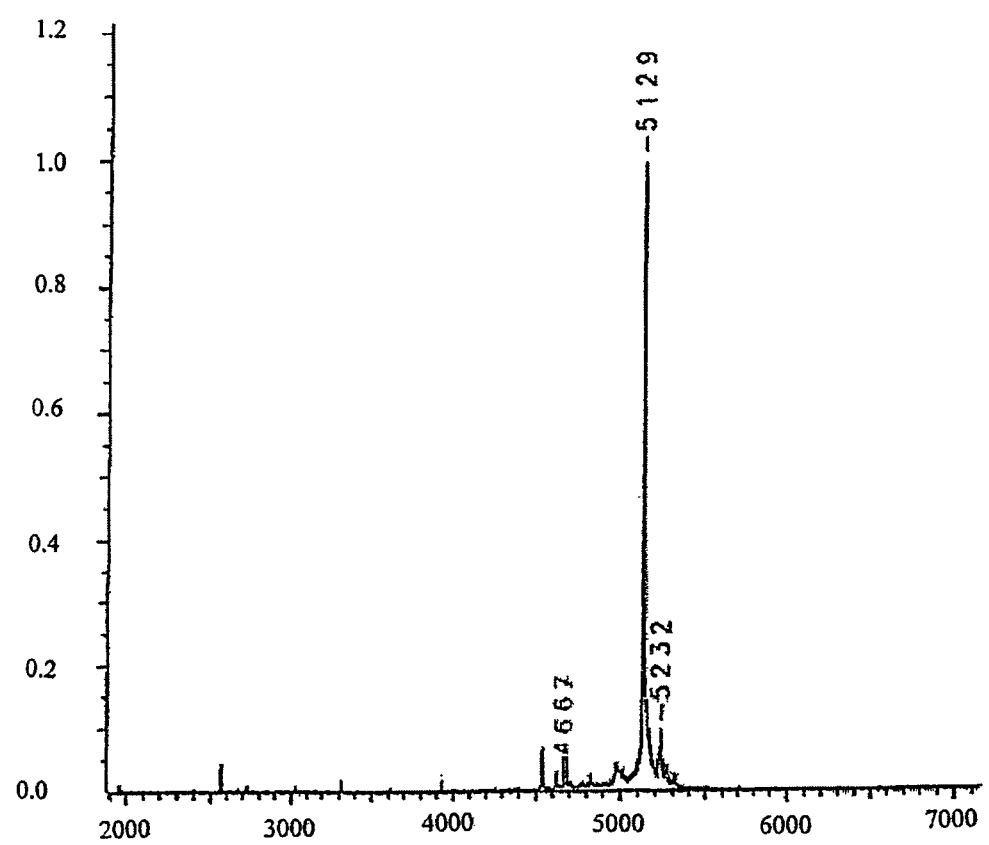
FIG. 5 is a representative mass spectrum of 3'-TTCGATAAGTCTAG-5', 5' labeled with compound 25.
Figure 6:
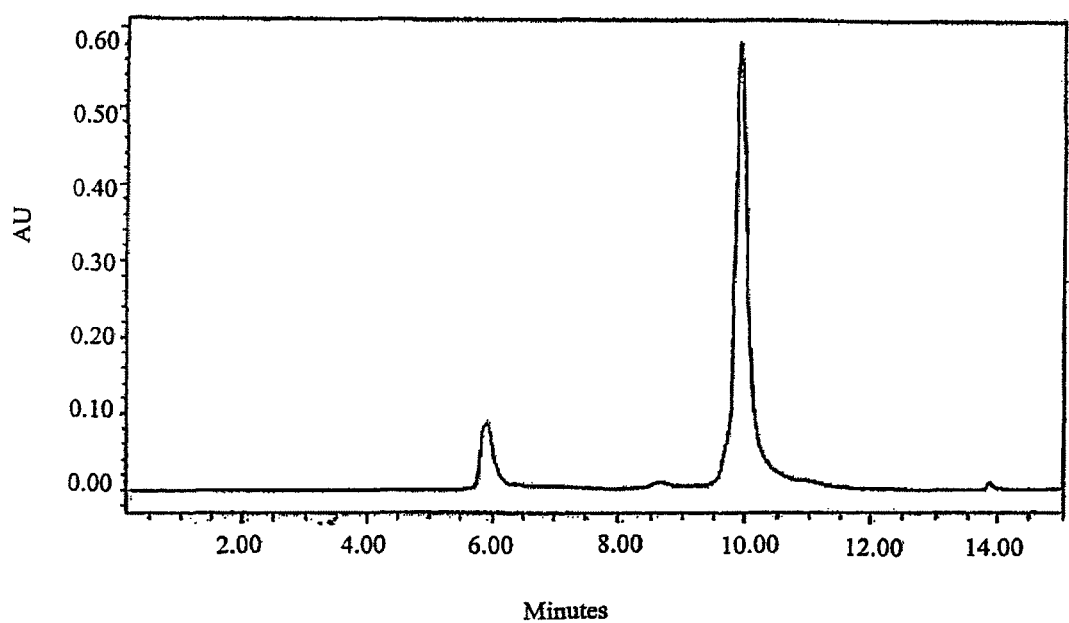
FIG. 6 is a representative reverse phase HPLC trace of 3'-TTCGATAAGTCTAG-5', 5' labeled with compound 19.
Figure 7:
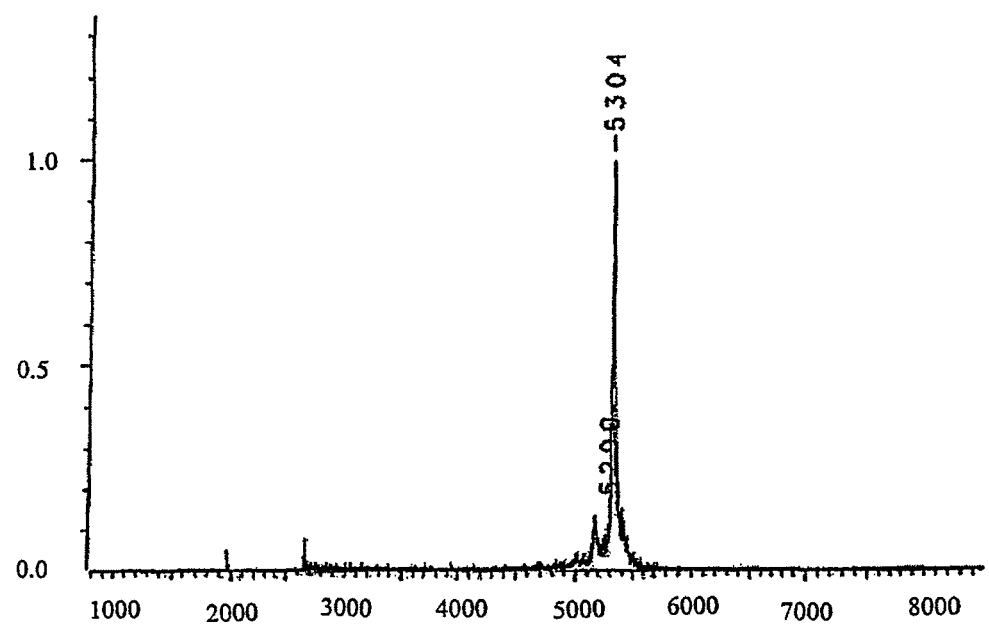
FIG. 7 is a representative mass spectrum of 3'-TTCGATAAGTCTAG-5', 5' labeled with compound 19.
Figure 8:
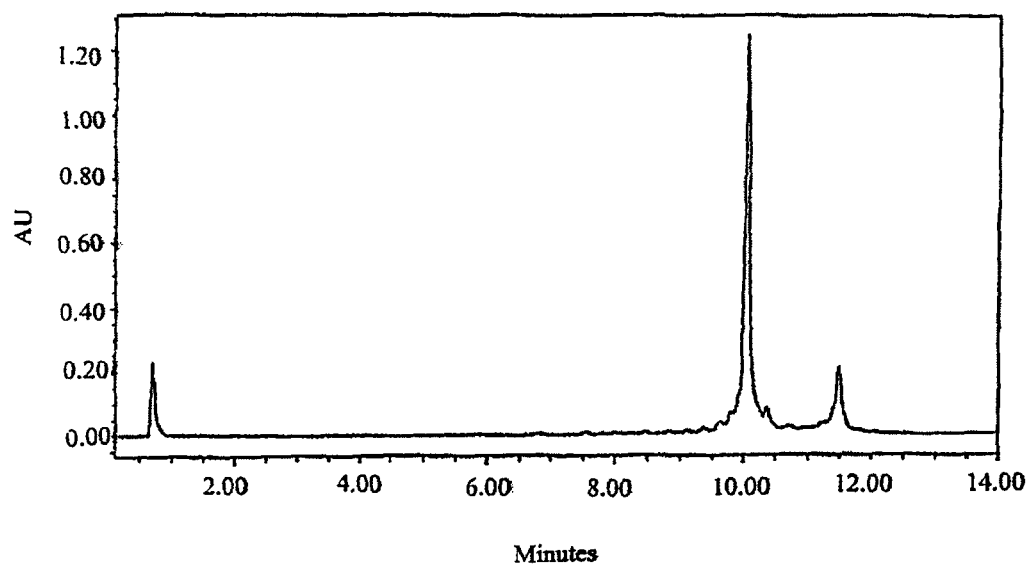
FIG. 8 is a representative anion exchange HPLC trace of 3'-TTCGATAAGTCTAG-5', 3' labeled by using dye bearing CPG compound 29.
Figure 9:
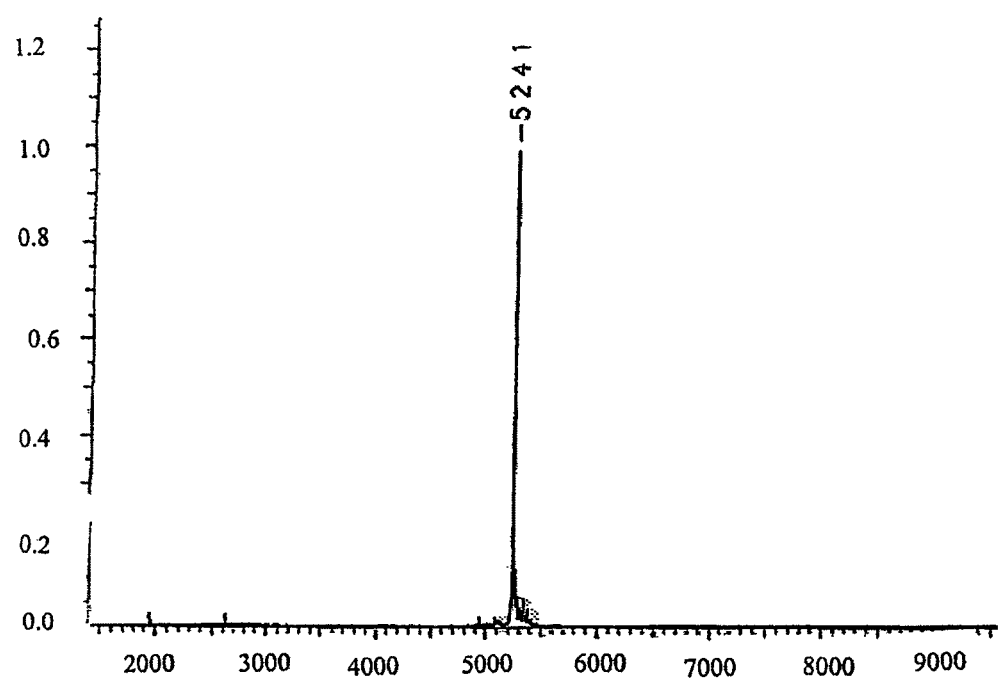
FIG. 9 is a representative mass spectrum of 3'-TTCGATAAGTCTAG-5', 3' labeled by using dye bearing CPG compound 29.
Figure 10:
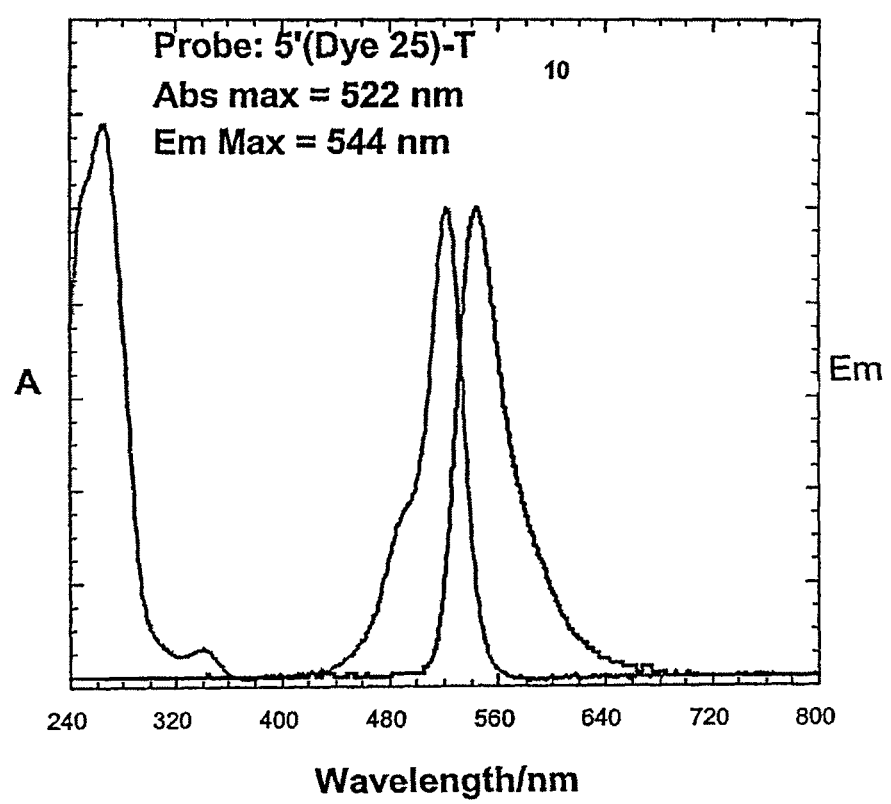
FIG. 10 is an overlay of absorption and emission spectra of 5'-TTTTTTTTTT-3' 5' labeled with 25.
Figure 11:
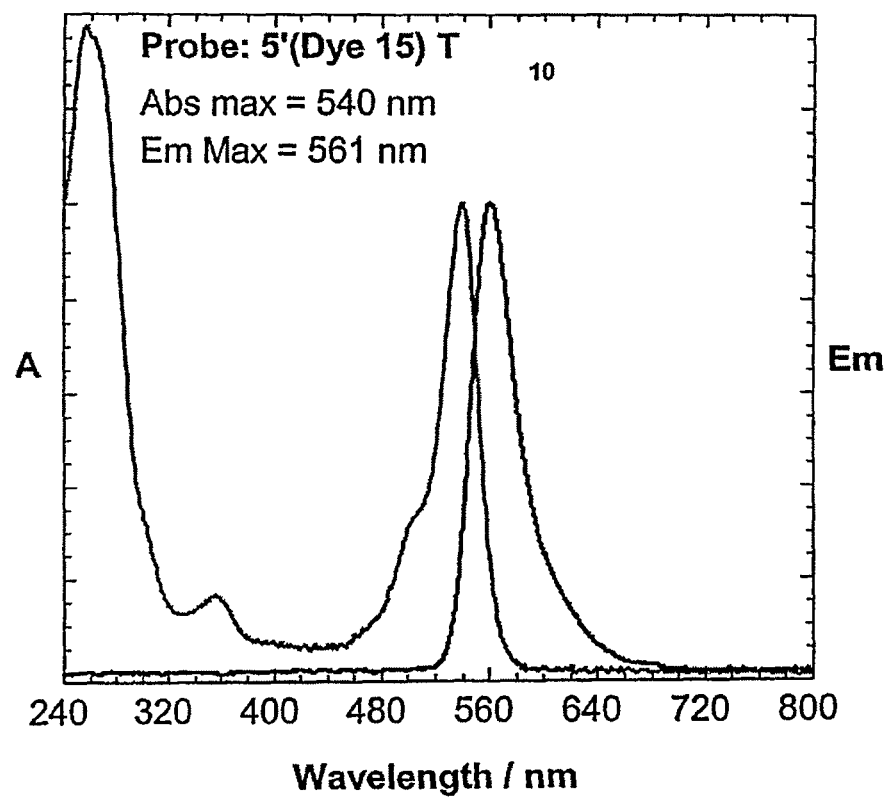
FIG. 11 is an overlay of absorption and emission spectra of 5'-TTTTTTTTTT-3' 5' labeled with 15.
Figure 12:
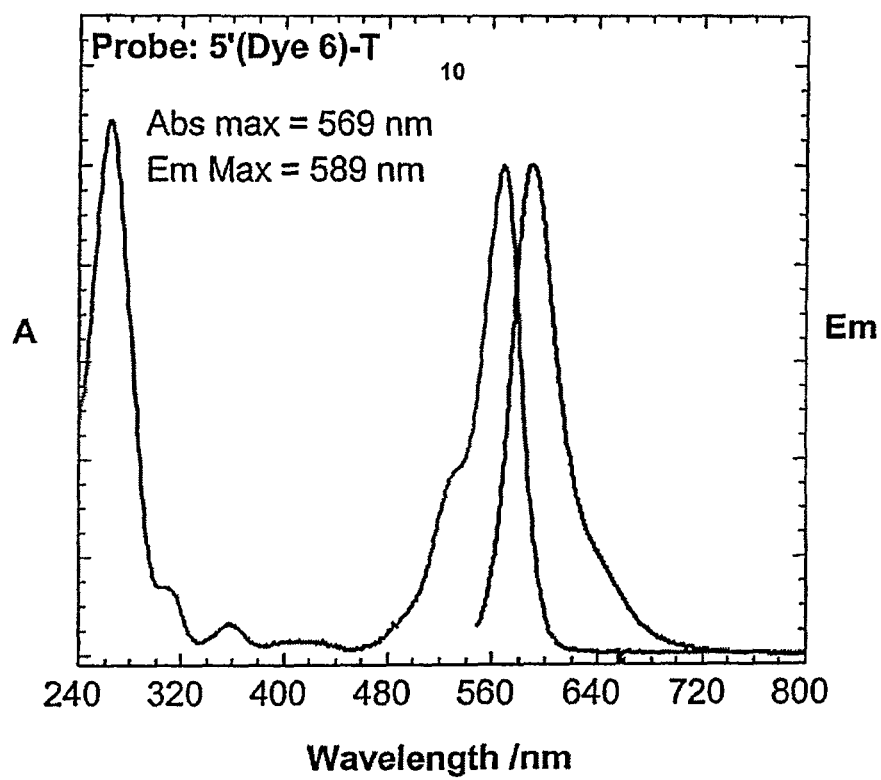
FIG. 12 is an overlay of absorption and emission spectra of 5'-TTTTTTTTTT-3' 5' labeled with 6.
Figure 13:
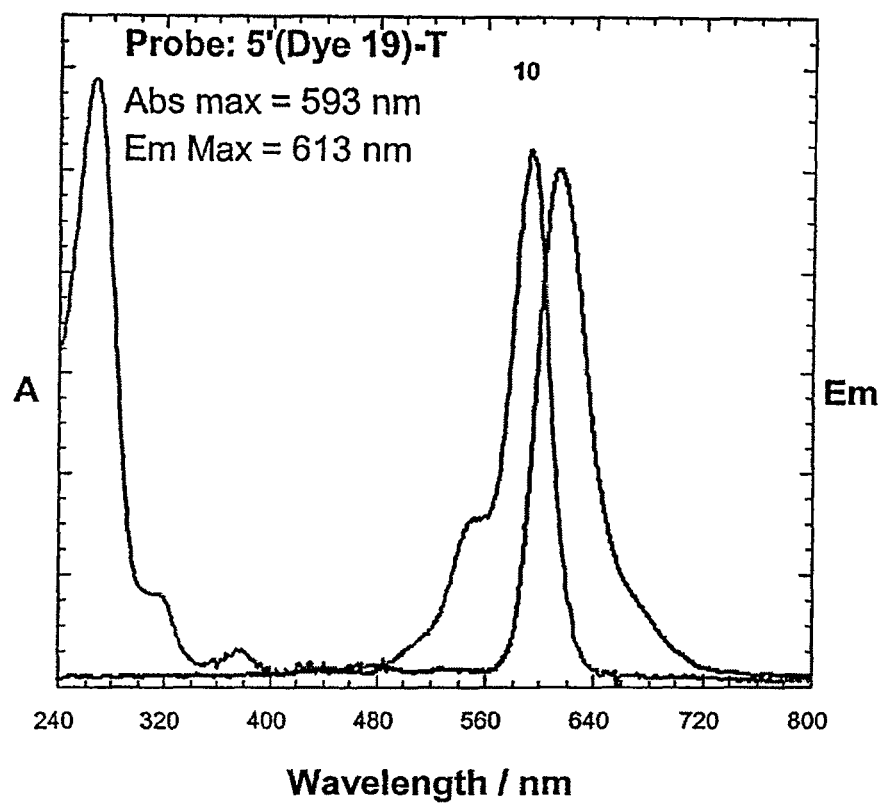
FIG. 13 is an overlay of absorption and emission spectra of 5'-TTTTTTTTTT-3' 5' labeled with 19.

For example, FIG. 2 is a reverse phase HPLC trace of a conjugate between the nucleic acid and 15, showing the purity of the conjugate. The mass spectrum, which shows a peak corresponding to the conjugate (M/e 5214), is shown in FIG. 3. FIG. 4 is an anion exchange HPLC chromatogram of a conjugate between the nucleic acid and 25. The mass spectrum (FIG. 5) of the nucleic acid conjugate with 25 includes a major peak at M/e 5128, corresponding to the conjugate. The reverse-phase HPLC chromatogram of the conjugate between the nucleic acid and 19 is shown in FIG. 6. A mass spectrum of this conjugate has a peak (M/e 5304) corresponding to the molecular weight of the conjugate (FIG. 7). The anion exchange chromatogram of the conjugate between the nucleic acid and 3'-OH linked 28 is shown in FIG. 8 and the mass spectrum in FIG. 9.

The absorption and emission profiles of conjugates of the xanthenes of the invention 25, 15, 6 and 19 and a model nucleic acid (TTTTTTTTTT) are shown in FIG. 10, FIG. 11, FIG. 12, FIG. 13, respectively.

Chemical synthesis of the nucleic acid is generally automated and it is performed by coupling nucleosides through phosphorus-containing covalent linkages. The most commonly used oligonucleotide synthesis method involves reacting a nucleoside with a protected cyanoethyl phosphoramidite monomer in the presence of a weak acid. The coupling step is followed by oxidation of the resulting phosphite linkage. Finally, the cyanoethyl protecting group is removed and the nucleic acid is cleaved from the solid support on which it was synthesized. The labels of the present invention can be incorporated during oligonucleotide synthesis using a phosphoramidite derivative of the fluorescent compound of the invention. Alternatively, the label can be introduced by combining a compound of the invention that includes a reactive functional group with the nucleic acid under appropriate conditions to couple the compound to the nucleic acid. In yet another embodiment, the fluorescent compound is attached to a solid support through a linker arm, such as a substituted or unsubstituted alkyl, substituted or unsubstituted heteroalkyl or a nucleic acid residue. Synthesis proceeds with the fluorescent moiety already in place on the growing nucleic acid chain.

Enzymatic methods of synthesis involve the use of fluorescent-labeled nucleic acids in conjunction with a nucleic acid template, a primer and an enzyme. Efficient enzymatic incorporation of a fluorescent-labeled nucleic acid is facilitated by selection of reaction partners that do not adversely affect the enzymes ability to couple the partners.

In those embodiments of the invention in which the xanthene-based fluorescent compound of the invention is attached to a nucleic acid, the carrier molecule is produced by either synthetic (solid phase, liquid phase or a combination) or enzymatically, or by a combination of these processes. One synthetic strategy for the preparation of oligonucleotides is the H-phosphonate method (Froehler, B. and Matteucci, M. (1986) *Tetrahedron Lett.*, (27): 469-472). This method utilizes activated nucleoside H-phosphonate monomers rather than phosphoramidites to create the phosphate internucleotide linkage. In contrast to the phosphoramidite method, the resulting phosphonate linkage does not require oxidation every cycle but instead only a single oxidation step at the end of chain assembly. The H-phosphonate method may also be used to conjugate reporters and dyes to synthetic oligonucleotide chains (Sinha, N. and Cook, R. (1988) *Nucleic Acids Research*, (16): 2659).

The four bases of the nucleosides, adenine, thymine (uracil in RNA), guanine and cytosine include moieties that are chemically reactive (e.g., exocyclic amines) and must be protected from participating in undesirable reactions during the synthesis of the oligonucleotide by "blocking" the reactive sites with a moiety that can be removed once the synthesis is complete. Traditional protecting groups include the benzoyl (dA, dC) and isobutyryl (dC, dG) groups. Each of the aforementioned protecting groups is base-labile and is typically cleaved, with concomitant cleavage of the oligonucleotide from the synthesis support, using ammonia/water mixtures. A full review of protecting groups may be found in "Advances in the Synthesis of Oligonucleotides by the Phosphoramidite Approach", Tetrahedron Vol 48, p 2223-2311, 1992).

In another exemplary embodiment, the invention provides a method of deprotecting a conjugate formed between a xanthene dye of the invention and a nucleic acid. The method consists of contacting a precursor to the conjugate in which the nucleic acid monomers are protected with a deprotection cocktail that includes an amine and alcohol. It has been discovered that use the deprotection cocktail with the conjugates of the invention significantly enhances the yield of the deprotected conjugate, minimizing degradation of the xanthene dye during deprotection.

The oligonucleotide may be cleaved from the solid support before deprotection, after deprotection or concomitant with deprotection. Thus, in another embodiment, the oligonucleotide is tethered to a solid support via a linker arm that is not cleaved by the organic amine that removes the base-labile protecting group. In this embodiment, the oligonucleotide may be cleaved from the support using a reagent other than the deprotection reagent. Thus, the method of the invention further includes the step of contacting the support-bound oligonucleotide with a cleavage reagent, thereby forming a cleavage mixture, and incubating the cleavage mixture for a period of time sufficient to cleave the oligonucleotide from the support.

The superior flexibility of the method of the invention allows virtually any primary or secondary organic amine to be of use as the deprotecting agent. The amines set forth below are merely exemplary, and those of skill will appreciate that the invention is not limited to the use of the explicitly recited amines. Amines of use in practicing the present invention include substituted or unsubstituted alkyl amines, substituted or unsubstituted aryl amines, substituted or unsubstituted heteroaryl amines and substituted or unsubstituted heterocyclic amines.

Also useful in the method of the invention are the alkyl amino alcohols, e.g., aminoethanol, aminopropanol, 2-amino-2-methyl-1-propanol and combinations thereof. Alkyl amino ethers, e.g., 1,4-butanediol-bis-(3-aminopropyl) ether, 4,7,10-trioxa-1,13-tridecanamine and combinations thereof can also be used. The amine may also be a polymeric amine, e.g, poly(ethyleneimine), poly(ethylene glycol)amine and combinations thereof. Other amines and combinations of amines will be apparent to those of skill in the art.

Reactive Functional Groups

The compounds of the invention bear a reactive functional group, which can be located at any position on the molecule. Exemplary species include a reactive functional group as a constituent of at least one of $R^{12}$ and $R^{13}$. Exemplary reactive groups are members independently selected from substituted or unsubstituted alkyl, substituted or unsubstituted heteroalkyl, substituted or unsubstituted heterocycloalkyl, substituted or unsubstituted aryl and substituted or unsubstituted heteroaryl, with the proviso that at least one of $R^{12}$ or $R^{13}$ includes an oxygen-containing reactive group or a carrier molecule. When the reactive group is attached a substituted or unsubstituted alkyl or substituted or unsubstituted heteroalkyl moiety, the reactive group is preferably located at a terminal position of the alkyl or heteroalkyl chain. Reactive groups and classes of reactions useful in practicing the present invention are generally those that are well known in the art of bioconjugate chemistry. Currently favored classes of reactions available with reactive xanthene-based compounds of the invention are those proceeding under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups include, for example:

(a) carboxyl groups and derivatives thereof including, but not limited to activated esters, e.g., N-hydroxysuccinimide esters, N-hydroxybenztriazole esters, acid halides, acyl imidazoles, thioesters, p-nitrophenyl esters, alkyl, alkenyl, alkynyl and aromatic esters, activating groups used in peptide synthesis and acid halides;

(b) hydroxyl groups, which can be converted to esters, sulfonates, phosphoramidates, ethers, aldehydes, etc.

(c) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups, which are capable of participating in Diels-Alder reactions such as, for example, maleimido groups;

(e) aldehyde or ketone groups, allowing derivatization via formation of carbonyl derivatives, e.g., imines, hydrazones, semicarbazones or oximes, or via such mechanisms as Grignard addition or alkyllithium addition;

(f) sulfonyl halide groups for reaction with amines, for example, to form sulfonamides;

(g) thiol groups, which can be converted to disulfides or reacted with acyl halides, for example;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds; and (k) phosphoramidites and other standard functional groups useful in nucleic acid synthesis.

The reactive functional groups can be chosen such that they do not participate in, or interfere with, the reactions necessary to assemble or utilize the reactive xanthene analogue. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

In addition to those embodiments in which a compound of the invention is attached directly to a carrier molecule, the fluorophores can also be attached by indirect means. In this embodiment, a ligand molecule (e.g., biotin) is generally covalently bound to the probe species. The ligand then binds to another molecules (e.g., streptavidin) molecule, which is either inherently detectable or covalently bound to a signal system, such as a fluorescent compound, or an enzyme that produces a fluorescent compound by conversion of a non-fluorescent compound. Useful enzymes of interest as labels include, for example, hydrolases, particularly phosphatases, esterases and glycosidases, hydrolases, peptidases or oxidases, and peroxidases.

Probes

The invention provides probes having a xanthene dye of the invention conjugated to a carrier molecule, for example, a target species (e.g., receptor, enzyme, etc.) a ligand for a target species (e.g., nucleic acid, peptide, etc.), a small molecule (e.g., drug, pesticide, etc.), a solid support and the like. The probes can be used for in vitro and in vivo applications.

An unexpected property of the xanthene dyes of the invention is their robustness under a variety of synthetic conditions used to attach the xanthene dye of the invention to a carrier molecule. For example, many of the xanthene dyes of the invention survive the conditions necessary for automated synthesis of nucleic acids without undergoing any substantial degree of degradation or alteration. In contrast, many of art-recognized fluorophores presently in use require the use of special conditions to assemble the carrier molecule to which they are attached, or they have to be attached after the completion of the carrier molecule synthesis. The additional complexity of the synthesis of a probe increases both the duration of the synthesis and its cost.

Dual Labeled Probes

The present invention also provides dual labeled probes that include both a xanthene dye of the invention and second label. Exemplary second labels include quenchers of fluorescence energy, such as that emitted by the xanthene dyes of the invention. Quenchers of use in the dual labeled probes of the invention are known to those of skill in the art. See, for example, commonly owned PCT application U.S. 01/15082 disclosing, "Black Hole" quenchers. A preferred quencher for use with the xanthenes of the invention comprises a diazo bond between two radicals independently selected from substituted or unsubstituted aryl and substituted or unsubstituted heteroaryl groups. The quencher is generally conjugated to the xanthene or to a linker attached to the xanthene.

The dual labeled probes include a first and a second probe attached to a structure linking the two labels. Of note are linkers that are biomolecules, e.g., nucleic acids, peptides, lipids, saccharides and the like; drug moieties; substituted and unsubstituted alkyl, substituted and unsubstituted heteroalkyl, substituted and unsubstituted aryl, substituted and unsubstituted heteroaryl and substituted and unsubstituted heterocycloalkyl moieties. Selected linkers of use with the xanthenes of the invention are discussed in greater detail herein.

Exemplary dual labeled probes include nucleic acid probes that include a nucleic acid with a xanthene dye of the invention attached thereto. Exemplary probes include both a xanthene dye of the invention and a quencher. The probes are of use in a variety of assay formats. For example, when a nucleic acid singly labeled with a xanthene dye of the invention is the probe, the interaction between the first and second nucleic acids can be detected by observing the interaction between the xanthene dye of the invention and the nucleic acid. Alternatively, the interaction is the quenching by a quencher attached to the second nucleic acid of the fluorescence from a xanthene dye of the invention.

The xanthene dyes of the invention are useful in conjunction with nucleic-acid probes in a variety of nucleic acid amplification/quantification strategies including, for example, 5'-nuclease assay, Strand Displacement Amplification (SDA), Nucleic Acid Sequence-Based Amplification (NASBA), Rolling Circle Amplification (RCA), as well as for direct detection of targets in solution phase or solid phase (e.g., array) assays. Furthermore, the xanthene dye of the invention-derivatized nucleic acids can be used in probes of substantially any format, including, for example, format selected from molecular beacons, Scorpion Probes™, Sunrise Probes™, conformationally assisted probes, light up probes, Invader Detection probes, and TaqMan™ probes. See, for example, Cardullo, R., et al., *Proc. Natl. Acad. Sci. USA*, 85:8790-8794 (1988); Dexter, D. L., *J. Chem. Physics*, 21:836-850 (1953); Hochstrasser, R. A., et al., *Biophysical Chemistry*, 45:133-141 (1992); Selvin, P., *Methods in Enzymology*, 246:300-334 (1995); Steinberg, I., *Ann. Rev. Biochem.*, 40:83-114 (1971); Stryer, L., *Ann. Rev. Biochem.*, 47:819-846 (1978); Wang, G., et al., *Tetrahedron Letters*, 31:6493-6496 (1990); Wang, Y., et al., *Anal. Chem.*, 67:1197-1203 (1995); Debouck, C., et al., in supplement to *nature genetics*, 21:48-50 (1999); Rehman, F. N., et al., *Nucleic Acids Research*, 27:649-655 (1999); Cooper, J. P., et al., *Biochemistry*, 29:9261-9268 (1990); Gibson, E. M., et al., *Genome Methods*, 6:995-1001 (1996); Hochstrasser, R. A., et al., *Biophysical Chemistry*, 45:133-141 (1992); Holland, P. M., et al., *Proc Natl. Acad. Sci USA*, 88:7276-7289 (1991); Lee, L. G., et al., *Nucleic Acids Rsch.*, 21:3761-3766 (1993); Livak, K. J., et al., *PCR Methods and Applications*, Cold Spring Harbor Press (1995); Vamosi, G., et al., *Biophysical Journal*, 71:972-994 (1996); Wittwer, C. T., et al., *Biotechniques*, 22:176-181 (1997); Wittwer, C. T., et al., *Biotechniques*, 22:130-38 (1997); Giesendorf, B. A. J., et al., *Clinical Chemistry*, 44:482-486 (1998); Kostrikis, L. G., et al., *Science*, 279:1228-1229 (1998); Matsuo, T., *Biochemica et Biophysica Acta*, 1379:178-184 (1998); Piatek, A. S., et al., *Nature Biotechnology*, 16:359-363 (1998); Schofield, P., et al., *Appl. Environ. Microbiology*, 63:1143-1147 (1997); Tyagi S., et al., *Nature Biotechnology*, 16:49-53 (1998); Tyagi, S., et al., *Nature Biotechnology*, 14:303-308 (1996); Nazarenko, I. A., et al., *Nucleic Acids Research*, 25:2516-2521 (1997); Uehara, H., et al., *Biotechniques*, 26:552-558 (1999); D. Whitcombe, et al., *Nature Biotechnology*, 17:804-807 (1999); Lyamichev, V., et al., *Nature Biotechnology*, 17:292 (1999); Daubendiek, et al., *Nature Biotechnology*, 15:273-277 (1997); Lizardi, P. M., et al., *Nature Genetics*, 19:225-232 (1998); Walker, G., et al., *Nucleic Acids Res.*, 20:1691-1696 (1992); Walker, G. T., et al., *Clinical Chemistry*, 42:9-13 (1996); and Compton, J., *Nature*, 350:91-92 (1991).

In view of the well-developed body of literature concerning the conjugation of small molecules to nucleic acids, many other methods of attaching donor/acceptor pairs to nucleic acids will be apparent to those of skill in the art.

More specifically, there are many linking moieties and methodologies for attaching groups to the 5'- or 3'-termini of nucleic acids, as exemplified by the following references: Eckstein, editor, Nucleic acids and Analogues: A Practical Approach (IRL Press, Oxford, 1991); Zuckerman et al., *Nucleic Acids Research*, 15: 5305-5321 (1987) (3'-thiol group on nucleic acid); Sharma et al., *Nucleic Acids*

Research, 19: 3019 (1991) (3'-sulfhydryl); Giusti et al., PCR Methods and Applications, 2: 223-227 (1993) and Fung et al., U.S. Pat. No. 4,757,141 (5'-phosphoamino group via Aminolink™ II available from P.E. Biosystems, CA.) Stabinsky, U.S. Pat. No. 4,739,044 (3-aminoalkylphosphoryl group); Agrawal et al., Tetrahedron Letters, 31: 1543-1546 (1990) (attachment via phosphoramidate linkages); Sproat et al., Nucleic Acids Research, 15: 4837 (1987) (5-mercapto group); Nelson et al., Nucleic Acids Research, 17: 7187-7194 (1989) (3'-amino group), and the like. Methods for attaching the dyes to other nucleic acid moieties, e.g., internucleotide bridges, sugar C-atoms, nucleobase atoms, etc. are known to those of skill in the art.

Exemplary fluorophores that can be combined in a probe with a xanthene dye of the invention include those set forth in Table 1.

TABLE 1

Suitable moieties that can be selected as donors or acceptors in donor-acceptor energy transfer pairs 4-acetamido-4'-isothiocyanatostilbene-2,2'disulfonic acid
acridine and derivatives:
    acridine
    acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin and derivatives:
coumarin
    7-amino-4-methylcoumarin (AMC, Coumarin 120)
    7-amino-4-trifluoromethylcouluarin (Coumaran 151)
xanthene dyes
cyanosine
4',6-diaminidino-2-phenylindole (DAPI)
5',5"-dibromopyrogallol-sulfonaphthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[diN-methylamino]naphthalene-1-sulfonyl chloride
(DNS, dansylchloride)
4-(4'-diN-methylaminophenylazo)benzoic acid (DABCYL)
4-diN-methylaminophenylazophenyl-4'-isothiocyanate (DABITC)
eosin and derivatives:
    eosin
    eosin isothiocyanate
erythrosin and derivatives:
    erythrosin B
    erythrosin isothiocyanate
ethidium
fluorescein and derivatives:
    5-carboxyfluorescein (FAM)
    5-(4,6-dichlorotriazin-2-yl)aminofluorescein (DTAF)
    2',7'-dimethoxy-4'5'-dichloro-6-carboxyfluorescein (JOE)
    fluorescein
    fluorescein isothiocyanate
    QFITC (XRITC)
fluorescamine
IR144
IR1446
Malachite Green isothiocyanate
4-methylumbelliferone
ortho cresolphthalein
nitrotyrosine
pararosaniline
Phenol Red
B-phycoerythrin
o-phthaldialdehyde TABLE 1-continued Suitable moieties that can be selected as donors or acceptors in donor-acceptor energy transfer pairs pyrene and derivatives:
    pyrene
    pyrene butyrate
    succinimidyl 1-pyrene butyrate
quantum dots
Reactive Red 4 (Cibacron ™ Brilliant Red 3B-A)
rhodamine and derivatives:
    6-carboxy-X-rhodamine (ROX)
    6-carboxyrhodamine (R6G)
    lissamine rhodamine B sulfonyl chloride rhodamine (Rhod)
    rhodamine B
    rhodamine 123
    rhodamine X isothiocyanate
    sulforhodamine B
    sulforhodamine 101
sulfonyl chloride derivative of sulforhodamine 101 (Texas Red)
N,N,N',N'-tetramethyl-6-carboxyrhodamine (TAMRA)
tetramethyl rhodamine
    tetramethyl rhodamine isothiocyanate (TRITC)
riboflavin
rosolic acid
terbium chelate derivatives There is a great deal of practical guidance available in the literature for selecting appropriate donor-acceptor pairs for particular probes, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent and chromogenic molecules and their relevant optical properties for choosing reporter-quencher pairs (see, for example, Berlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via common reactive groups that can be added to a nucleic acid, as exemplified by the following references: Haugland (supra); Ullman et al., U.S. Pat. No. 3,996,345; Khanna et al., U.S. Pat. No. 4,351,760. Thus, it is well within the abilities of those of skill in the art to choose an energy exchange pair for a particular application and to conjugate the members of this pair to a probe molecule, such as, for example, a nucleic acid, peptide or other polymer.

As will be apparent to those of skill in the art the methods set forth above are equally applicable to the coupling to a nucleic acid of groups other than the fluorescent compounds of the invention, e.g., quenchers, intercalating agents, hybridization enhancing moieties, minor groove binders, alkylating agents, cleaving agents, etc.

For example, in selected embodiments, the probe includes a metal chelate or a chelating agent attached to the carrier molecule. The use of these compounds to bind to specific compounds is well known to those of skill in the art. See, for example, Pitt et al. "The Design of Chelating Agents for the Treatment of Iron Overload," In, INORGANIC CHEMISTRY IN BIOLOGY AND MEDICINE; Martell, A. E., Ed.; American Chemical Society, Washington, D.C., 1980, pp. 279-312; Lindoy, L. F., THE CHEMISTRY OF MACROCYCLIC LIGAND COMPLEXES; Cambridge University Press, Cambridge, 1989; Dugas, H., BIOORGANIC CHEMISTRY; Springer-Verlag, New York, 1989, and references contained therein.

Additionally, a manifold of routes allowing the attachment of chelating agents, crown ethers and cyclodextrins to other molecules is available to those of skill in the art. See, for example, Meares et al., "Properties of In Vivo Chelate-Tagged Proteins and Polypeptides." In, MODIFICATION OF PROTEINS: FOOD, NUTRITIONAL, AND PHARMACOLOGICAL ASPECTS;" Feeney, R. E., Whitaker, J. R., Eds., American Chemical Society, Washington, D.C., 1982, pp. 370-387; Kasina et al. *Bioconjugate Chem.* 9:108-117 (1998); Song et al., *Bioconjugate Chem.* 8:249-255 (1997).

In a presently preferred embodiment, the chelating agent is a polyaminocarboxylate chelating agent such as ethylenediaminetetraacetic acid (EDTA) or diethylenetriaminepentaacetic acid (DTPA). These chelating agents can be attached to any amine-terminated component of a carrier molecule or a spacer arm, for example, by utilizing the commercially available dianhydride (Aldrich Chemical Co., Milwaukee, Wis.).

The nucleic acids for use in the probes of the invention can be any suitable size, and are preferably in the range of from about 10 to about 100 nucleotides, more preferably from about 10 to about 80 nucleotides and more preferably still, from about 20 to about 40 nucleotides. The precise sequence and length of a nucleic acid probe of the invention depends in part on the nature of the target polynucleotide to which it binds. The binding location and length may be varied to achieve appropriate annealing and melting properties for a particular embodiment. Guidance for making such design choices can be found in many art-recognized references.

Preferably, the 3'-terminal nucleotide of the nucleic acid probe is blocked or rendered incapable of extension by a nucleic acid polymerase. Such blocking is conveniently carried out by the attachment of a donor or acceptor moiety to the terminal 3'-position of the nucleic acid probe, either directly or by a linking moiety.

The nucleic acid can comprise DNA, RNA or chimeric mixtures or derivatives or modified versions thereof. Both the probe and target nucleic acid can be present as a single strand, duplex, triplex, etc. Moreover, as discussed above, the nucleic acid can be modified at the base moiety, sugar moiety, or phosphate backbone with other groups such as radioactive labels, minor groove binders, intercalating agents, donor and/or acceptor moieties and the like.

For example, the nucleic acid can comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxyN-methylaminomethyl-2-thiouridine, 5-carboxy-N-methylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-adenine, 7-methylguanine, 5-N-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, nitroindole, and 2,6-diaminopurine. The xanthene dye of the invention or another probe component can be attached to the modified base.

In another embodiment, the nucleic acid comprises at least one modified sugar moiety selected from the group including, but not limited to, arabinose, 2-fluoroarabinose, xylulose, and hexose. The xanthene dye or another probe component can be attached to the modified sugar moiety.

In yet another embodiment, the nucleic acid comprises at least one modified phosphate backbone selected from the group including, but not limited to, a peptide nucleic acid hybrid, a phosphorothioate, a phosphorodithioate, a phosphoramidothioate, a phosphoramidate, a phosphordiamidate, a methylphosphonate, an alkyl phosphotriester, and a formacetal or analog thereof. The xanthene dye or another probe component can be attached to the modified phosphate backbone.

Phosphodiester linked nucleic acids of the invention can be synthesized by standard methods known in the art, e.g. by use of an automated DNA synthesizer using commercially available amidite chemistries (Ozaki et al., *Nucleic Acids Research*, 20: 5205-5214 (1992); Agrawal et al., *Nucleic Acids Research*, 18: 5419-5423 (1990); Beaucage et al., *Tetrahedron*, 48: 2223-2311 (1992); Molko et al., U.S. Pat. No. 4,980,460; Koster et al., U.S. Pat. No. 4,725,677; Caruthers et al., U.S. Pat. Nos. 4,415,732; 4,458,066; and 4,973,679). Nucleic acids bearing modified phosphodiester linking groups can be synthesized by methods known in the art. For example, phosphorothioate nucleic acids may be synthesized by the method of Stein et al. (*Nucl. Acids Res.* 16:3209 (1988)), methylphosphonate nucleic acids can be prepared by use of controlled pore glass polymer supports (Sarin et al., *Proc. Natl. Acad. Sci. U.S.A.* 85:7448-7451 (1988)). Other methods of synthesizing both phosphodiester- and modified phosphodiester-linked nucleic acids will be apparent to those of skill in the art.

When the nucleic acids are synthesized utilizing an automated nucleic acid synthesizer, the donor and acceptor moieties are preferably introduced during automated synthesis. Alternatively, one or more of these moieties can be introduced either before or after the automated synthesis procedure has commenced. For example, donor and/or acceptor groups can be introduced at the 3'-terminus using a solid support modified with the desired group(s). Additionally, donor and/or acceptor groups can be introduced at the 5'-terminus by, for example a derivative of the group that includes a phosphoramidite. In another exemplary embodiment, one or more of the donor and/or acceptor groups is introduced after the automated synthesis is complete.

In the dual labeled probes, the quencher moiety is preferably separated from the xanthene dye of the invention by at least about 6 nucleotides, more preferably at least about 10 nucleotides, and more preferably by at least about 15 nucleotides. The quencher moiety is preferably attached to either the 3'- or 5'-terminal nucleotides of the probe. The xanthene dye of the invention moiety is also preferably attached to either the 3'- or 5'-terminal nucleotides of the probe. More preferably, the donor and acceptor moieties are attached to the 3'- and 5'- or 5'- and 3'-terminal nucleotides of the probe, respectively, although internal placement is also useful.

Once the desired nucleic acid is synthesized, it is preferably cleaved from the solid support on which it was synthesized and treated, by methods known in the art, to remove any protecting groups present (e.g., 60° C., 5h, concentrated ammonia). In those embodiments in which a base-sensitive group is attached to the nucleic acids (e.g., TAMRA), the deprotection will preferably use milder conditions (e.g., butylamine:water 1:3, 8 hours, 70° C.). Deprotection under these conditions is facilitated by the use of quick deprotect amidites (e.g., dC-acetyl, dG-dmf). An alternative work up utilizes 2-methoxyethylamine and methanol.

Following cleavage from the support and deprotection, the nucleic acid is purified by any method known in the art, including chromatography, extraction and gel purification. In a preferred embodiment, the nucleic acid is purified using HPLC. The concentration and purity of the isolated nucleic acid is preferably determined by measuring the optical density at 260 nm in a spectrophotometer.

Exemplary dual labeled probes of the invention were prepared as described in the Examples section.

Small Molecule Probes

The xanthene dyes of the invention can be used as components of small molecule probes. In a preferred design, a small molecule probe includes a xanthene dye of the invention and a second species that alters the luminescent properties of the dyes, e.g., a quencher of fluorescence. In an exemplary embodiment, an agent such as an enzyme cleaves the xanthene dye of the invention, the quencher or both from the small molecule generating fluorescence in the system under investigation (see, for example, Zlokarnik et al., Science 279: 84-88 (1998)).

Nucleic Acid Capture Probes

In one embodiment, an immobilized nucleic acid comprising a xanthene dye of the invention is used as a capture probe. The nucleic acid probe can be used in solution phase or it can be attached to a solid support. The immobilized probes can be attached directly to the solid support or through a linker arm between the support and the xanthene dye or between the support and a nucleic acid residue. Preferably, the probe is attached to the solid support by a linker (i.e., spacer arm, supra). The linker serves to distance the probe from the solid support. The linker is most preferably from about 5 to about 30 atoms in length, more preferably from about 10 to about 50 atoms in length. Exemplary attachment points include the 3'- or 5'-terminal nucleotide of the probe as well as other accessible sites discussed herein.

In yet another preferred embodiment, the solid support is also used as the synthesis support in preparing the probe. The length and chemical stability of the linker between the solid support and the first 3'-unit of nucleic acid (or the xanthene dye) play an important role in efficient synthesis and hybridization of support bound nucleic acids. The linker arm should be sufficiently long so that a high yield (>97%) can be achieved during automated synthesis. The required length of the linker will depend on the particular solid support used. Exemplary linkers are from about 6 to about 30 atoms in length. For nucleic acid synthesis, the linker arm is usually attached to the 3'-OH of the 3'-terminus by a cleaveable linkage, e.g., an ester linkage, which can be cleaved with appropriate reagents to free the nucleic acid from the solid support.

Hybridization of a probe immobilized on a solid support generally requires that the probe be separated from the solid support. A preferred linker for this embodiment includes at least about 20 atoms, more preferably at least about 50 atoms.

A wide variety of linkers are known in the art, which may be used to attach the nucleic acid probe to the solid support. The linker may include an oligomer or polymer of any moiety or combination of moieties, which does not significantly interfere with the hybridization of the target sequence to the probe attached to the solid support. The linker may include a nucleic acid, for example, a homopolymeric nucleic acid, which can be readily added on to the linker by automated synthesis. Alternatively, polymers such as polyethylene glycol can be used as the linker. Such polymers are presently preferred over homopolymeric nucleic acids because they do not significantly interfere with the hybridization of probe to the target nucleic acid. Polyethylene glycol is particularly preferred because it is commercially available, soluble in both organic and aqueous media, easy to functionalize, and completely stable under nucleic acid synthesis and post-synthesis conditions.

The linkages between the solid support, the linker and the probe are preferably not cleaved during synthesis or removal of base protecting groups under basic conditions at high temperature. These linkages can, however, be selected from groups that are cleavable under a variety of conditions. Examples of presently preferred linkages include carbamate, ester and amide linkages.

Peptide Probes

Peptides, proteins and peptide nucleic acids that are labeled with a quencher and a xanthene dye of the invention can be used in both in vivo and in vitro enzymatic assays.

Peptide constructs useful in practicing the invention include those with the following features: i) a quencher; ii) a xanthene dye of the invention; and iii) a cleavage or assembly recognition site for the enzyme. Moreover, the peptide construct is preferably exists in at least one conformation that allows donor-acceptor energy transfer between the xanthene dye of the invention and the quencher when the fluorophore is excited.

In the dual labeled probes of the invention, the donor and acceptor moieties are connected through an intervening linker moiety. The linker moiety, preferably, includes a peptide moiety, but can be or can include another organic molecular moiety, as well. In a preferred embodiment, the linker moiety includes a cleavage recognition site specific for an enzyme or other cleavage agent of interest. A cleavage site in the linker moiety is useful because when a tandem construct is mixed with the cleavage agent, the linker is a substrate for cleavage by the cleavage agent. Rupture of the linker moiety results in separation of the xanthene dye and the quencher. The separation is measurable as a change in donor-acceptor energy transfer. Alternatively, peptide assembly can be detected by an increase in donor-acceptor energy transfer between a peptide fragment bearing a xanthene dye of the invention and a peptide fragment bearing a donor moiety.

When the cleavage agent of interest is a protease, the linker generally includes a peptide containing a cleavage recognition sequence for the protease. A cleavage recognition sequence for a protease is a specific amino acid sequence recognized by the protease during proteolytic cleavage. Many protease cleavage sites are known in the art, and these and other cleavage sites can be included in the linker moiety. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); Bouvier et al. *Meth. Enzymol.* 248: 614 (1995), Hardy et al., in AMYLOID PROTEIN PRECURSOR IN DEVELOPMENT, AGING, AND ALZHEIMER'S DISEASE, ed. Masters et al. pp. 190-198 (1994).

Solid Support Immobilized Xanthene Dye Analogues

The xanthene dyes of the invention can be immobilized on substantially any polymer, biomolecule, or solid or semi-solid material having any useful configuration. Moreover, any conjugate comprising one or more xanthene dye of the invention can be similarly immobilized, through a moiety on either the xanthene or its conjugation partner. When the support is a solid or semi-solid, exemplary supports for immobilization of the nucleic acid probe include controlled pore glass, glass plates, polystyrene, avidin coated polystyrene beads, cellulose, nylon, acrylamide gel and activated dextran. These solid supports are chemically stable, easily functionalized and have a well-defined surface area.

Solid supports such as, controlled pore glass (CPG, 500 Å, 1000 Å) and non-swelling high cross-linked polystyrene (1000 Å) are exemplary preferred supports.

According to the present invention, the surface of a solid support is functionalized with a xanthene dye of the invention or a species, e.g., a linker or conjugation partner, to which a xanthene dye of the invention is conjugated. For clarity of illustration, the following discussion focuses on attaching a reactive xanthene dye of the invention to a solid support. The following discussion is also broadly relevant to attaching to a solid support a species that includes within its structure a xanthene dye of the invention.

The xanthene dyes of the invention are preferably attached to a solid support by forming a bond between a reactive group on the xanthene dye of the invention and a reactive group on the surface of the solid support, thereby derivatizing the solid support with one or more xanthene dyes of the invention. Alternatively, the reactive group on the xanthene dye of the invention is coupled with a reactive group on a linker arm attached to the solid support. The bond between the solid support and the xanthene dye of the invention is preferably a covalent bond, although ionic, dative and other such bonds are useful as well. Reactive groups which can be used in practicing the present invention are discussed in detail above and include, for example, amines, hydroxyl groups, carboxylic acids, carboxylic acid derivatives, alkenes, sulfhydryls, siloxanes, etc.

A large number of solid supports appropriate for practicing the present invention are available commercially and include, for example, peptide synthesis resins, both with and without attached amino acids and/or peptides (e.g., alkoxybenzyl alcohol resin, aminomethyl resin, aminopolystyrene resin, benzhydrylamine resin, etc. (Bachem)), functionalized controlled pore glass (BioSearch Technologies, Inc.), ion exchange media (Aldrich), functionalized membranes (e.g., —COOH membranes; Asahi Chemical Co., Asahi Glass Co., and Tokuyama Soda Co.), and the like.

Moreover, for applications in which an appropriate solid support is not commercially available, a wide variety of reaction types are available for the functionalization of a solid support surface. For example, supports constructed of a plastic such as polypropylene, can be surface derivatized by chromic acid oxidation, and subsequently converted to hydroxylated or aminomethylated surfaces. The functionalized support is then reacted with a xanthene dye of the invention of complementary reactivity, such as a xanthene dye of the invention active ester, acid chloride or sulfonate ester, for example. Supports made from highly crosslinked divinylbenzene can be surface derivatized by chloromethylation and subsequent functional group manipulation. Additionally, functionalized substrates can be made from etched, reduced polytetrafluoroethylene.

When the support is constructed of a siliceous material, such as glass, the surface can be derivatized by reacting the surface Si—OH, SiO—H, and/or Si—Si groups with a functionalizing reagent.

In a preferred embodiment, wherein the substrates are made from glass, the covalent bonding of the reactive group to the glass surface is achieved by conversion of groups on the substrate's surface by a silicon-modifying reagent such as:

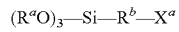

where $R^a$ is an alkyl group, such as methyl or ethyl, $R^b$ is a linking group between silicon and $X^a$, and $X^a$ is a reactive group or a protected reactive group. Silane derivatives having halogens or other leaving groups beside the displayed alkoxy groups are also useful in the present invention. Exemplary linking groups include those that include substituted or unsubstituted alkyl and substituted or unsubstituted heteroalkyl groups.

In another preferred embodiment, the reagent used to functionalize the solid support provides for more than one reactive group per each reagent molecule. Using reagents, such as the compound below, each reactive site on the substrate surface is, in essence, "amplified" to two or more functional groups:

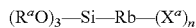

where $R^a$ is an alkyl group (e.g., methyl, ethyl), $R^b$ is a linking group between silicon and $X^a$, $X^a$ is a reactive group or a protected reactive group and n is an integer between 2 and 50, and more preferably between 2 and 20. The amplification of a xanthene dye of the invention by its attachment to a silicon-containing substrate is intended to be exemplary of the general concept of amplification. This amplification strategy is equally applicable to other aspects of the invention in which a xanthene dye of the invention is attached to another molecule or solid support.

A number of siloxane functionalizing reagents can be used, for example:

1. Hydroxyalkyl siloxanes (Silylate surface, functionalize with diborane, and $H_2O_2$ to oxidize to the alcohol)
  a. allyl trichlorosilane→→3-hydroxypropyl
  b. 7-oct-1-enyl trichlorchlorosilane→→8-hydroxyoctyl;
2. Diol (dihydroxyalkyl) siloxanes (silylate surface and hydrolyze to diol)
  a. (glycidyl trimethoxysilane→(2,3-dihydroxypropyloxy) propyl;
3. Aminoalkyl siloxanes (amines requiring no intermediate functionalizing step);
  a. 3-aminopropyl trimethoxysilane→aminopropyl Dimeric secondary aminoalkyl siloxanes;
  b. bis(3-trimethoxysilylpropyl)amine→bis(silyloxylpropyl)amine.

It will be apparent to those of skill in the art that an array of similarly useful functionalizing chemistries is available when support components other than siloxanes are used. Thus, for example alkyl thiols (e.g., self-assembled monolayers), functionalized as discussed above in the context of siloxane-modifying reagents, can be attached to metal films and subsequently reacted with a xanthene dye of the invention to produce the immobilized compound of the invention.

Exemplary groups of use for $R^b$ in the above described embodiments of the present invention include, but are not limited to, substituted or unsubstituted alkyl (e.g., substituted or unsubstituted arylalkyl, alkylamino, alkoxy), substituted or unsubstituted aryl (e.g., substituted or unsubstituted arylalkyl, aryloxy and aryloxyalkyl), acyl (e.g., acylamino, acyloxy), mercapto, saturated or unsaturated cyclic hydrocarbyl, substituted or unsubstituted heteroaryl (e.g., substituted or unsubstituted heteroarylalkyl), substituted or unsubstituted heterocycloalkyl, and combinations thereof.

Acrylamide-Immobilized Probes

In another exemplary embodiment, a species conjugated to a xanthene dye of the invention is immobilized within a matrix, such as an acrylamide matrix. In a preferred embodiment, the immobilization is accomplished in conjunction with the "acrydite" process (see, Rehman et al., *Nucleic Acids Research*, 27: 649-655 (1999)). The acrydite method allows immobilization of alkene labeled probes within a polymerized polyacrylamide network. When target mixes are run past the immobilized probe band under electrophoresis conditions, the target nucleic acid is captured substantially quantitatively. However, detection of this event currently requires a second probe. In one embodiment, probes bearing a xanthene dye of the invention, and/or a fluorophore, are immobilized in an acrylamide matrix and subsequently contacted with the target mix. By using fluorescent probes as capture probes, signals from target mixes can be directly detected in real time.

Microarrays

The present invention also provides microarrays including immobilized xanthene dye of the invention and compounds (e.g., peptides, nucleic acids, bioactive agents, etc.) functionalized with xanthene dye of the invention. Moreover, the invention provides methods of interrogating microarrays using probes that are functionalized with xanthene dye of the invention. The immobilized species and the probes are selected from substantially any type of molecule, including, but not limited to, small molecules, peptides, enzymes, nucleic acids and the like.

Nucleic acid microarrays consisting of a multitude of immobilized nucleic acids are revolutionary tools for the generation of genomic information, see, Debouck et al., in supplement to *Nature Genetics,* 21:48-50 (1999). The discussion that follows focuses on the use of a xanthene dye of the invention in conjunction with nucleic acid microarrays. This focus is intended to be illustrative and does not limit the scope of materials with which this aspect of the present invention can be practiced.

In another preferred embodiment, the compounds of the present invention are utilized in a microarray format. The xanthene dye of the invention, or species bearing xanthene dye of the invention can themselves be components of a microarray or, alternatively they can be utilized as a tool to screen components of a microarray.

Thus, in a preferred embodiment, the present invention provides a method of screening a microarray. The method includes contacting the members of the microarray with, for example, a xanthene dye of the invention-bearing probe and interrogating the microarray for regions of fluorescence. In an exemplary embodiment, fluorescent regions are indicative of the presence of an interaction between the xanthene dye of the invention-bearing probe and a microarray component.

In another exemplary embodiment, the array comprises an immobilized xanthene-bearing donor-acceptor energy transfer probe. In this embodiment, when the probe interacts (e.g., hybridizes) with its target, energy transfer between the xanthene and a quencher moiety is disrupted and the xanthene dye fluoresces. Such arrays are easily prepared and read, and can be designed to give quantitative data. Arrays comprising a xanthene-bearing probe are valuable tools for expression analysis and clinical genomic screening.

In another embodiment, the immobilized xanthene-bearing probe is not a donor-acceptor energy transfer probe. A microarray based on such as format can be used to probe for the presence of interactions between an analyte and the immobilized probe by, for example, observing the alteration of analyte fluorescence upon interaction between the probe and analyte.

Exemplary microarrays comprise n regions of identical or different species (e.g., nucleic acid sequences, bioactive agents). In a preferred embodiment, n is a number from 2 to 100, more preferably, from 10 to 1,000, and more preferably from 100 to 10,000. In a still further preferred embodiment, the n regions are patterned on a substrate as n distinct locations in a manner that allows the identity of each of the n locations to be ascertained.

In yet another preferred embodiment, the invention also provides a method for preparing a microarray of n xanthene-bearing probes. The method includes attaching xanthene dye-bearing probes to selected regions of a substrate. A variety of methods are currently available for making arrays of biological macromolecules, such as arrays of nucleic acid molecules. The following discussion focuses on the assembly of a microarray of xanthene-bearing probes, this focus is for reasons of brevity and is intended to be illustrative and not limiting.

One method for making ordered arrays of xanthene-bearing probes on a substrate is a "dot blot" approach. In this method, a vacuum manifold transfers a plurality of aqueous samples of probes, e.g., 96, from wells to a substrate. The probe is immobilized on the porous membrane by baking the membrane or exposing it to UV radiation. A common variant of this procedure is a "slot-blot" method in which the wells have highly elongated oval shapes.

Another technique employed for making ordered arrays of probes uses an array of pins dipped into the wells, e.g., the 96 wells of a microtiter plate, for transferring an array of samples to a substrate, such as a porous membrane. One array includes pins that are designed to spot a membrane in a staggered fashion, for creating an array of 9216 spots in a 22×22 cm area. See, Lehrach, et al., HYBRIDIZATION FINGERPRINTING IN GENOME MAPPING AND SEQUENCING, GENOME ANALYSIS, Vol. 1, Davies et al, Eds., Cold Springs Harbor Press, pp. 39-81 (1990).

An alternate method of creating ordered arrays of probes is analogous to that described by Pirrung et al. (U.S. Pat. No. 5,143,854, issued 1992), and also by Fodor et al., (*Science,* 251: 767-773 (1991)). This method involves synthesizing different probes at different discrete regions of a particle or other substrate. This method is preferably used with relatively short probe molecules, e.g., less than 20 bases. A related method was described by Southern et al. (*Genomics,* 13: 1008-1017 (1992)).

Khrapko, et al., *DNA Sequence,* 1: 375-388 (1991) describes a method of making an nucleic acid matrix by spotting DNA onto a thin layer of polyacrylamide. The spotting is done manually with a micropipette.

The substrate can also be patterned using techniques such as photolithography (Kleinfield et al., *J. Neurosci.* 8: 4098-120 (1998)), photoetching, chemical etching and microcontact printing (Kumar et al., *Langmuir* 10: 1498-511 (1994)). Other techniques for forming patterns on a substrate will be readily apparent to those of skill in the art.

The size and complexity of the pattern on the substrate is limited only by the resolution of the technique utilized and the purpose for which the pattern is intended. For example, using microcontact printing, features as small as 200 nm are layered onto a substrate. See, Xia, Y., *J. Am. Chem. Soc.* 117: 3274-75 (1995). Similarly, using photolithography, patterns with features as small as 1 µm are produced. See, Hickman et al., *J. Vac. Sci. Technol.* 12: 607-16 (1994). Patterns which are useful in the present invention include those which include features such as wells, enclosures, partitions, recesses, inlets, outlets, channels, troughs, diffraction gratings and the like.

In a presently preferred embodiment, the patterning is used to produce a substrate having a plurality of adjacent wells, indentations or holes to contain the probes. In general, each of these substrate features is isolated from the other wells by a raised wall or partition and the wells do not readily fluidically communicate. Thus, a particle, reagent or other substance, placed in a particular well remains substantially confined to that well. In another preferred embodiment, the patterning allows the creation of channels through the device whereby an analyte or other substance can enter and/or exit the device.

In another embodiment, the probes are immobilized by "printing" them directly onto a substrate or, alternatively, a "lift off" technique can be utilized. In the lift off technique, a patterned resist is laid onto the substrate, and a probe is laid down in those areas not covered by the resist and the resist is subsequently removed. Resists appropriate for use with the substrates of the present invention are known to those of skill in the art. See, for example, Kleinfield et al., *J. Neurosci.* 8: 4098-120 (1998). Following removal of the photoresist, a second probe, having a structure different from the first probe can be bonded to the substrate on those areas initially covered by the resist. Using this technique, substrates with patterns of probes having different characteristics can be produced. Similar substrate configurations are accessible through microprinting a layer with the desired characteristics directly onto the substrate. See, Mrkish et al. *Ann. Rev. Biophys. Biomol. Struct.* 25:55-78 (1996).

Linkers

As used herein, the term "linker," refers to a constituent of a conjugate between a xanthene dye and a carrier molecule. The linker is a component of the xanthene dye, the carrier molecule or it is a reactive cross-linking species that reacts with both the carrier molecule and the xanthene dye. The linker groups can be hydrophilic (e.g., tetraethylene glycol, hexaethylene glycol, polyethylene glycol) or they can be hydrophobic (e.g., hexane, decane, etc.). Exemplary linkers include substituted or unsubstituted $C_6$-$C_{30}$ alkyl groups, polyols (e.g., glycerol), polyethers (e.g., poly(ethyleneglycol)), polyamines, amino acids (e.g., polyaminoacids), saccharides (e.g., polysaccharides) and combinations thereof.

In an exemplary embodiment, the linker joins donor and/or acceptor moieties and other groups to a nucleic acid, peptide or other component of a probe. In a further exemplary embodiment, using a solid support, the immobilized construct includes a linker attached through the solid support and also to the xanthene dye.

In certain embodiments, it is advantageous to have the donor and/or acceptor moieties of the probe attached to a carrier molecule by a group that provides flexibility and distances the linked species from the carrier molecule. Using linker groups, the properties of the donor and/or acceptor moiety is modulated. Properties that are usefully controlled include, for example, hydrophobicity, hydrophilicity, surface-activity, the distance of the quencher and/or xanthene dye of the invention moiety from the other probe components (e.g., carrier molecule) and the distance of the quencher from the xanthene dye of the invention.

In an exemplary embodiment, the linker serves to distance the xanthene dye of the invention from a nucleic acid to which it is attached. Linkers with this characteristic have several uses. For example, a xanthene dye of the invention held too closely to the nucleic acid may not interact with the quencher group, or it may interact with too low of an affinity. When a xanthene dye of the invention is itself sterically demanding, the interaction leading to quenching can be undesirably weakened, or it may not occur at all, due to a sterically induced hindering of the approach of the two components.

When the construct comprising the xanthene dye is immobilized by attachment to, for example, a solid support, the construct can also include a linker moiety placed between the reactive group of the solid support and the xanthene analogue, or other probe component bound to the solid support.

In yet a further embodiment, a linker group used in the probes of the invention is provided with a group that can be cleaved to release a bound moiety, e.g., a xanthene dye of the invention, quencher, minor groove binder, intercalating moiety, and the like from the polymeric component. Many cleaveable groups are known in the art. See, for example, Jung et al., *Biochem. Biophys. Acta,* 761: 152-162 (1983); Joshi et al., *J. Biol. Chem.,* 265: 14518-14525 (1990); Zarling et al., *J. Immunol.,* 124: 913-920 (1980); Bouizar et al., *Eur. J. Biochem.,* 155: 141-147 (1986); Park et al., *J. Biol. Chem.,* 261: 205-210 (1986); Browning et al., *J. Immunol.,* 143: 1859-1867 (1989). Moreover a broad range of cleavable, bifunctional (both homo- and hetero-bifunctional) linker arms is commercially available from suppliers such as Pierce. Exemplary cleaveable groups are those cleaved by light, e.g., nitrobenzyl derivatives, phenacyl groups, benzoin esters; hydrolysis, e.g., esters, carbonates; changes in pH, etc.

The Methods

In another aspect of the embodiment, the present invention provides a method for detecting a target species in an assay mixture or other sample. The following discussion is generally relevant to the assays described herein. This discussion is intended to illustrate the invention by reference to certain preferred embodiments and should not be interpreted as limiting the scope of probes and assay types in which the compounds of the invention find use. Other assay formats utilizing the compounds of the invention will be apparent to those of skill in the art.

An exemplary method uses a xanthene dye of the invention or a conjugate thereof to detect a nucleic acid target sequence. The method includes: (a) contacting the target sequence with a detector nucleic acid that includes a xanthene dye of the invention and a quencher; (b) hybridizing the detector nucleic acid to the target sequence, thereby altering the conformation of the detector nucleic acid, causing a change in a fluorescence parameter; and (c) detecting the change in the fluorescence parameter, thereby detecting the nucleic acid target sequence.

In the methods described herein, unless otherwise noted, a preferred detector nucleic acid includes a single-stranded target binding sequence. The binding sequence has linked thereto: i) a quencher; and ii) a xanthene dye of the invention. Moreover, prior to its hybridization to a complementary sequence, the detector nucleic acid is preferably in a conformation that allows donor-acceptor energy transfer between the quencher and the xanthene dye of the invention when the fluorophore is excited. Furthermore, in the methods described in this section, a change in fluorescence is detected as an indication of the presence of the target sequence. The change in fluorescence is preferably detected in real time.

Presently preferred nucleic acid probes do not require the carrier molecule to adopt a secondary structure for the probe to function. Exemplary probes according to this motif include a quencher moiety that includes the diazo-linked quenchers described in co-pending, commonly assigned U.S. patent application Ser. No. 09/567,863 or the conformationally assisted probes disclosed in U.S. patent application Ser. No. 09/591,185.

In other methods described in this section, the detector nucleic acid can assume substantially any intramolecularly associated secondary structure, e.g., hairpins, stem-loop structures, pseudoknots, triple helices and conformationally assisted structures. Moreover, the intramolecularly base-paired secondary structure preferably comprises a portion of the target binding sequence.

In another aspect, the invention provides a method for detecting amplification of a target sequence. The method includes the use of an amplification reaction including the following steps: (a) hybridizing the target sequence and a detector nucleic acid that includes a xanthene dye of the invention. The detector nucleic acid preferably includes a single-stranded target binding sequence and an intramolecularly associated secondary structure 5' to the target binding sequence. At least a portion of the detector sequence forms a single stranded tail which is available for hybridization to the target sequence; (b) extending the hybridized detector nucleic acid on the target sequence with a polymerase to produce a detector nucleic acid extension product and separating the detector nucleic acid extension product from the target sequence; (c) hybridizing a primer to the detector nucleic acid extension product and extending the primer with the polymerase, thereby linearizing the intramolecularly associated secondary structure and producing a change in a fluorescence parameter; and (d) detecting the change in the fluorescence parameter, thereby detecting the target sequence.

In yet a further aspect, the invention provides a method of ascertaining whether a first nucleic acid and a second nucleic acid hybridize. In this method, the first nucleic acid includes a xanthene dye of the invention. The method includes: (a) contacting the first nucleic acid with the second nucleic acid; (b) detecting an alteration in a fluorescent property of a member selected from the first nucleic acid, the second nucleic acid and a combination thereof, thereby ascertaining whether the hybridization occurs.

In general, to determine the concentration of a target molecule, e.g., a nucleic acid, it is preferable to first obtain reference data in which constant amounts of probe are contacted with varying amounts of target. The fluorescence emission of each of the reference mixtures is used to derive a graph or table in which target concentration is compared to fluorescence emission. For example, a probe that hybridizes to a nucleic acid ligand and has a stem-loop architecture with the 5' and 3' termini being the sites of quencher and xanthene labeling, can be used to obtain such reference data. The value of the fluorescence emission is then compared with the reference data to obtain the concentration of the target in the test mixture.

The xanthene dyes and their conjugates described herein can be used in substantially any nucleic acid probe format now known or later discovered. For example, the xanthene dyes of the invention can be incorporated into probe motifs, such as Taqman™ probes (Held et al., *Genome Res.* 6: 986-994 (1996), Holland et al., *Proc. Nat. Acad. Sci. USA* 88: 7276-7280 (1991), Lee et al., *Nucleic Acids Res.* 21: 3761-3766 (1993)), molecular beacons (Tyagi et al., *Nature Biotechnology* 14:303-308 (1996), Jayasena et al., U.S. Pat. No. 5,989,823, issued Nov. 23, 1999)) scorpion probes (Whitcomb et al., *Nature Biotechnology* 17: 804-807 (1999)), sunrise probes (Nazarenko et al., *Nucleic Acids Res.* 25: 2516-2521 (1997)), conformationally assisted probes (Cook, R., copending and commonly assigned U.S. patent application Ser. No. 09/591,185), peptide nucleic acid (PNA)-based light up probes (Kubista et al., WO 97/45539, December 1997), double-strand specific DNA dyes (Higuchi et al, *Bio/Technology* 10: 413-417 (1992), Wittwer et al, *BioTechniques* 22: 130-138 (1997)) and the like. These and other probe motifs with which the present xanthene dyes can be used are reviewed in NONISOTOPIC DNA PROBE TECHNIQUES, Academic Press, Inc. 1992.

Peptides, proteins and peptide nucleic acids that are labeled with a quencher and a xanthene dye of the invention can be used in both in vivo and in vitro enzymatic assays.

Thus, in another aspect, the present invention provides a method for determining whether a sample contains an enzyme. The method comprises: (a) contacting the sample with a peptide construct that includes a xanthene dye of the invention; (b) exciting the fluorophore; and (c) determining a fluorescence property of the sample, wherein the presence of the enzyme in the sample results in a change in the fluorescence property. In selected embodiments, a fluorescence property of the probe is measured prior to incubating the probe with the enzyme.

Peptide constructs useful in practicing the invention include those with the following features: i) a quencher; ii) a xanthene dye of the invention; and iii) a cleavage or assembly recognition site for the enzyme. Moreover, the peptide construct is preferably exists in at least one conformation that allows donor-acceptor energy transfer between the xanthene dye of the invention and the quencher when the fluorophore is excited.

When the probe is used to detect an enzyme, such as a degradative enzyme (e.g., protease), and a degree of donor-acceptor energy transfer that is lower than an expected amount is observed, this is generally indicative of the presence of an enzyme. The degree of donor-acceptor energy transfer in the sample can be determined, for example, as a function of the amount of fluorescence from the donor moiety, the amount of fluorescence from the acceptor moiety, the ratio of the amount of fluorescence from the donor moiety to the amount of fluorescence from the acceptor moiety or the excitation state lifetime of the donor moiety.

The assay also is useful for determining the amount of enzyme in a sample. For example, by determining the degree of donor-acceptor energy transfer at a first and second time after contact between the enzyme and the tandem construct, and determining the difference in the degree of donor-acceptor energy transfer. The difference in the degree of donor-acceptor energy transfer is related to the amount of enzyme in the sample, the activity of the enzyme towards the construct, or both.

The assay methods also can also be used to determine whether a compound alters the activity of an enzyme, i.e., screening assays. Thus, in a further aspect, the invention provides methods of determining the amount of activity of an enzyme in a sample from an organism. The method includes: (a) contacting a sample comprising the enzyme and the compound with a peptide construct that includes a xanthene dye of the invention; (b) exciting the fluorophore; and (c) determining a fluorescence property of the sample, wherein the activity of the enzyme in the sample results in a change in the fluorescence property. Peptide constructs useful in this aspect of the invention are substantially similar to those described immediately above.

In a preferred embodiment, the amount of enzyme activity in the sample is determined as a function of the degree of donor-acceptor energy transfer in the sample and the amount of activity in the sample is compared with a standard activity for the same amount of the enzyme. A difference between the amount of enzyme activity in the sample and the standard activity indicates that the compound alters the activity of the enzyme.

Representative enzymes with which the present invention can be practiced include, for example, trypsin, enterokinase, HIV-1 protease, prohormone convertase, interleukin-1b-converting enzyme, adenovirus endopeptidase, cytomegalovirus assemblin, leishmanolysin, β-secretase for amyloid precursor protein, thrombin, renin, angiotensin-converting enzyme, cathepsin-D and a kininogenase, and proteases in general.

Proteases play essential roles in many disease processes such as Alzheimer's, hypertension, inflammation, apoptosis, and AIDS. Compounds that block or enhance their activity have potential as therapeutic agents. Because the normal substrates of peptidases are linear peptides and because established procedures exist for making non-peptidic analogs, compounds that affect the activity of proteases are natural subjects of combinatorial chemistry. Screening compounds produced by combinatorial chemistry requires convenient enzymatic assays.

Convenient assays for proteases are based on donor-acceptor energy transfer from a donor fluorophore to a quencher placed at opposite ends of a short peptide chain containing the potential cleavage site (see, Knight C. G., *Methods in Enzymol.* 248:18-34 (1995)). Proteolysis separates the fluorophore and quencher, resulting in increased intensity in the emission of the donor fluorophore. Existing protease assays use short peptide substrates incorporating unnatural chromophoric amino acids, assembled by solid phase peptide synthesis.

Assays of the invention are also useful for determining and characterizing substrate cleavage sequences of proteases or for identifying proteases, such as orphan proteases. In one embodiment the method involves the replacement of a defined linker moiety amino acid sequence with one that contains a randomized selection of amino acids. A library of fluorescent xanthene dye probes, wherein the xanthene dyes of the invention are linked by a randomized peptide linker moiety, which can be generated using recombinant engineering techniques or synthetic chemistry techniques. Screening the members of the library can be accomplished by measuring a signal related to cleavage, such as donor-acceptor energy transfer, after contacting the cleavage enzyme with each of the library members of the tandem fluorescent peptide construct. A degree of donor-acceptor energy transfer that is lower than an expected amount indicates the presence of a linker sequence that is cleaved by the enzyme. The degree of donor-acceptor energy transfer in the sample can be determined, for example, as a function of the amount of fluorescence from the donor moiety, the amount of fluorescence from the acceptor donor moiety, or the ratio of the amount of fluorescence from the donor moiety to the amount of fluorescence from the acceptor moiety or the excitation state lifetime of the donor moiety.

Multiplex Analyses

In another exemplary embodiment, the xanthene dyes of the invention are utilized as a component of one or more probes used in a multiplex assay for detecting one or more species in a mixture.

Probes that include a xanthene dye are particularly useful in performing multiplex-type analyses and assays. In a typical multiplex analysis, two or more distinct species (or regions of one or more species) are detected using two or more probes, wherein each of the probes is labeled with a different fluorophore, quencher or fluorophore/quencher pair. Preferred species used in multiplex analyses relying on donor-acceptor energy transfer meet at least two criteria: the fluorescent species is bright and spectrally well resolved; and the energy transfer between the fluorescent species and the quencher is efficient.

Thus, in a further embodiment, the invention provides a mixture comprising at least a first carrier molecule and a second carrier molecule. The first carrier molecule has covalently bound thereto a first quencher and a first xanthene dye of the invention. An exemplary quencher has a structure that includes at least three radicals selected from aryl, substituted aryl, heteroaryl, substituted heteroaryl and combinations thereof. At least two of the radicals are covalently linked via an exocyclic diazo bond. The mixture also includes a second carrier molecule. The fluorophore, quencher or both the fluorophore and quencher attached to the second carrier molecule is different than that attached to the first nucleic acid. Exemplary quenchers of use in conjunction with the compounds of the invention include those described in commonly owned WO 01/86001.

The xanthene dye of the invention allows for the design of multiplex assays in which more than one quencher structure is used in the assay. In one exemplary assay, at least two distinct xanthene dyes of the invention are used with a common quencher structure. The quencher(s) can be bound to the same molecule as the xanthene dye of the invention or to a different molecule. Moreover, the carrier molecules of use in a particular assay system can be the same or different.

In addition to those embodiment described above, the present invention also provides a method for detecting and/or quantifying a particular molecular species. The method includes: (a) contacting the species with a mixture such as that described above; and (b) detecting a change in a fluorescent property of one or more component of the mixture, the molecular species or a combination thereof, thereby detecting and/or quantifying the molecular species.

Because the present invention provides readily available, reactive xanthene dyes, which can be "tuned" to emit fluorescence of a desired wavelength, the compounds of the invention are particularly well suited for use in multiplex applications. Access to xanthene dyes of the invention having a range of emission characteristics allows for the design of donor-acceptor energy transfer probes in which the acceptor absorbance properties and the emission properties of the xanthene are substantially matched, thereby providing a useful level of spectral overlap. Moreover, the xanthene dyes of the invention provide access to probes that emit light at different wavelengths, allowing the probes to be spectrally resolved, which is desirable for multiplex analysis.

The simultaneous use of two or more probes using donor-acceptor energy transfer is known in the art. For example, multiplex assays using nucleic acid probes with different sequence specificities have been described. Fluorescent probes have been used to determine whether an individual is homozygous wild type, homozygous mutant or heterozygous for a particular mutation. For example, using one quenched-fluorescein molecular beacon that recognizes the wild-type sequence and another rhodamine-quenched molecular beacon that recognizes a mutant allele, it is possible to genotype individuals for the β-chemokine receptor (Kostrikis et al. *Science* 279:1228-1229 (1998)). The presence of only a fluorescein signal indicates that the individual is wild type, and the presence of rhodamine signal only indicates that the individual is a homozygous mutant. The presence of both rhodamine and fluorescein signal is diagnostic of a heterozygote. Tyagi et al. *Nature Biotechnology* 16: 49-53 (1998)) have described the simultaneous use of four differently labeled molecular beacons for allele discrimination, and Lee et al., *BioTechniques* 27: 342-349 (1999) have described seven color homogenous detection of six PCR products. The compounds of the invention are of use in such methods.

The dyes of the present invention can be used in multiplex assays designed to detect and/or quantify substantially any species, including, for example, whole cells, viruses, proteins (e.g., enzymes, antibodies, receptors), glycoproteins, lipoproteins, subcellular particles, organisms (e.g., *Salmonella*), nucleic acids (e.g., DNA, RNA, and analogues thereof), polysaccharides, lipopolysaccharides, lipids, fatty acids, non-biological polymers and small molecules (e.g., toxins, drugs, pesticides, metabolites, hormones, alkaloids, steroids).

Kits

In another aspect, the present invention provides kits containing one or more xanthene dye of the invention or a conjugate thereof. In one embodiment, a kit includes a reactive xanthene dye of the invention and directions for attaching this derivative to another molecule. In another embodiment, the kit includes a xanthene-labeled carrier, e.g., a nucleic acid that optionally is also labeled with a quencher and directions for using this nucleic acid in one or more assay format. Other formats for kits will be apparent to those of skill in the art and are within the scope of the present invention.

The materials and methods of the present invention are further illustrated by the examples that follow. These examples are offered to illustrate, but not to limit the claimed invention.

The following examples are provided by way of illustration only and not by way of limitation. Those of skill in the art will readily recognize a variety of non-critical parameters that could be changed or modified to yield essentially similar results.

EXAMPLES

Example 1

1.1 Preparation of Rhodamine B Acid Chloride 1

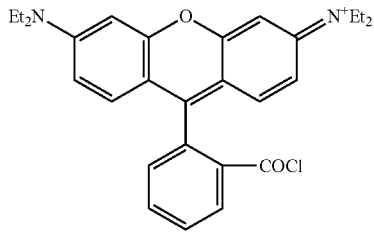

To a 500 mL round bottom flask were added 80% rhodamine B (6.0 g, 5.0 mmol) and phosphorus oxychloride (50 mL). The flask was fitted with a condenser and calcium sulfate drying tube. The reaction mixture was heated at reflux for 16 h and then cooled to room temperature. The volatile components were removed under high vacuum. Acetonitrile (100 mL) was added to dissolve the residue and was then removed by rotary evaporation and high vacuum. The solid material was again dissolved in acetonitrile (100 mL) and stripped to dryness to afford crude rhodamine B acid chloride.

1.2 Rhodamine B N-methylaminobutanol hexafluorophosphate 2

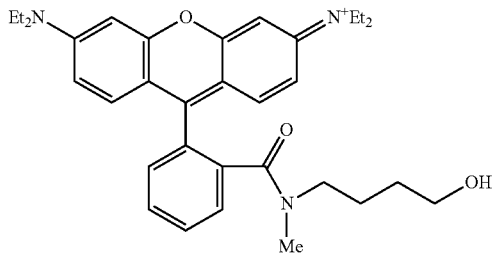

Crude rhodamine B acid chloride (5.13 g, approx. 8.2 mmol) was dissolved in a mixture of DMF (20 mL) and acetonitrile (70 mL) and to this solution was added a solution of N-methylaminobutanol (3.0 g, 29.1 mmol) and triethylamine (7 mL) in acetonitrile (10 mL). The flask was fitted with a septum and was warmed at 60° C. overnight. The volatile components were removed under high vacuum and the residue was partitioned between dichloromethane (200 mL) and 1N aqueous hydrochloric acid (200 mL). The aqueous phase was washed with dichloromethane (3×200 mL). The combined organic solutions were washed with aqueous potassium hexafluorophosphate solution (3×100 mL of 1 g/100 ml), dried (MgSO$_4$) filtered and evaporated in vacuo to afford a red solid. The solid was dissolved in pyridine and stripped to dryness under high vacuum at 90° C. overnight to afford crude rhodamine B, N-methylaminobutanol hexafluorophosphate as a red solid (4.11 g, 74%).

1.3 Rhodamine B N-methylaminobutanol phosphoramidite 3

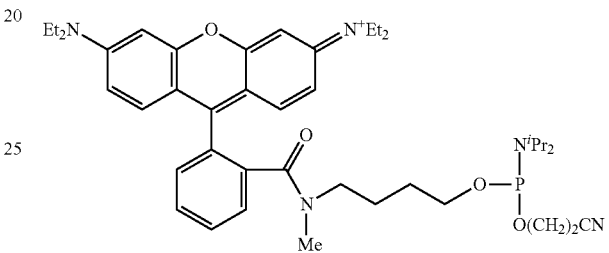

Dry crude rhodamine B N-methylaminobutanol (2.24 g, 4.0 mmol) was dissolved in dry dichloromethane (50 mL) and then 1-H-tetrazole (0.070 g, 1.0 mmol) was added. N,N,N', N'-tetraisopropyl β-cyanoethyl phosphane (1.5 g, 5 mmol) was dissolved in dry dichloromethane (10 mL) and this solution was added to that of the dye. The flask was fitted with a septum and the mixture was stirred at room temperature for 4 h. The solution was diluted with dichloromethane (120 mL) and then was washed with saturated sodium bicarbonate solution (2×60 mL), dried (MgSO$_4$), filtered and evaporated in vacuo to leave an oil. The oil was washed with diethyl ether (3×50 mL) and the resulting solid residue was dissolved in pyridine (60 mL). The pyridine was removed under high vacuum and the residue was dissolved in dichloromethane (5 mL). Removal of the dichloromethane in vacuo afforded the phosphoramidite as a red solid (2.9 g).

1.4 Rhodamine B N-methylaminoethanol chloride 4

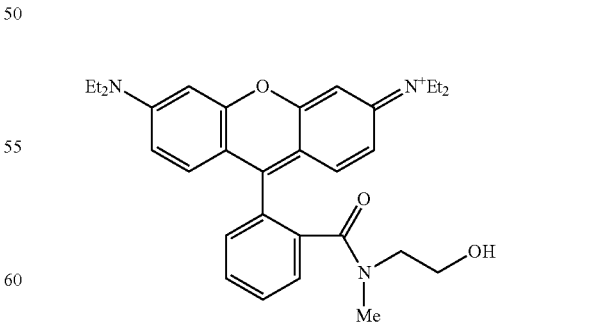

To a 500 mL round bottom flask were added 80% rhodamine B (12.2 g, 20.3 mmol) and phosphorus oxychloride (120 mL). The flask was fitted with a condenser and calcium sulfate drying tube. The reaction mixture was heated at reflux for 16 h and then cooled to room temperature. The volatile components were removed under high vacuum. Acetonitrile (100 mL) was added to dissolve the residue and was then removed by rotary evaporation and high vacuum. The solid material was again dissolved in acetonitrile (100 mL) and to this solution was added a solution of N-methylaminoethanol (5.0 g, 66.6 mmol) and triethylamine (20 mL) in acetonitrile (100 mL). The mixture was stirred at room temperature overnight and then the volatile components were removed in vacuo. The residue was partitioned between dichloromethane (300 mL) and 1N aqueous hydrochloric acid (200 mL). The aqueous phase was washed with dichloromethane (3×300 mL). The combined organic solutions were dried (MgSO$_4$) filtered and evaporated in vacuo to afford rhodamine B N-methylaminoethanol chloride as a red solid (12.9 g).

1.5 Rhodamine B N-methylaminoethanol hexafluorophosphate 5

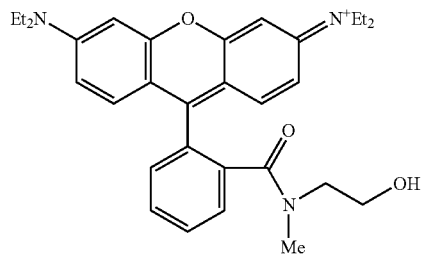

Rhodamine B N-methylaminoethanol chloride (4.0 g, approx. 6 mmol) was dissolved in dichloromethane (500 mL) and the solution was washed with aqueous potassium hexafluorophosphate solution (3×100 mL of 1 g/100 mL). The organic phase was dried (MgSO$_4$), filtered and evaporated in vacuo. The residue was dissolved in pyridine (100 mL) and resulting solution was evaporated under high vacuum to afford rhodamine B, N-methylaminoethanol hexafluorophosphate as a dry purple solid.

1.6 Rhodamine B N-methylaminoethanol phosphoramidite 6

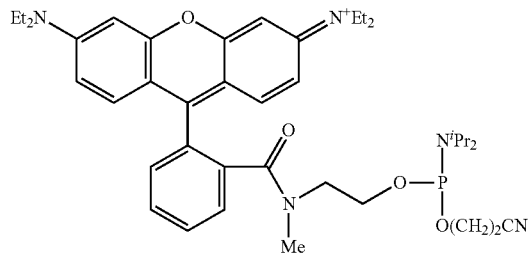

Rhodamine B, N-methylaminoethanol hexafluorophosphate (2.45 g, approx. 3.8 mmol) was dissolved in dichloromethane (50 mL) and then 1-H-tetrazole (0.07 g, 1.0 mmol) was added. N,N,N',N'-tetraisopropyl-β-cyanoethyl phosphane (1.67 g, 5.5 mmol) was dissolved in dichloromethane (10 mL) and the solution was added to that of the dye. The mixture was stirred at room temperature for 4 h. The solution was diluted with dichloromethane (120 mL) and then was washed with saturated sodium bicarbonate solution (2×60 mL), dried (MgSO$_4$), filtered and evaporated in vacuo to leave an oil. The oil was washed with diethyl ether (3×60 mL) and the resulting solid residue was dissolved in pyridine (60 mL). The pyridine was removed under high vacuum at 45° C. and then the residue was dissolved in dichloromethane (5 mL). Removal of the dichloromethane in vacuo afforded the phosphoramidite as a red foam.

1.7 Rhodamine B N-methylaminoethanoxy hydroxyhexyl urethane hexafluorophosphate 7

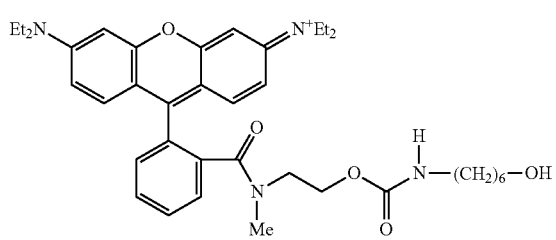

To a 250 mL round bottom flask were added rhodamine B ethanol hexafluorophosphate (1.75 g, 2.71 mmol) and dry pyridine (30 mL). The mixture was stirred while a solution of p-nitrophenylchloroformate (0.73 g, 3.62 mmol) in dioxane (15 mL) was added over 5 min. The flask was fitted with a septum and stirring was continued for a further 2 h. A second solution of p-nitrophenylchloroformate (0.44 g, 2.18 mmol) in dioxane (10 mL) was added and the mixture was stirred for 96 h. The volatile components were removed in vacuo and the residue was dissolved in dichloromethane (100 mL). The solution was washed with water (60 mL), dried (MgSO$_4$), and filtered. After concentrating to approx. 30 mL, the solution was added portion-wise over 5 min. to a solution of 6-aminohexanol (3.3 g, 28.2 mmol, excess) and diisopropylethylamine (3 mL) in dichloromethane (33 mL). The mixture was stirred for 90 minutes and then diluted to 250 mL with dichloromethane. The solution was washed with 1N aqueous hydrochloric acid (2×50 mL), dried (MgSO$_4$), filtered and evaporated in vacuo to afford a red solid that was subjected to column chromatography on silica gel (6×20 cm) using 5% methanol in dichloromethane as eluant. The pure fractions were evaporated in vacuo and the residue was dissolved in dichloromethane (30 mL) and filtered through a medium frit. Evaporation of the solvent afforded the urethane derivative as a red solid (1.32 g, 62%).

1.8 Rhodamine B N-methylaminoethanoxy hydroxyhexyl urethane phosphoramidite 8

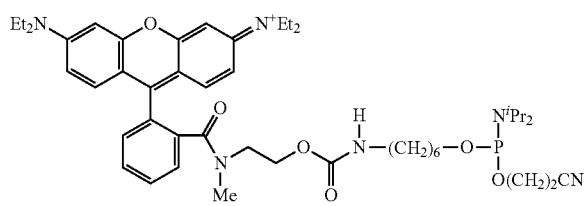

Rhodamine B N-methylaminoethanoxyhydroxyhexyl urethane hexafluorophosphate (0.825 g, 1.0 mmol) was dissolved in pyridine and then stripped to dryness under high vacuum at 80° C. overnight. It was dissolved in dry dichloromethane (30 mL) and then 1-H-tetrazole (0.050 g, 0.71 mmol) was added. N,N,N',N'-tetraisopropyl-β-cyanoethyl phosphane (0.50 g, 1.7 mmol) was dissolved in dry dichloromethane (10 mL) and this solution was added to that of the dye. The flask was fitted with a septum and the mixture was stirred at room temperature for 3 h. The solution was diluted with dichloromethane (120 mL) and then was washed with saturated sodium bicarbonate solution (2×60 mL), dried (MgSO₄), filtered and evaporated in vacuo to leave an oil. The oil was washed with diethyl ether (3×60 mL) and the resulting solid residue was dissolved in pyridine (60 mL). The pyridine was removed under high vacuum at 45° C. and the residue was dissolved in dichloromethane (5 mL). Removal of the dichloromethane in vacuo afforded the phosphoramidite as a red foam (0.91 g, 88%).

Example 2

2.1 Preparation of Rhodamine 6G Acid 9

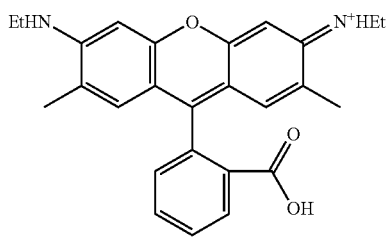

Rhodamine 6G (17.3 g, 36.4 mmol) was dissolved in DMSO (320 mL) and 1N aqueous sodium hydroxide (80 mL) was added. The mixture was stirred for 16 h and then was neutralized by addition of 1N aqueous hydrochloric acid. The solid was filtered off and was dissolved in the minimum amount of methanol (approx. 500 mL). The solution was added to 1N aqueous hydrochloric acid (1200 mL) and then the methanol was boiled off. After cooling the solid was filtered off and was washed with water (2×30 mL). The solid was dried to afford the R6G acid (16 g, 97%).

2.2 Preparation of Rhodamine R6G succinimidyl ester 10

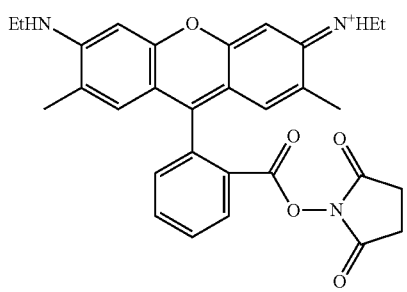

To a 100 mL round bottom flask was added rhodamine R6G acid (6.63 g, 14.7 mmol), TSTU (5.25 g, 17.4 mmol), DMF (150 mL) and diisopropylethylamine (9 mL). The mixture was stirred at room temperature for 20 h. The solid was filtered off, was washed with DMF (2×4 mL) and acetonitrile (2×5 mL), and was dried to afford rhodamine R6G succinimidyl ester (2.9 g, 36%).

2.3 Rhodamine R6G N-methylaminobutanol 11

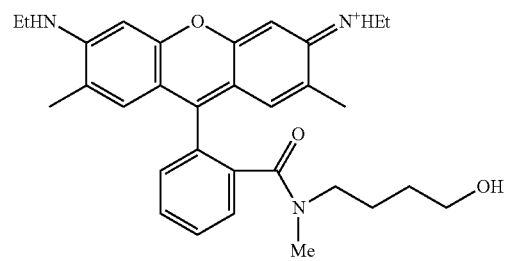

To a 50 mL flask were added rhodamine R6G succinimidyl ester (1.0 g, 1.83 mmol), N-methylaminobutanol (1.16 g, 11.3 mmol) and DMF (5 mL). The mixture was heated at 60° C. for 18 hours and then was diluted with water (150 mL). The solution was applied to a column of C-18 reversed phase silica gel (3×13 cm). The column was eluted with a sharp gradient of 0 to 100% methanol to remove the impurities and then with acidified methanol (5 mL of 1N aq. HCl in 1 L methanol) to elute the product. Evaporation of the eluant in vacuo afforded rhodamine R6G N-methylaminobutanol (0.81 g, 83%).

2.4 Preparation of Rhodamine 6 G N-methylaminoethanol 12

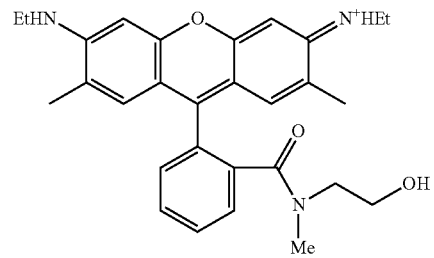

Commercially available Rhodamine 6 G (50 g) was heated to 120° C. with N-methylethanolamine (150 mL). The reaction mixture was checked after 1 h by MALDI mass spectroscopy showing clean conversion into product, M/e 474. The hot solution was poured carefully into 2N HCl (1200 mL) and chilled overnight. A red solid was collected by filtration and washed with 0.5 N HCl (300 mL). The material was air dried for several days, then subjected to high vacuum for 18 h to give Rhodamine 6 G N-methylaminoethanol (38 g).

2.5 Preparation of 13, p-nitrophenylcarbonate of 12

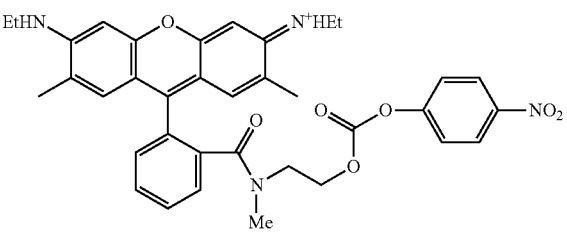

Rhodamine 6 G N-methylaminoethanol (38 g) was dissolved in dry pyridine (800 mL) and a solution of p-nitrophenyl chloroformate (30 g) in dry dioxane (400 mL) was added dropwise over 30 min. After 1 h of additional stirring, a mass spectrum of an aliquot revealed conversion to a compound of M/e 641, consistent with the p-nitrophenyl carbonate ester. The solution was stripped to a tar by rotary evaporation and re-dissolved in 1 L of dichloromethane. This solution was washed with water, 800 mL and then stripped to an oil by rotary evaporation.

2.6 Preparation of Rhodamine 6 G N-methylaminoethanoxy hydroxyhexyl urethane 14

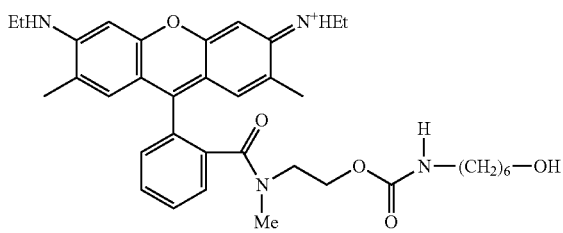

A solution of 40 g 6-amino-1-hexanol in 700 mL THF and 500 mL saturated aq. $Na_2CO_3$ was prepared, and 13 was dissolved in 500 mL THF and added over 20 min. The bright red mixture was stirred for an additional hr, whereupon a mass spectrum revealed conversion to a compound of M/e 618, consistent with the urethane derivative. Most of the THF was removed by rotary evaporation, and the aqueous residue was extracted with dichloromethane (800 mL). The dichloromethane layer was washed with water (500 mL) followed by brine (500 mL). The organic phase was reduced to about 300 mL by rotary evaporation and applied to a column packed with a (10×40 cm) bed of basic alumina in 2% methanol in dichloromethane. The column was eluted at 100 mL/min with this same mobile phase until early running colored bands eluted, then the methanol was increased to 4%. The product eluted as a bright orange band: fractions collected from this band were checked by TLC (20% methanol, 2% pyridine in dichloromethane). Pure fractions ($r_f$=0.6) were pooled and evaporated to give 14 (15 g).

2.7 Preparation of Rhodamine 6 G N-methylaminoethanoxy hydroxyhexyl urethane phosphoramidite 15

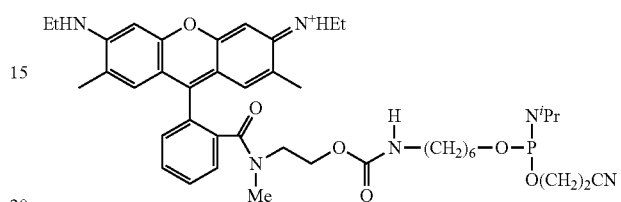

Compound 14 (15 g) was dried by rotary evaporation from dry pyridine (400 mL) and high vacuum for 24 h. The compound was then dissolved in dry dichloromethane (150 mL) and a premixed solution of N,N,N',N'-tetraisopropyl betacyanoethyl phosphane (7.5 g) and tetrazole (500 mg) in dry acetonitrile (150 mL) were added. After 2 h, TLC (same conditions as above) showed conversion to a new compound ($r_f$=0.7), and a mass spectrum of an aliquot showed M/e 820, consistent with formation of the phosphoramidite. The solution was reduced by rotary evaporation to a tar, then re-dissolved in dichloromethane (600 mL). The solution was washed with 5% aqueous $Na_2CO_3$ solution (400 mL) and dried over $MgSO_4$. Evaporation, followed by chromatography and evaporation as above gave pure 15 as a red foam (19 g).

Example 3

3.1 Preparation of 19 from Rhodamine 101

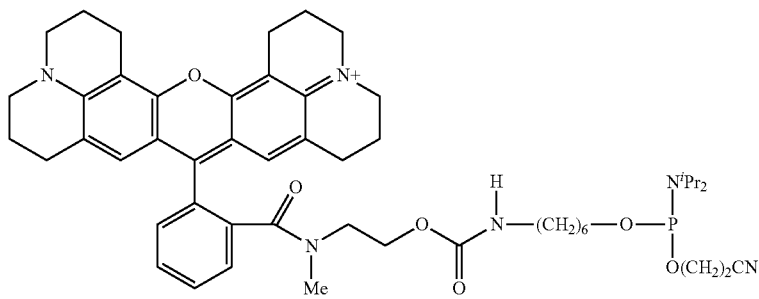

Compound 19 and it precursors 16-18 were prepared in a manner analogous to corresponding compounds of Example 2.

Example 4

4.1 Preparation of Dichlorophenyl Xanthene Dye

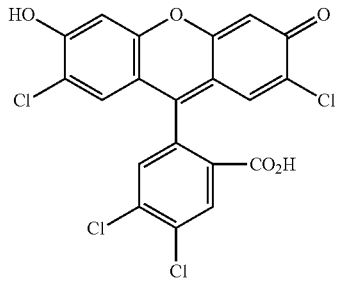 [SMILES: O=C(O)c1cc(Cl)c(Cl)cc1-c1c2cc(Cl)c(=O)cc-2oc2cc(O)c(Cl)cc12]

4-Chlororesorcinol (33 g) was mixed with 4,5-dichlorophthalic anhydride in methane sulfonic acid (100 mL) according to the procedure of Menchen, et. al, (U.S. Pat. No. 5,654,442). Briefly, with magnetic stirring, the solution was heated to 180° C. over 30 min and maintained for an additional 30 minutes. The mixture was allowed to cool to ~100° C. and was cautiously poured into water (1 L). The solid was collected by filtration and air dried for several days, followed by 24 h of high vacuum and was characterized as having the structure above.

4.2 Preparation of the Dichlorophenyl Ethyl Ester 20

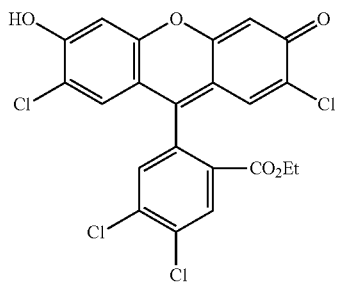 [SMILES: CCOC(=O)c1cc(Cl)c(Cl)cc1-c1c2cc(Cl)c(=O)cc-2oc2cc(O)c(Cl)cc12]

The compound from Example 4.1 (50 g) was refluxed with absolute ethanol (1 L), which contained chlorotrimethylsilane (60 mL). After 2 h the solution was cooled and the volatile components were removed by rotary evaporation. High vacuum was applied to the orange solid for 24 h to give 20, (55 g).

4.3 Preparation of N-methanolaminoethanol amide 21

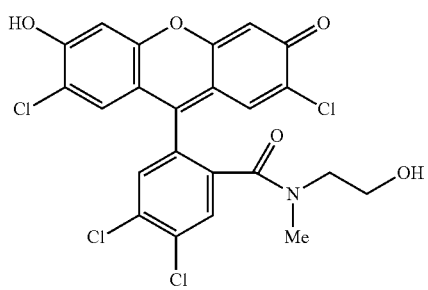 [SMILES: CN(CCO)C(=O)c1cc(Cl)c(Cl)cc1-c1c2cc(Cl)c(=O)cc-2oc2cc(O)c(Cl)cc12]

Ethyl ester 20 (7 g) was mixed with N-methylethanolamine (30 mL) and heated to 120° C., with magnetic stirring. After 30 min, the solution was poured cautiously into 2N HCl (1 L). The solid was collected by filtration and air dried for several days, followed by 24 h of high vacuum to give 21 as a red solid (8 g).

4.4 Preparation of dimethoxytrityl ether 22 of N-methanolaminoethanol amide 21

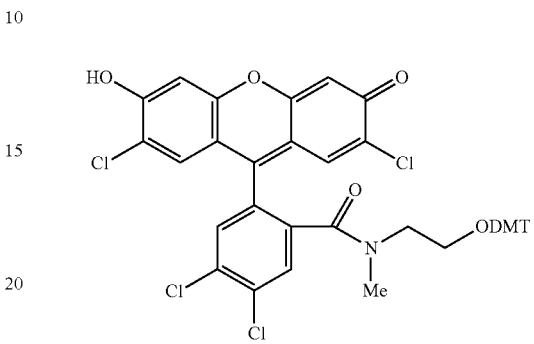

Amino alcohol 21 (8 g) was dissolved in dry pyridine (200 mL) and DMT-chloride (10 g) was added. After stirring overnight, a mass spectrum of an aliquot showed a peak at 833 M/e, consistent with the addition of the DMT group to the aliphatic hydroxyl. The solvent was removed by rotary evaporation, and the residue was dissolved in dichloromethane (300 mL). The orange solution was washed with saturated NaHCO$_3$ (200 mL), followed by brine (200 mL). The crude material was then dissolved in a solution (50 mL) of 1% methanol, 1% TEA in dichloromethane. This was applied to a column of neutral alumina (5×20 cm), 7% by weight water, and eluted with 1 L of the above-described mobile phase. A gradient to 4% methanol was then run over 4 liters of solvent. Pure fractions containing 22 (TLC rf 0.6, silica plates with 5% methanol, 1% TEA in dichloromethane) were pooled and evaporated to give pure 22 (4 g).

4.5 Preparation of O-trimethyl acetyl phenyl derivative 23

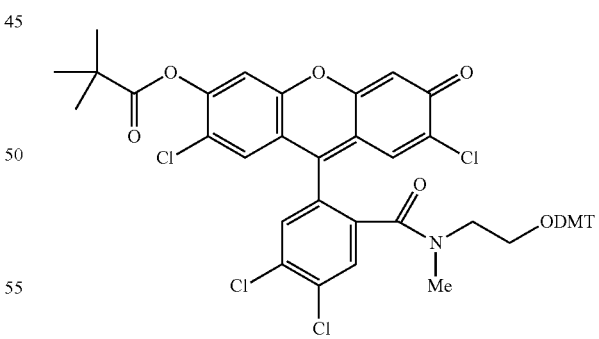

22 (4 g) was dissolved in dry pyridine (300 mL) under argon. Trimethyl acetyl chloride (5 mL) was then added dropwise via syringe over 3 min. The solution changed from bright orange to a dull yellow color during the addition. TLC (same conditions as above) showed a change to a yellow spot rf=0.8. A mass spectrum of an aliquot showed a peak at M/e 920, consistent with acylation of the phenolic type hydroxyl group. The mixture was purified with the same methods as the starting material to give 23 (2.4 g).

4.6 Removal of the DMT Group to Form 24

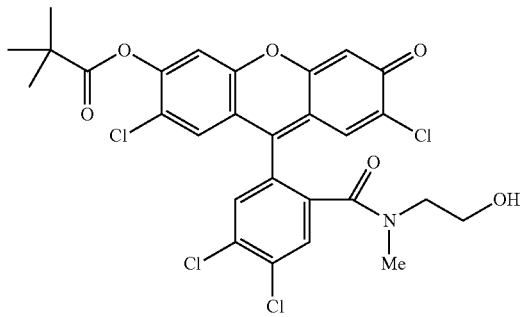 [SMILES: CN(CCO)C(=O)c1cc(Cl)c(Cl)cc1-c1c2cc(Cl)c(=O)cc-2oc2cc(OC(=O)C(C)(C)C)c(Cl)cc12]

Compound 23 (2 g) was treated with a solution (300 mL) of 3% dichloroacetic acid in dichloromethane for 1 h. The acid was then neutralized by cautiously adding saturated NaHCO$_3$, (300 mL) with stirring for an additional 1 h. The layers were separated and the dichloromethane layer was washed with water (200 mL) followed by brine (200 mL). The organic phase was dried over MgSO$_4$ and reduced by rotary evaporation. The product was purified by column chromatography as above to give pure 24 (0.8 g).

4.7 Preparation of Phosphoramidite 25

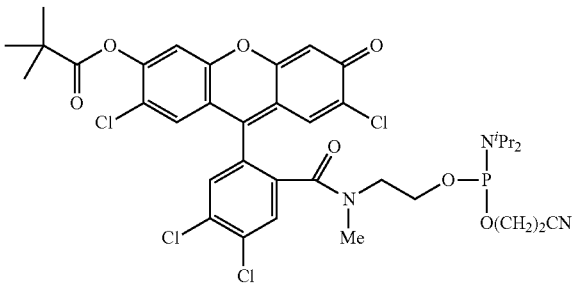

Compound 24 was dried by rotary evaporation from dry pyridine (50 mL) and high vacuum overnight and reacted with a pre-mixed solution of N,N,N',N'-tetra-isopropyl-2-cyanoethyl phosphoramidate (500 mg) and tetrazole (20 mg) in dry acetonitrile (50 mL). After 1 h, a mass spectrum of an aliquot showed a peak corresponding to conversion to a new compound, M/e 822, consistent with the formation of the phosphoramidite. The solution was reduced by rotary evaporation and re-dissolved ethyl acetate (200 mL). The organic phase was washed with saturated NaHCO$_3$ (100 mL) and dried over MgSO$_4$. Filtration followed by evaporation and high vacuum overnight gave phosphoramidite 25 (1 g).

Example 5

5.1 Preparation of Rhodamine 6G N-methylaminoethanol-linker-nucleoside 26

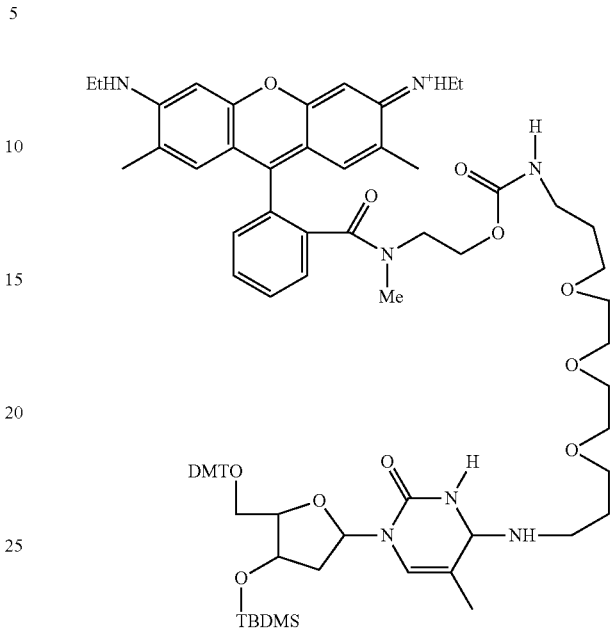

Rhodamine 6G N-methylaminoethanol 13 (10 g) was dried by rotary evaporation from dry pyridine (200 mL) and high vacuum for 24 h. The resulting material was dissolved in dry pyridine (200 mL) and then dry dioxane (75 mL) was added. p-Nitrophenyl chloroformate (12 g) was added dropwise as a solution in dioxane (100 mL) over 20 min. The solution was stirred for several hours whereupon a mass spectrum of an aliquot revealed complete conversion to the p-nitrophenylcarbonate ester. The solvents were removed by rotary evaporation and the residue was dissolved in dichloromethane (400 mL). The organic phase was washed with of 0.5 N KH$_2$PO$_4$ (2×300 mL) and was then dried over MgSO$_4$. The solution was reduced to an oil by rotary evaporation and re-dissolved in THF (150 mL). N$^4$-(2-(4,7,10-trioxa-1,13-tridecanediamine)-5-methyl-5'-(4,4'-dimethoxytrityl)-3'-O-tert-butyldimethylsilyl-2'deoxycytidine (Lyttle, et. al., *Bioconjugate Chem.* 13: 1146-1154 (2002)) (15 g) was dissolved in THF (300 mL) and saturated NaHCO$_3$ (200 mL) was added. With magnetic stirring, the THF solution of p-nitrophenylcarbonate ester was added slowly over 5 min. The solution was stirred for 18 h. A mass spectrum of an aliquot showed a peak at M/e 1363, consistent with that of the desired product. Most of the THF was removed and the residue was extracted with dichloromethane (300 mL). The organic phase was washed with water (2×200 mL) and dried over MgSO$_4$. The solution was reduced by rotary evaporation and applied to a basic alumina column, 7% by weight water (20×50 cm), packed with 2% methanol, 2% pyridine in dichloromethane. The column was eluted with 2 L of this solvent, then a gradient to 10% methanol was run over 20 L of solvent. Fractions were checked by TLC (20% methanol, 2% pyridine in dichlo-

5.2 Deprotection of the 3'-hydroxyl moiety, forming 27

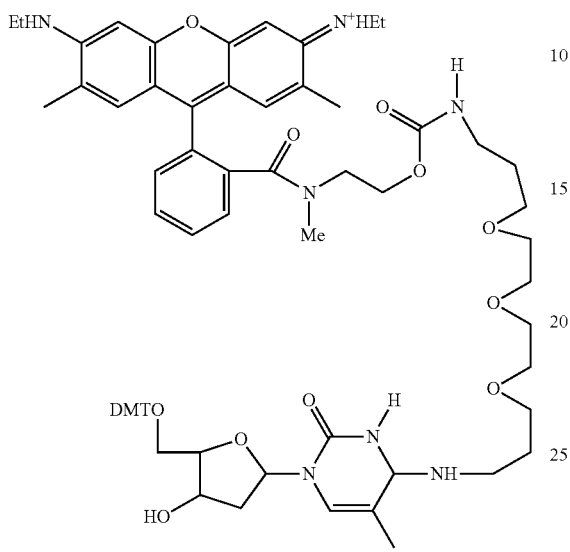

Compound 26 (6 g) was dissolved in a solution of THF (100 mL), 1 N tetrabutylammonium fluoride (12 mL) in THF (Aldrich #216143) and acetic acid (2 mL). The solution was allowed to stand overnight and an aliquot, checked by mass spectrum, showed a peak at M/e 1252, consistent with removal of the TBDMS group. The reaction mixture was quenched by adding NaHCO$_3$ (20 mL). THF was removed by rotary evaporation. The residue was dissolved in dichloromethane (300 mL). The organic phase was washed with water (200 mL) followed by NaHCO$_3$ (200 mL). The dichloromethane layer was dried over MgSO$_4$ and reduced to an oil by rotary evaporation. TLC (20% methanol, 2% pyridine in dichloromethane) revealed adequate product purity to proceed without purification. The material was dried by rotary evaporation with dry pyridine (100 mL) followed by high vacuum for 18 h to give 27 (2.5 g).

5.3 Preparation of 3'-glycolic acid ester 28

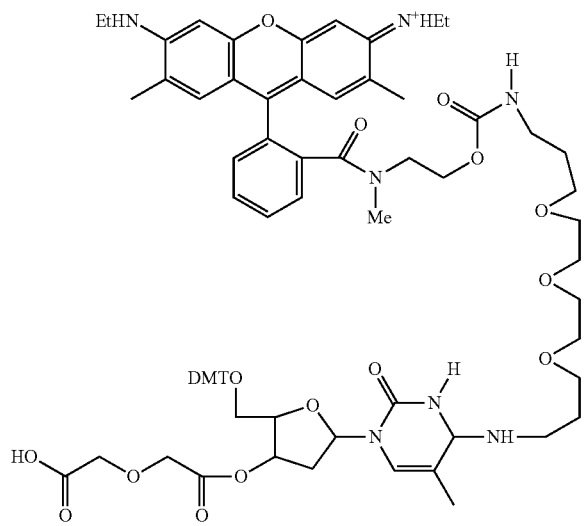

Compound 27 (2.5 g) was dissolved in dry pyridine (100 mL) and N-methylimidazole (0.5 mL) and diglycolic anhydride (2.5 g) were added. The mixture was allowed to stand 48 h, whereupon a mass spectrum of an aliquot showed a peak at M/e 1367, consistent with esterification of the hydroxyl group of 27. The solvent was removed by rotary evaporation, and the residue was dissolved in dichloromethane (300 mL). The organic phase was washed with 0.5 M KH$_2$PO$_4$ (3×200 mL) and dried over MgSO$_4$. The solution was filtered and reduced by rotary evaporation to give 28 (1.5 g) as a foam.

5.4 Conjugation of 28 to CPG, Forming Functionalized CPG 29

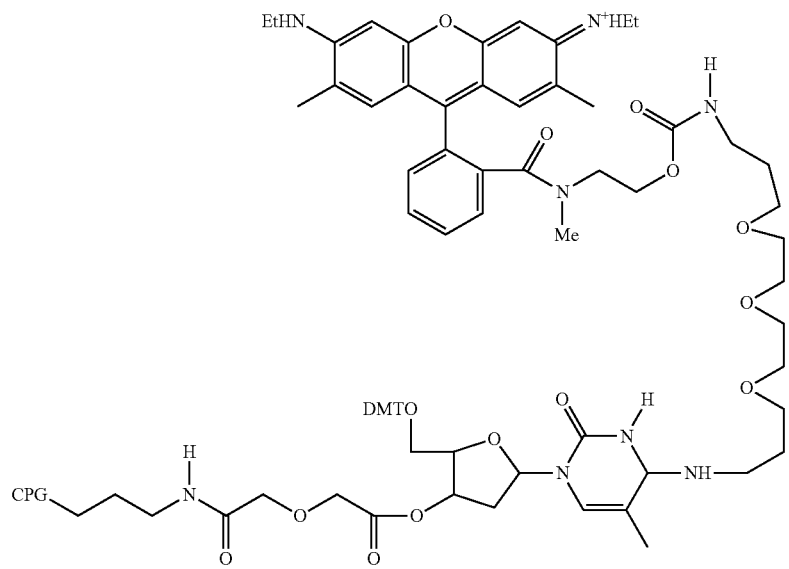

Controlled pore glass (CPG) for solid phase oligonucleotide synthesis was made by activating 28 (300 mg) with BOP (250 mg) and N-methyl morpholine (50 µL) in acetonitrile (50 mL), and then adding 500 Å aminopropyl CPG (Biosearch) (5 g). The slurry was allowed to stand overnight and the support was then rinsed thoroughly with acetonitrile. Unreacted aminopropyl groups were then capped with a mixture of N-methylimidazole (5 mL) and acetic anhydride (5 mL) in acetonitrile (50 mL). After 15 min the solution was rinsed out of the support and the dark orange CPG was washed thoroughly with acetonitrile, followed by dichloromethane and then was dried by high vacuum overnight. The final loading, according to mild acid removal of the DMT groups, was 25 micromoles per gram.

Example 6

6.1 Synthesis of Rhodamine B 4-hydroxypiperidinyl N,N,diisopropyl betacyanoethyl phosphoramidite

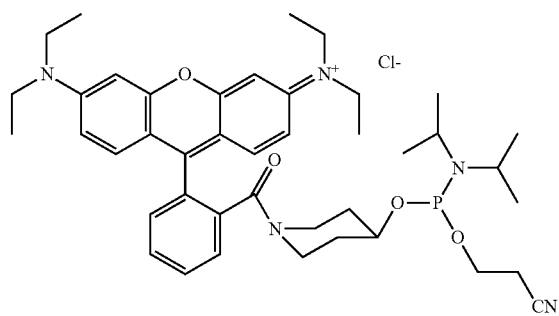 [SMILES: CCN(CC)c1ccc2c(-c3ccccc3C(=O)N3CCC(OP(OCCC#N)N(C(C)C)C(C)C)CC3)c3ccc(=[N+](CC)CC)cc-3oc2c1 ; [Cl-]]

Rhodamine B (37 g), was dissolved in DMF (400 mL) and N-methylmorpholine (20 mL) was added. BOP (45 g) was added as a solid, and the solution was magnetically stirred for 10 min. A solution of 4-hydroxypiperidine (20 g) in DMF (200 mL) was added to the dye solution dropwise over 20 min. After an additional 30 min, a mass spectrum of an aliquot showed complete reaction (to the 4-hydroxy-piperidinyl alcohol, M/e 531). The DMF was removed by rotary evaporation, and the residue was dissolved in 10% MeOH in DCM (600 mL). The organic solution was washed with 1 N HCl (800 mL) and evaporated to a tar. Column chromatography on alumina with a gradient of 2-4% MeOH in DCM gave the product (29 g), rf 0.5 (silica plate, 10% MeOH/DCM 2% pyridine). One half of the product was dried by pyridine strip and under vacuum overnight. A solution of N,N,N,N-tetraisopropyl betacyanoethyl phosphane (6.6 g) and tetrazole (500 mg) in acetonitrile (200 mL) was added to a solution of the product in DCM (200 mL). After 2 h, a mass spectrum of an aliquot showed complete reaction (to the amidite, M/e 730). The organics were removed by rotary evaporation, and dissolved in DCM (500 mL). The organic phase was washed with sat'd NaHCO$_3$ (300 mL) of evaporated to a tar. The product was purified by chromatography on alumina with a gradient of 2-4% MeOH in DCM, 1% pyridine 1% water. Fractions were pooled and evaporated to give amidite (14.6 g), rf 0.7 (silica plate, 10% MeOH/DCM 2% pyridine).

6.2 Synthesis of Rhodamine 101 4-hydroxypiperidinyl N,N,diisopropyl betacyanoethyl phosphoramidite

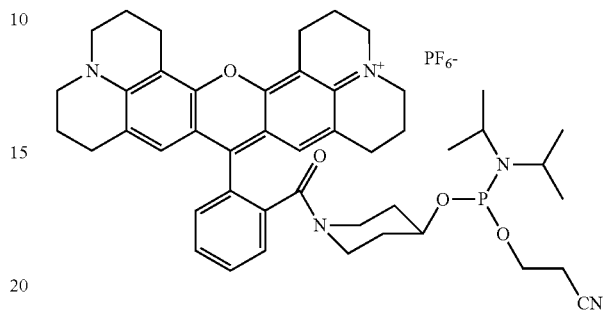

Rhodamine 101 (55 g) was dissolved in DMF (800 mL) and of N-methylmorpholine (25 mL) was added. BOP (50 g) was added as a solid, and the solution was magnetically stirred for 10 min. A solution of 4-hydroxypiperidine (30 g) in DMF (200 mL) was prepared and this was added to the dye solution dropwise over 20 min. After and additional 60 min. a mass spectrum of an aliquot showed complete reaction (to the 4-hydroxypiperidinyl alcohol, M/e 577). The DMF was removed by rotary evaporation, and the residue was dissolved in 10% MeOH in DCM (900 mL). The organic solution was washed with 1 N HCl (800 mL) and evaporated to a tar. Column chromatography on silica with a gradient of 2-6% MeOH in DCM, 2% pyridine, gave the intermediate alcohol (40.9 g), rf 0.5 (silica plate, 20% MeOH/DCM 2% pyridine). One half of this product was dried by pyridine strip and vacuum overnight. A solution of N,N,N,N-tetraisopropyl betacyanoethyl phosphane (10 g) and tetrazole (600 mg) was mixed in acetonitrile (300 mL) and added to a solution of the alcohol above dissolved in DCM (300 mL). After 4 h, a mass spectrum of an aliquot showed complete reaction (to the amidite, M/e 777). The solution was stripped by rotary evaporation, and re-dissolved in DCM (700 mL). The organic phase was washed with sat'd NaHCO$_3$ (500 mL) and evaporated to a tar. The product was purified by chromatography on alumina with a gradient of 2-4% MeOH in DCM, 2% pyridine 1% water. Fractions were pooled and evaporated to give amidite (17.3 g), rf 0.8 (silica plate, 20% MeOH/DCM 2% pyridine).

Example 7

7.1 Synthesis of Nucleic Acids 5' Labeled with 15, 19 and 25

DNA Fragments 3'-TTTTTTTTTT-5' and 3'-TTC-GATAAGTCTAG-5' were made at a 200 nm scale on 3'-glycolate CPGs (van der Laan, et. al, *Tetrahedron Lett.* 38: 2252 (1997)) with cyanoethyl phosphoramidite monomers on a Biosearch 8750™ DNA synthesizer. Protecting groups on the exocyclic amine groups of A, C and G were benzoyl, acetyl and dimethylformamidine, respectively. After the synthesis was complete, the 5' DMT group was removed (with 3% dichloroacetic acid in dichloromethane) and the synthesis column with the CPG containing the DNA was washed with dry acetonitrile.

To couple the dye moiety to the nucleic acid, 35-50 mg of 15, 19 and 25 dye phosphoramidites were dissolved in dry acetonitrile (150 μL) in a 20 mL scintillation vial, and activated molecular sieves (20 mg) were added. The resulting solution was applied to the column with a 1 mL syringe. A companion syringe containing 100 μL of 0.4 M S-ethylthiotetrazole in acetonitrile was attached at the other end of the column. The solutions were mixed over the CPG with the syringes, and allowed to stand for 5 min. The columns were put back on the DNA synthesizer and washed with acetonitrile followed by oxidizer solution (0.02 M iodine in a mixture of THF (70%):pyridine (20%):water (10%). After 30 seconds, this solution was washed with acetonitrile and the contents of each column were expelled into 1.5 mL screw-cap Eppendorf™ tubes. A mixture of 2-methoxyethylamine (Aldrich) (100 μL) and methanol (300 μL) were introduced into each tube, and the tubes were capped and allowed to stand for 6 h at room temperature. The methanol containing the labeled DNA was removed, and the CPG was washed with fresh methanol (400 μL). The CPG was discarded and the methanol containing the labeled DNA fragments was evaporated.

7.2 Synthesis of Nucleic Acids 5' Labeled with 6

DNA Fragments 3'-TTTTT-5', 3'-TTTTTTTTTT-5', DNA Fragments 3'-TTTTTTTTTTTTTTT-5', labeled with 6 were prepared as described above, except that the fragments were cleaved from the CPG support using a solution of t-butylamine (25%):methanol (25%):water (50%).

7.3 Synthesis of Nucleic Acids 3' Labeled with 28

For 3'-dye labeled DNA synthesis CPG 27 was used in lieu of the standard DNA synthesis support. After automated DNA synthesis was finished, the sample was deprotected and cleaved with the amine/alcohol solution and evaporated after 6 h. The samples were dissolved in de-ionized water (1 mL) for analysis.

7.4 HPLC and Mass Spectral Analysis of 3' and 5'-Dye Labeled DNA

Anion exchange HPLC analyses were performed as follows: 2-20 μL of the aqueous samples, depending on the concentration, were injected onto a Dionex anion exchange column (4.6×250 mm); samples were eluted at 2 mL/min with aqueous buffers of (A) 0.025 M TRIS HCl and 0.01 M TRIS, and (B) 0.025 M TRIS HCl, 0.01 M TRIS, and 1.0 M NaBr using a linear gradient of 1:0 to 0:1 over 14 min, with UV detection at 260 nm. Reverse phase HPLC as follows: 20 μL of the aqueous sample were injected onto a HAISIL HL C18, 5μ column (4.6×150 mm); samples were eluted at 1 mL/min with buffers of (A) 0.1M TEAA, 5% acetonitrile, (B) acetonitrile, with a linear gradient of 1:0 to 0:1 over 15 min: UV detection at 260 nm. Samples for mass spectral analysis were prepared as per Bruker Corp.

7.5 Results

Table 2 shows calculated and found masses of the above Dye-DNA 15 mers by MALDI mass spectroscopy:

TABLE 2

| Compound | Calculated M/e | Found |
|---|---|---|
| 5'-25 15 mer | 5160.2 | 5129 |
| 5'-15 15 mer | 5249.2 | 5214 |

TABLE 2-continued

| Compound | Calculated M/e | Found |
|---|---|---|
| 5'-19 15 mer | 5324.2 | 5304 |
| 3'-28 15 mer | 5273.2 | 5241 |

Example 8

8.1 Evaluation of Dual Labeled Nucleic Acid Probes

The dual labeled probes were evaluated for the efficacy in a real-time PCR procedure. The real-time PCR procedure is performed on a real-time quantitative PCR device such as the ABI Prizm 7700 Sequence Detection System™ (Applied Biosystems, Foster City, Calif.), or the iCycler (BioRad, Hercules, Calif.). These two systems amplify samples in a 96-well format on a thermocycler. During amplification, light-induced fluorescent signal is collected in real-time for all 96 wells, and detected. The systems include software for running the instruments and for analyzing the data.

The ABI 7700 Sequence Detection System was calibrated with xanthene dye 15 and other fluorescent dyes.

Quantitation was obtained using primers and a dual-labeled probe derived from sequence encoding the ApoB (apolipoprotein B) gene and from the TelomeraseRT (Telomerase reverse transcriptase) gene. BHQ1 and BHQ2 quenchers, described in copending U.S. patent application Ser. No. 09/567,863, were incorporated into the primers (see, for example, Walton et al., *Bioconjugate Chemistry* 13: 1155-1158 (2002)). The xanthenes 15, 19 and 25 were utilized to incorporate a fluorophore at the 5'-terminus. Gene-specific primers and fluorogenic probes were designed based upon the coding sequences of the DNAs. The sequences for the primers and probes (forward primer, reverse primer and probe) used for the ApoB and Telomerase are as follows:

| TelomeraseRT.f1 | CAGGTGGAGACCCTGAGAA |
|---|---|
| TelomeraseRT.r1 | ACACCTTTGGTCACTCCAAAT |
| TelomeraseRT.p1 | TCCCAGAGCTCCCAGGGTCC |
| ApoB.f1 | TGAAGGTGGAGGACATTCCTCTA |
| ApoB.r1 | CTGGAATTGCGATTTCTGGTAA |
| ApoB.p1 | CGAGAATCACCCTGCCAGACTTCCGT |

The ApoB probe sequence and the Telomerase probe sequence were synthesized with various combinations of fluorescent dyes and quencher. These probes were used along with their gene specific primers in real-time PCR assays. Human DNA (Clontech, Palo Alto, Calif.) was detected at concentrations of 100 ng per reaction or 1 ng per reaction in an assay. Data were analyzed from triplicate reactions, and the average and standard deviation for each triplicate was calculated.

Real-time quantitative PCR (Livak et al., *PCR Methods Appl.* 4(6): 357-62 (1995)) was used to determine whether the compounds above compared favorably to existing dyes used as reporters in such an assay. Positive results in this assay can be interpreted to extend to positive results in other assays, including but not limited to, the Invader (Hall et al., *Natl. Acad. Sci. USA* 97: 8272-8277 (2000)), the Amplifuor (Uehara, *Biotechniques* 26(3): 552-8 (1999)), the Scorpion (Thelwell et al., *Nucl. Acids. Res.* 28: 3752-3761 (2000)), and the Molecular Beacon (Tyagi & Kramer, *Nature Biotechnol.* 14: 303-308 (1996)).

The real-time PCR assay reaction is a fluorescent PCR-based technique that makes use of the 5' exonuclease activity of Taq DNA polymerase enzyme to monitor amplification in real time. Two oligonucleotide primers are used to generate a PCR product typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a fluorescence quencher, traditionally TAMRA or DABCYL. Any light emission from the reporter dye is quenched by the quenching dye when the two dyes are located close together as they are on the intact probe. During the amplification reaction, the Taq DNA polymerase enzyme cleaves the probe in a template-dependent manner. The resultant probe fragments disassociate in solution, and signal from the released reporter dye is free from the quenching effect of the quencher moiety. One molecule of reporter dye is liberated for each new molecule synthesized, and detection of the unquenched reporter dye provides the basis for quantitative interpretation of the data.

The real-time PCR assay data are initially expressed as Ct, or the threshold cycle. This is defined as the cycle at which the reporter signal accumulates above the background level of fluorescence. One unit corresponds 1 PCR cycle or approximately a 2-fold amplification relative to normal, two units corresponds to 4-fold, 3 units to 8-fold amplification, and so on. The Ct values are used as quantitative measurement of the relative number of starting copies of a particular target sequence in a nucleic acid sample.

The compounds of the invention are useful replacements for dyes that are commonly used in nucleic acid assays. For example, compounds such as 15 are a useful replacement for the fluorescent dyes JOE and HEX. The dyes ROX and Texas Red can be replaced with compounds such as 19. Compounds such as 3, 6 and 8 can be substituted for TAMRA.

Excitation and emission wavelengths of the dyes of the invention and the art-recognized dyes are listed in Table 3. Because the Ct value for the dyes of the invention is equivalent to, or lower than, the Ct value of the art-recognized dyes, the present dyes are useful replacements for the art recognized dyes.

TABLE 3

| Dye | Excitation Maximum/nm | Emission Maximum/nm |
|---|---|---|
| FAM | 495 | 520 |
| JOE | 520 | 548 |
| HEX | 535 | 556 |
| VIC | 538 | 554 |
| TAMRA | 555 | 576 |
| ROX | 575 | 602 |
| 25 | 522 | 544 |
| 15 | 540 | 561 |
| 3, 6, 8 | 565 | 588 |
| 19 | 593 | 613 |

Figure 14:
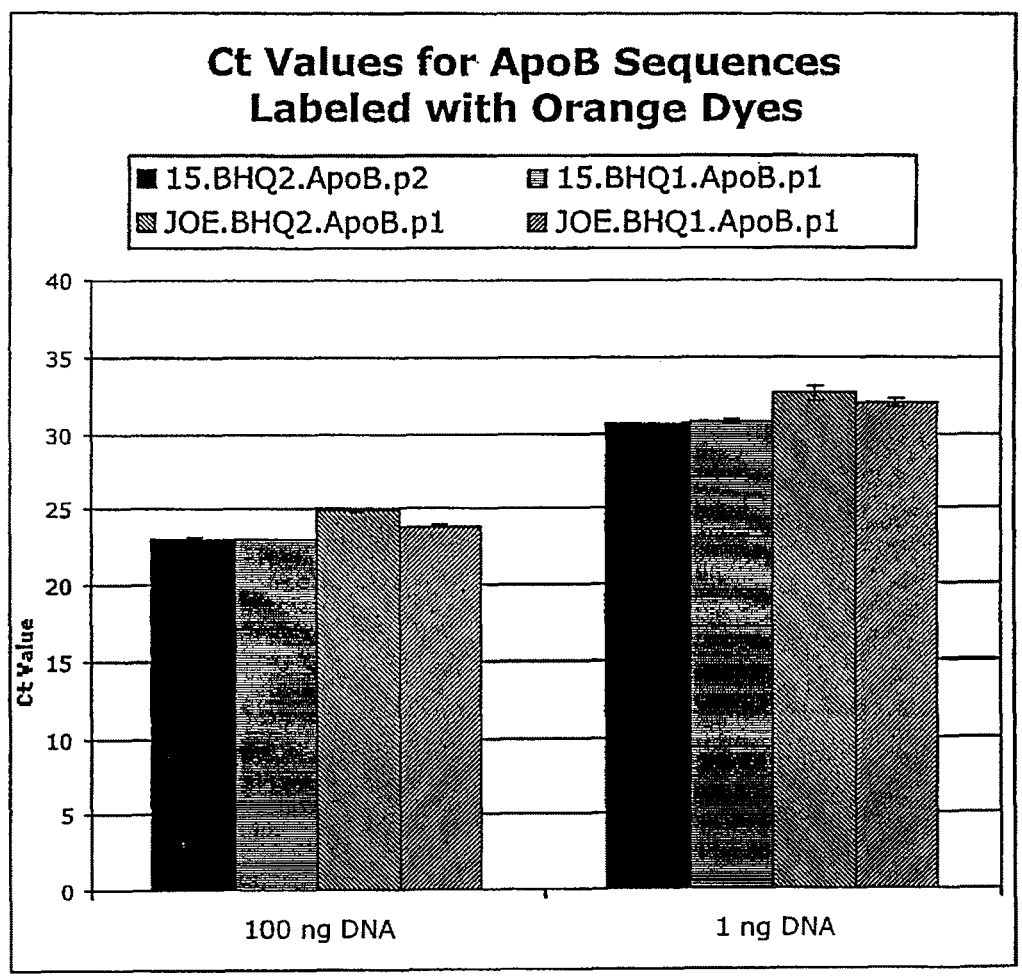
FIG. 14 is a comparison of the performance of probes labeled with dye 15 to probes labeled with JOE. The graph shows the results of the real-time PCR analysis performed on the ABI 7700 Sequence Detection System. Data for dye 15 and JOE labeled ApoB probes are presented in Ct values. The results for the dye 15 labeled probes show that it is at least equivalent to the JOE labeled probes.
Figure 15:
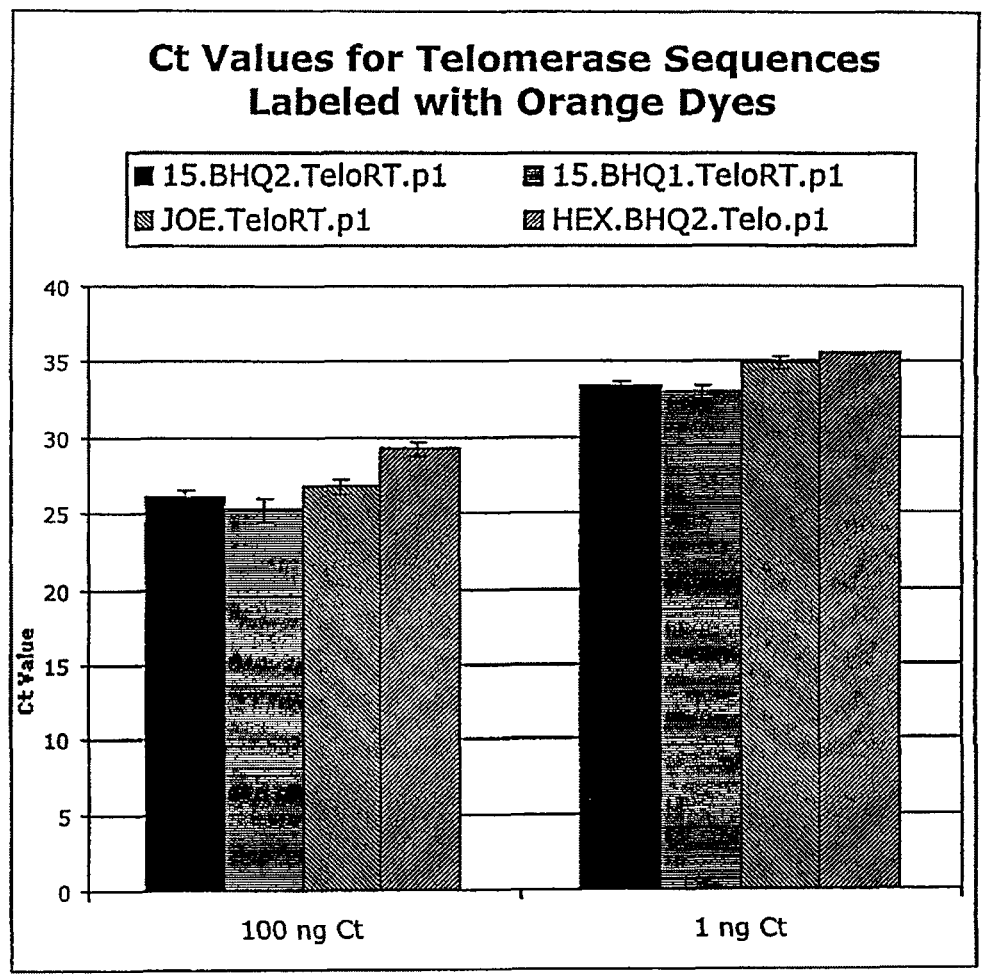
FIG. 15 is a comparison of the performance of probes labeled with dye 15 to probes labeled with HEX and JOE. The graph shows the results of the real-time PCR analysis performed on the ABI 7700 Sequence Detection System. Data for dye 15, HEX and JOE labeled telomerase probes are presented in Ct values. The results for dye 15 labeled probe show that it is at least equivalent to the HEX or JOE labeled probes.
Figure 16:
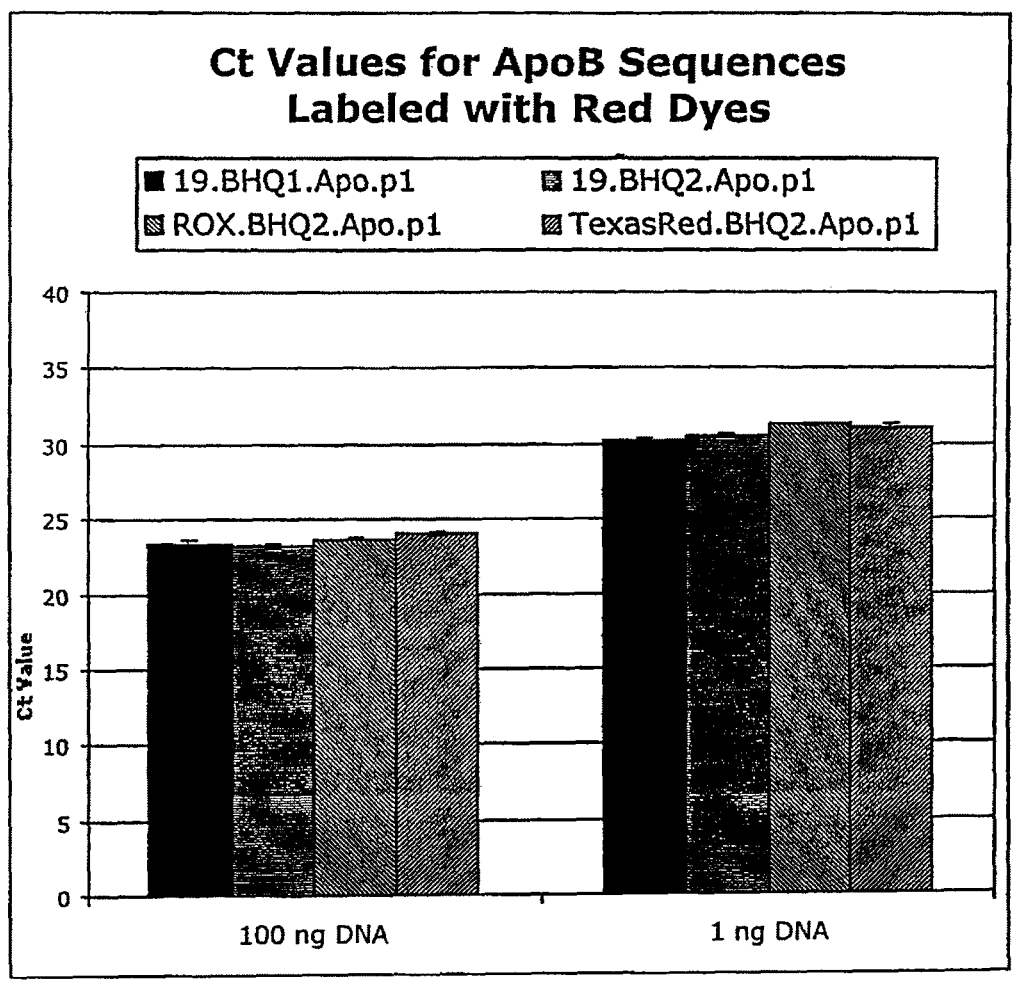
FIG. 16 is a comparison of the performance of probes labeled with dye 19 to probes labeled with ROX and Texas Red. The graph shows the results of the real-time PCR analysis performed on the ABI 7700 Sequence Detection System. Data for dye 19, ROX and Texas Red labeled ApoB probes are presented in Ct values. The results for the dye 19 labeled probe show that it is at least equivalent to the ROX or Texas Red labeled probes.

The results from three typical experiments were graphed and the data are presented in FIG. 14, FIG. 15 and FIG. 16.

The present invention provides xanthenes that are functionalized with an oxygen-containing reactive functional group that can be used to facilitate the conjugation of the xanthenes to a conjugation partner. The resulting fluorescent conjugate is of use in essentially any assay in which detection of a fluorescent species has a role. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

What is claimed is:
1. A xanthene dye having a formula which is
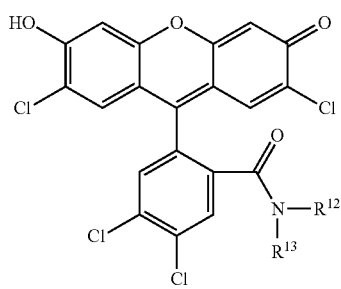
wherein C(O)NR$^{12}$R_ is a member selected from the group consisting of:
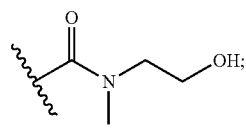
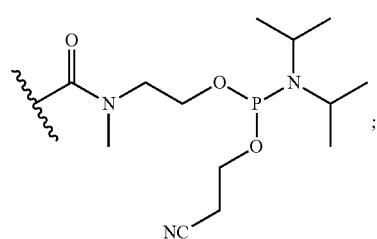
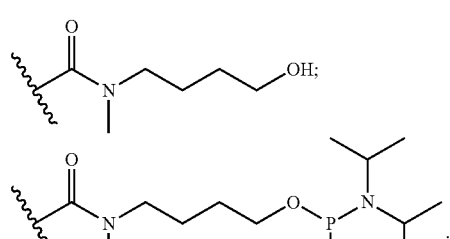
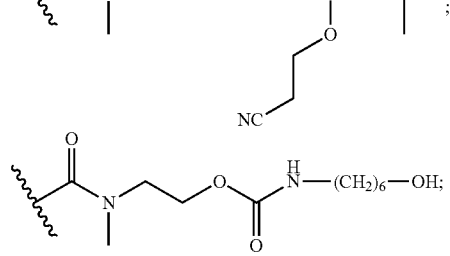
-continued
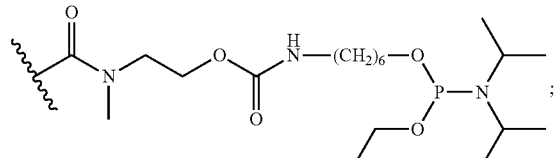
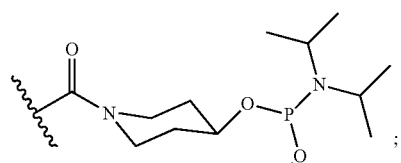
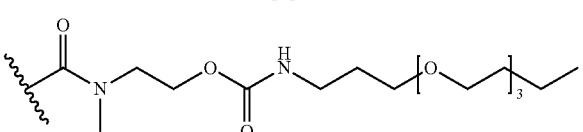
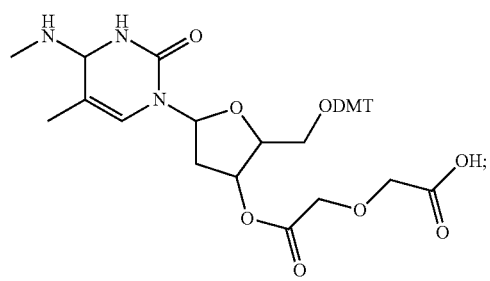
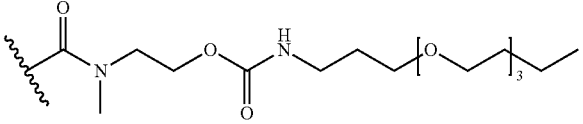
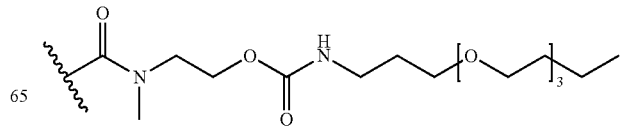
and -continued

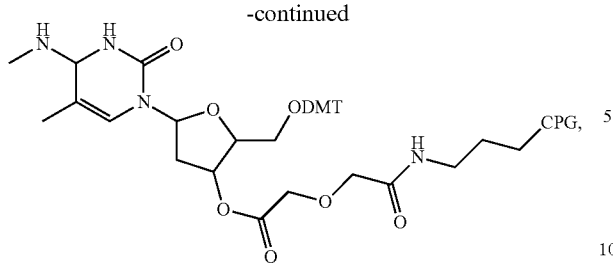

wherein said DMT is dimethoxytrityl and said CPG is controlled pore glass.

2. A xanthene dye having the formula:

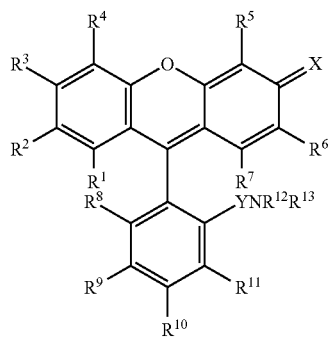

in which
$R^1, R^2, R^4, R^5, R^6, R^7, R^8, R^9, R^{10}$ and $R^{11}$ are independently selected from the group consisting of substituted or unsubstituted alkyl, substituted or unsubstituted heteroalkyl, substituted or unsubstituted aryl, substituted or unsubstituted heteroaryl, substituted or unsubstituted heterocycloalkyl, halogen, H, $NO_2$, CN, $NR^{15}R^{16}$ and $Z^2R^{16}$;
$R^3$ is $NR^{15}R^{16}$
wherein
$Z^2$ is O or S;
$R^{15}$ is a member selected from the group consisting of H, substituted or unsubstituted alkyl, and substituted or unsubstituted heteroalkyl;
$R^{16}$ is selected from the group consisting of H, substituted or unsubstituted alkyl, substituted or unsubstituted heteroalkyl, $C(Z^3)R^{17}$, and a nitrogen-containing reactive group comprising $R^{15}$ and $R^{16}$, together with the nitrogen to which they are attached, wherein said reactive group is a member selected from the group consisting of —$NHNH_2$, —N=C=S and —N=C=O
wherein
$Z^3$ is a member selected from the group consisting of O, S and NH;
$R^{17}$ is a member selected from the group consisting of substituted or unsubstituted alkyl, substituted or unsubstituted heteroalkyl, $OR^{18}$, and $NR^{19}R^{20}$
wherein
$R^{19}$ and $R^{20}$ are members independently selected from the group consisting of H, substituted or unsubstituted alkyl and substituted or unsubstituted heteroalkyl;
$R^{18}$ is a member selected from the group consisting of H, substituted or unsubstituted alkyl, substituted or unsubstituted heteroalkyl, substituted or unsubstituted aryl, substituted or unsubstituted heteroaryl and $C(O)R^{21}$ wherein
$R^{21}$ is substituted or unsubstituted alkyl or substituted or unsubstituted heteroalkyl;
Y is C(O) or $S(O)_2$;
X is $(NR^{22}R^{23})$ or (O)
wherein
$R^{22}$ and $R^{23}$ are members independently selected from the group consisting of H, substituted or unsubstituted alkyl and substituted or unsubstituted heteroalkyl;
$R^{12}$ and $R^{13}$, together with the nitrogen atom to which they are attached, joined to form a ring, wherein said ring formed from $R^{12}$ and $R^{13}$ is substituted with:
  a member selected from the group consisting of hydroxyl, ester, sulfonate, ether, aldehyde, phosphoramidite, carboxylic acid, acid halides, acyl imidazoles, and thioesters, or
  a substituted or unsubstituted alkyl comprising a member selected from the group consisting of hydroxyl, ester, sulfonate, ether, aldehyde, phosphoramidite, carboxylic acid, acid halides, acyl imidazoles, and thioesters, or
  a substituted or unsubstituted heteroalkyl moiety comprising a member selected from the group consisting of hydroxyl, ester, sulfonate, ether, aldehyde, phosphoramidite, carboxylic acid, acid halides, acyl imidazoles, and thioesters.

3. The xanthene dye of claim 1, wherein $NR^{12}R^{13}$ has the formula:

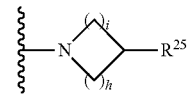

wherein
h and i are members independently selected from integers such that the sum (h+i) is from 4-8; and
$R^{25}$ is:
  a member selected from the group consisting of hydroxyl, ester, sulfonate, ether, aldehyde, phosphoramidite, carboxylic acid, acid halides, acyl imidazoles, and thioesters, or
  a substituted or unsubstituted alkyl comprising a member selected from the group consisting of hydroxyl, ester, sulfonate, ether, aldehyde, phosphoramidite, carboxylic acid, acid halides, acyl imidazoles, and thioesters, or
  a substituted or unsubstituted heteroalkyl moiety comprising a member selected from the group consisting of hydroxyl, ester, sulfonate, ether, aldehyde, phosphoramidite, carboxylic acid, acid halides, acyl imidazoles, and thioesters.

4. The xanthene dye of claim 3, wherein $R^{25}$ is a phosphoramidite, or a substituted or unsubstituted alkyl comprising a phosphoramidite, or a substituted or unsubstituted heteroalkyl moiety comprising a phosphoramidite.

5. The xanthene dye of claim 3, wherein $R^{25}$ is a phosphoramidite.

6. The xanthene dye of claim 3, wherein h is 2 and i is 2.

7. A xanthene dye having the formula which is a member selected from the group consisting of:

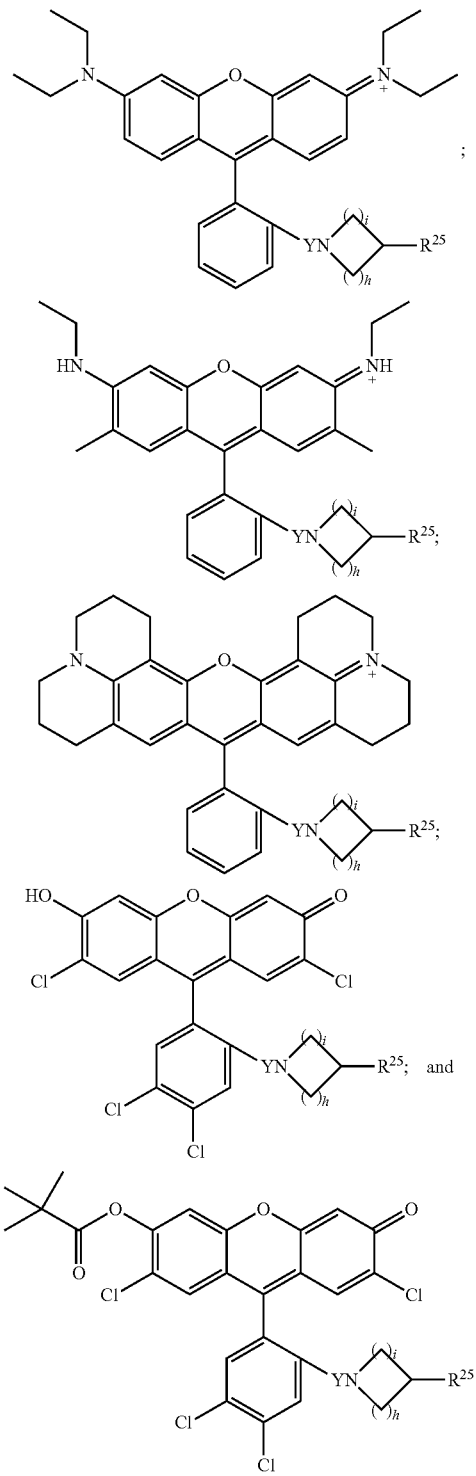

wherein
Y is C(O) or S(O)$_2$;
h and i are members independently selected from integers such that the sum (h+i) is from 4-8; and R$^{25}$ is
- a member selected from the group consisting of hydroxyl, ester, sulfonate, ether, aldehyde, phosphoramidite, carboxylic acid, acid halides, acyl imidazoles, and thioesters, or
- a substituted or unsubstituted alkyl comprising a member selected from the group consisting of hydroxyl, ester, sulfonate, ether, aldehyde, phosphoramidite, carboxylic acid, acid halides, acyl imidazoles, and thioesters, or
- a substituted or unsubstituted heteroalkyl moiety comprising a member selected from the group consisting of hydroxyl, ester, sulfonate, ether, aldehyde, phosphoramidite, carboxylic acid, acid halides, acyl imidazoles, and thioesters.

8. The xanthene dye of claim 7, wherein h is 2 and i is 2.

9. The xanthene dye of claim 7, wherein R$^{25}$ is a phosphoramidite, or a substituted or unsubstituted alkyl comprising a phosphoramidite, or a substituted or unsubstituted heteroalkyl moiety comprising a phosphoramidite.

10. The xanthene dye of claim 7, wherein R$^{25}$ is a phosphoramidite.

11. The xanthene dye of claim 7, having a formula which is:

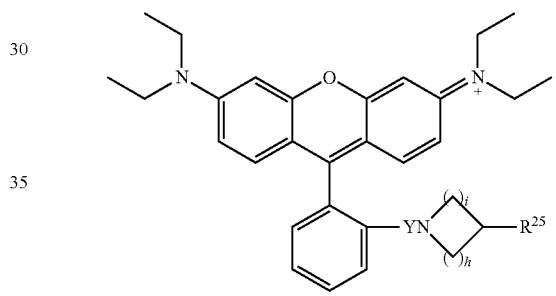

wherein
h is 2 and i is 2; and R$^{25}$ is a phosphoramidite, or a substituted or unsubstituted alkyl comprising a phosphoramidite, or a substituted or unsubstituted heteroalkyl moiety comprising a phosphoramidite.

12. The xanthene dye of claim 7, having a formula which is:

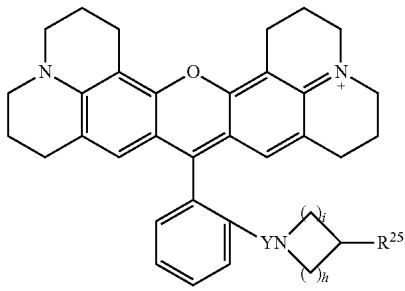

wherein
h is 2 and i is 2; and R$^{25}$ is a phosphoramidite, or a substituted or unsubstituted alkyl comprising a phosphoramidite, or a substituted or unsubstituted heteroalkyl moiety comprising a phosphoramidite.

13. The xanthene dye of claim 7, having a formula which is:

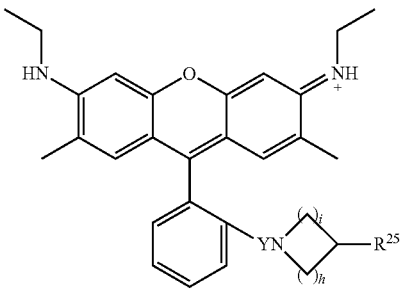

wherein
h is 2 and i is 2; and $R^{25}$ is a phosphoramidite, or a substituted or unsubstituted alkyl comprising a phosphoramidite, or a substituted or unsubstituted heteroalkyl moiety comprising a phosphoramidite.

14. A xanthene dye having the formula:

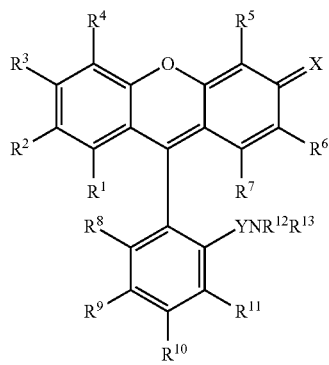

in which
$R^1$, $R^2$, $R^4$, $R^5$, $R^6$, $R^7$, $R^8$, $R^9$, $R^{10}$ and $R^{11}$ are independently selected from the group consisting of substituted or unsubstituted alkyl, substituted or unsubstituted. heteroalkyl, substituted or unsubstituted aryl, substituted or unsubstituted. heteroaryl, substituted or unsubstituted heterocycloalkyl, halogen, H, $NO_2$, CN, $NR^{15}R^{16}$ and $Z^2R^{16}$;
$R^3$ is $Z^2R^{16}$ or $NR^{15}R^{16}$
wherein
$Z^2$ is O or S;
$R^{15}$ is a member selected from the group consisting of H. substituted or unsubstituted alkyl, and substituted or unsubstituted heteroalkyl;
$R^{16}$ is selected from the group consisting of H, substituted or unsubstituted alkyl, substituted or unsubstituted heteroalkyl, $C(Z^3)R^{17}$, and a nitrogen-containing reactive group comprising $R^{15}$ and $R^{16}$, together with the nitrogen to which they are attached, wherein said reactive group is a member selected from —$NHNH_2$, —N=C=S and —N=C=O
wherein
$Z^3$ is a member selected from the group consisting of O, S and NH;
$R^{17}$ is a member selected from the group consisting of substituted or unsubstituted alkyl, substituted or unsubstituted heteroalkyl, $OR^{18}$, and $NR^{19}R^{20}$ wherein
$R^{18}$ is a member selected from the group consisting of H, substituted or unsubstituted alkyl, substituted or unsubstituted heteroalkyl, substituted or unsubstituted aryl, substituted or unsubstituted heteroaryl and $C(O)R^{21}$
wherein
$R^{21}$ is substituted or unsubstituted. alkyl or substituted or unsubstituted heteroalkyl;
$R^{19}$ and $R^{20}$ are members independently selected from the group consisting of H, substituted or unsubstituted alkyl and substituted or unsubstituted heteroalkyl
Y is C(O) or $S(O)_2$;
X is $(NR^{22}R^{23})$ or (O)
wherein
$R^{22}$ and $R^{23}$ are members independently selected from the group consisting of H, substituted or unsubstituted alkyl and substituted or unsubstituted heteroalkyl;
$R^{12}$ and $R^{13}$, together with the nitrogen atom to which they are attached, are joined to form a ring, wherein said ring formed from $R^{12}$ and $R^{13}$ is substituted with a member selected from the group consisting of hydroxyl, ester, sulfonate, ether, aldehyde, phosphoramidite, carboxylic acid, acid halides, acyl imidazoles, and thioesters, or a substituted or unsubstituted alkyl bearing a member selected from the group consisting of hydroxyl, ester, sulfonate, ether, aldehyde, phosphoramidite, carboxylic acid, acid halides, acyl imidazoles, and thioesters, or substituted or unsubstituted heteroalkyl moiety bearing a member selected from the group consisting of hydroxyl, ester, sulfonate, ether, aldehyde, phosphoramidite, carboxylic acid, acid halides, acyl imidazoles, and thioesters.

15. The xanthene dye of claim 14, wherein $NR^{12}R^{13}$ as the formula:

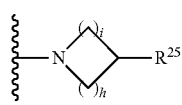

wherein
h and i are members independently selected from integers such that the sum (h+i) is from 4-8; and
$R^{25}$ is a member selected from the group consisting of hydroxyl, ester, sulfonate, ether, aldehyde, phosphoramidite, carboxylic acid, acid halides, acyl imidazoles, and thioesters, or a substituted or unsubstituted alkyl bearing a member selected from the group consisting of hydroxyl, ester, sulfonate, ether, aldehyde, phosphoramidite, carboxylic acid, acid halides, acyl imidazoles, and thioesters, or substituted or unsubstituted heteroalkyl moiety bearing a member selected from the group consisting of hydroxyl, ester, sulfonate, ether, aldehyde, phosphoramidite, carboxylic acid, acid halides, acyl imidazoles, and thioesters.

16. The xanthene dye of claim 15, wherein $R^{25}$ is a phosphoramidite, or a substituted or unsubstituted alkyl bearing a phosphoramidite, or a substituted or unsubstituted heteroalkyl moiety bearing a phosphoramidite.

17. The xanthene dye of claim 15, wherein $R^{25}$ is a phosphoramidite.

18. The xanthene dye of claim 15, wherein h is 2 and i is 2.

19. The xanthene dye of claim 15, wherein the xanthene dye has the formula which is a member selected from the group consisting of:

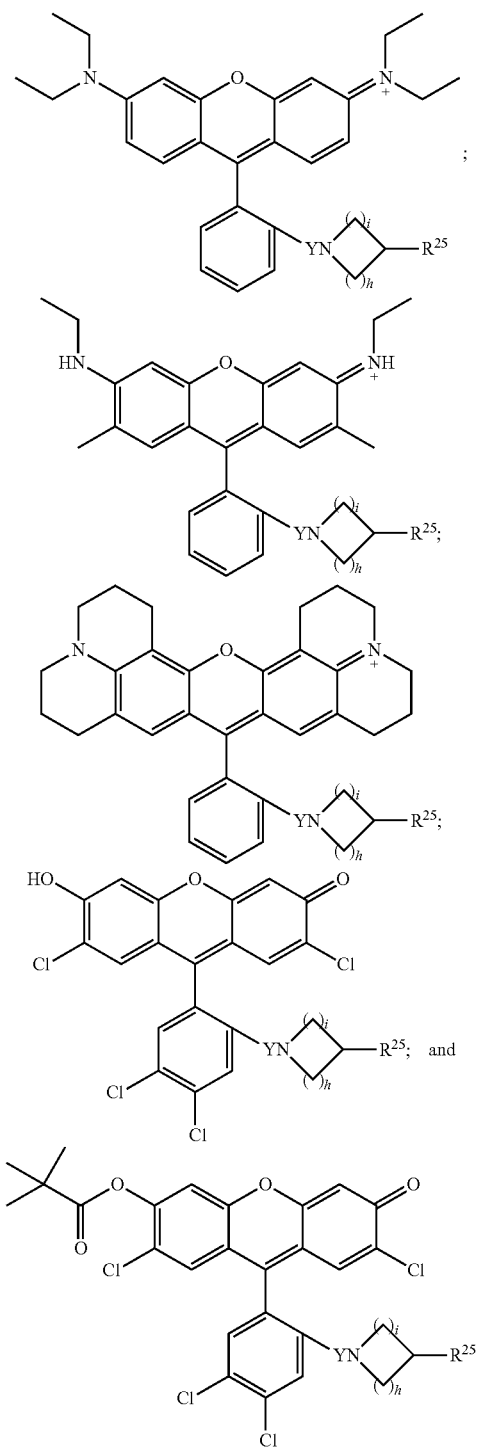

wherein
h and i are members independently selected from integers such that the sum (h+i) is from 4-8; and
$R^{25}$ is a member selected from the group consisting of hydroxyl, ester, sulfonate, ether, aldehyde, phosphoramidite, carboxylic acid, acid halides, acyl imidazoles, and thioesters, or a substituted or unsubstituted alkyl bearing a member selected from the group consisting of hydroxyl, ester, sulfonate, ether, aldehyde, phosphoramidite, carboxylic acid, acid halides, acyl imidazoles, and thioesters, or substituted or unsubstituted heteroalkyl moiety bearing a member selected from the group consisting of hydroxyl, ester, sulfonate, ether, aldehyde, phosphoramidite, carboxylic acid, acid halides, acyl imidazoles, in thioesters.

20. The xanthene dye of claim 19, wherein h is 2 and i is 2.

21. The xanthene dye of claim 19, wherein $R^{25}$ is a phosphoramidite, or a substituted or unsubstituted alkyl comprising a phosphoramidite, or a substituted or unsubstituted heteroalkyl moiety comprising a phosphoramidite.

22. The xanthene dye of claim 19, wherein $R^{25}$ is a phosphoramidite.

23. The xanthene dye of claim 19, having a formula which is:

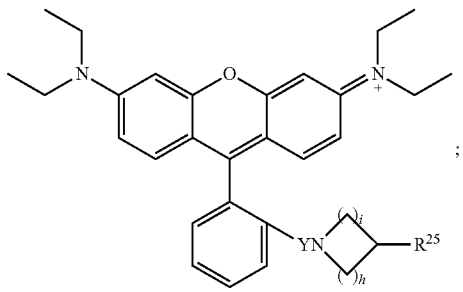

wherein
h is 2 and i is 2; and $R^{25}$ is a phosphoramidite, or a substituted or unsubstituted alkyl comprising a phosphoramidite, or a substituted or unsubstituted heteroalkyl moiety comprising a phosphoramidite.

24. The xanthene dye of claim 19, having a formula which is:

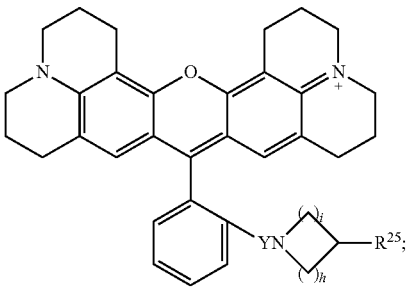

wherein
h is 2 and i is 2; and $R^{25}$ is a phosphoramidite, or a substituted or unsubstituted alkyl comprising a phosphoramidite, or a substituted or unsubstituted heteroalkyl moiety comprising a phosphoramidite.

25. The xanthene dye of claim 19, having a formula which is:

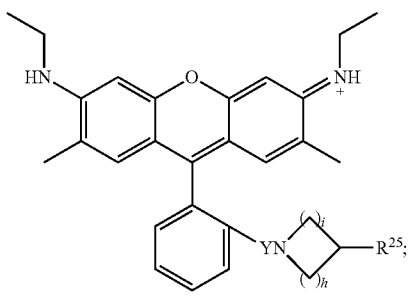

wherein h is 2 and i is 2; and $R^{25}$ is a phosphoramidite, or a substituted or unsubstituted alkyl comprising a phosphoramidite, or a substituted or unsubstituted heteroalkyl moiety comprising a phosphoramidite.

26. The xanthene dye of claim 2, wherein said ester is N-hydroxysuccinimide ester, N-hydroxybenztriazole ester, p-nitrophenyl ester, alkyl ester, alkenyl ester, alkynyl ester, or aromatic ester.

27. The xanthene dye of claim 14, wherein said ester is N-hydroxysuccinimide ester, N-hydroxybenztriazole ester, p-nitrophenyl ester, alkyl ester, alkenyl ester, alkynyl ester, or aromatic ester.

28. The xanthene dye of claim 19, wherein said ester is N-hydroxysuccinimide ester, N-hydroxybenztriazole ester, p-nitrophenyl ester, alkyl ester, alkenyl ester, alkynyl ester, or aromatic ester.

29. A xanthene dye having a formula which is:

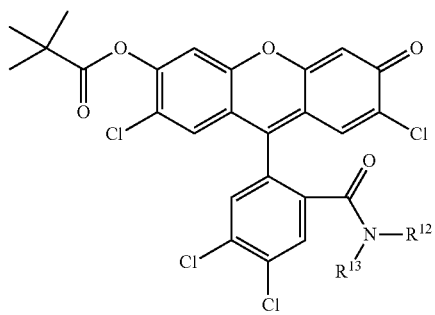

wherein $C(O)NR^{12}R^{13}$ is a member selected from the group consisting of:

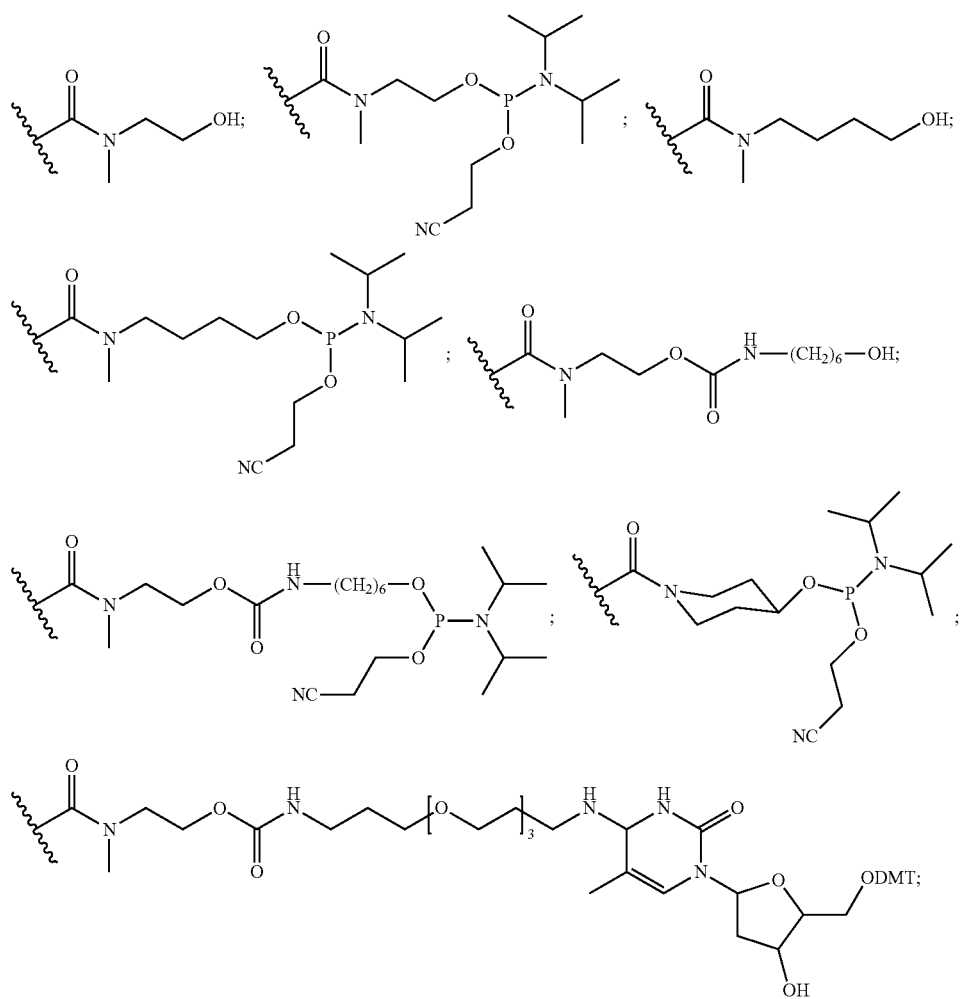

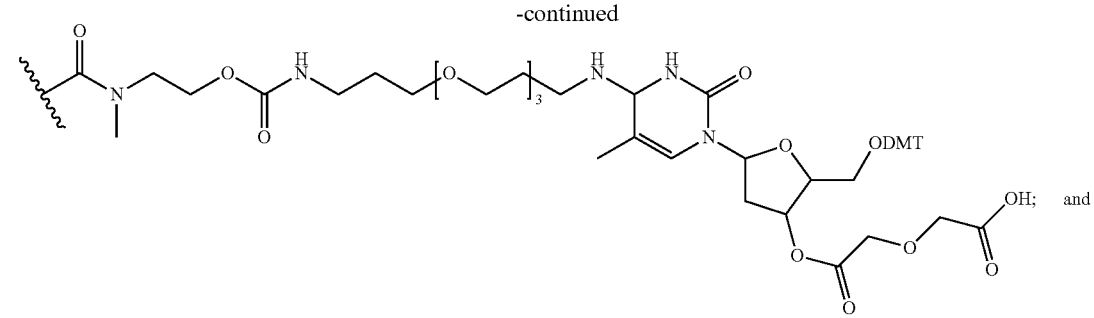
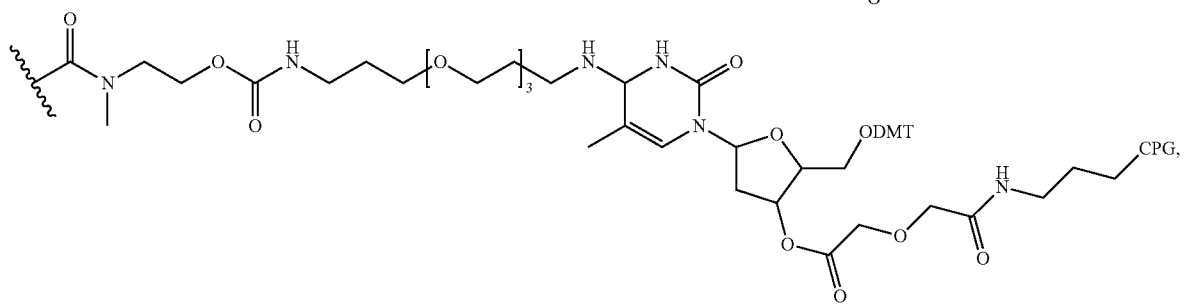
wherein said DMT is dimethoxytrityl and said CPG is controlled pore glass.
30. A xanthene dye having a formula which is:
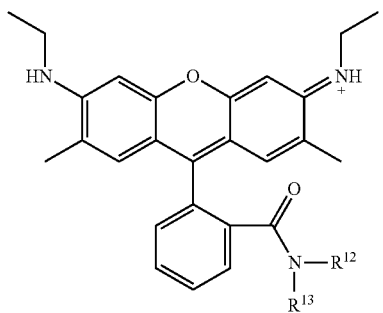
wherein $C(O)NR^{12}R^{13}$ is a member selected from the group consisting of:
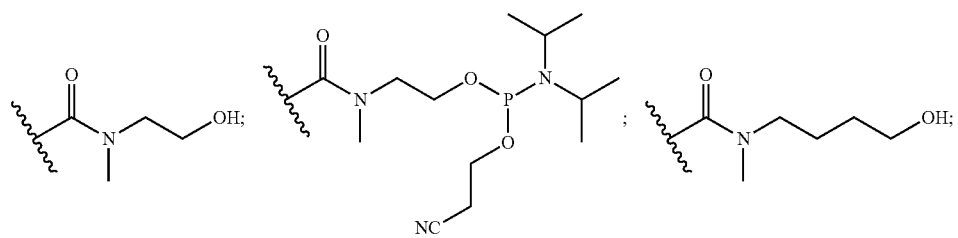
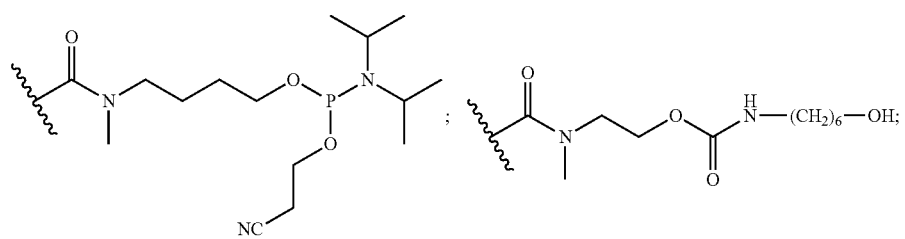

95 96
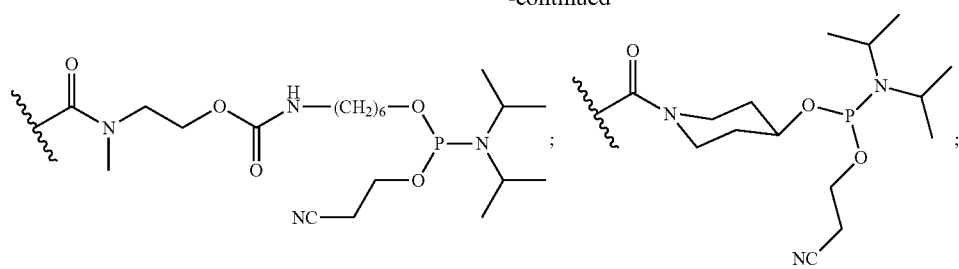
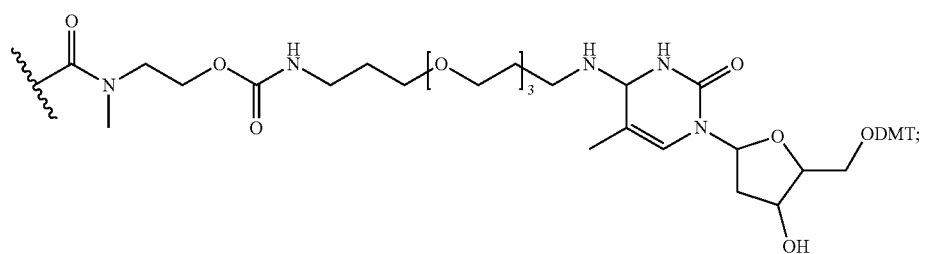
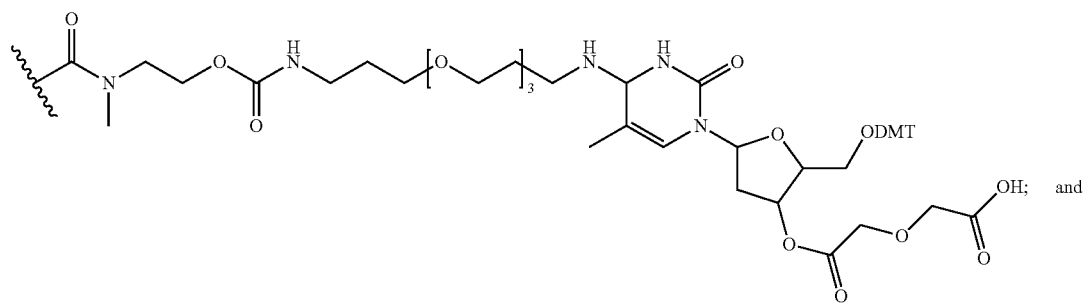
and
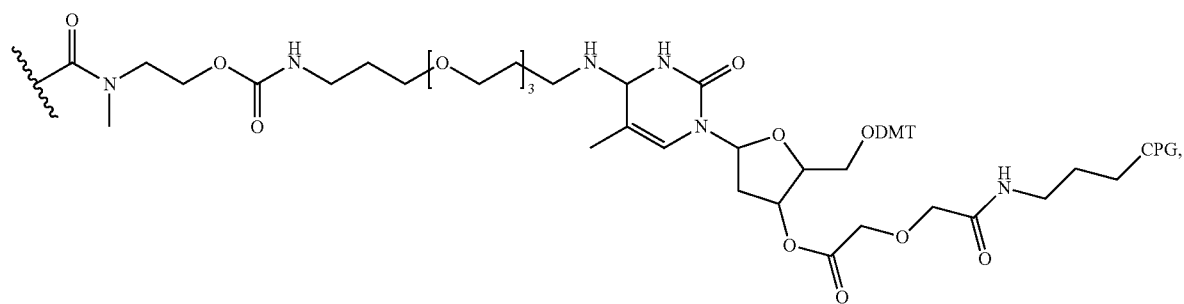

wherein said DMT is dimethoxytrityl and said CPG is controlled pore glass.
31. A xanthene dye having a formula which is:
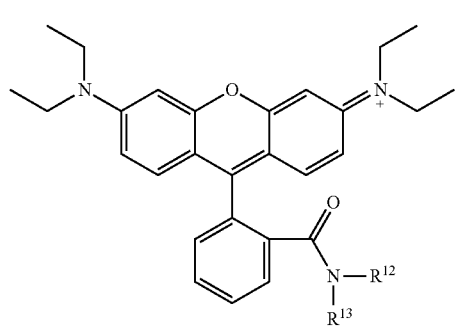
wherein C(O)NR¹²R¹³ is a member selected from the group consisting of:
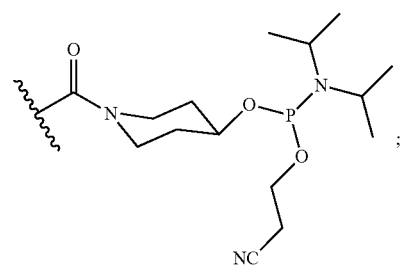
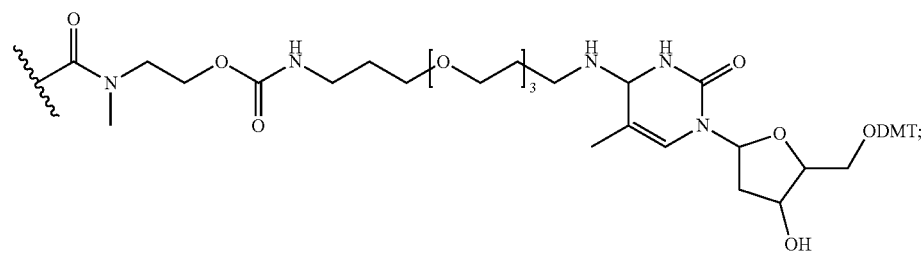
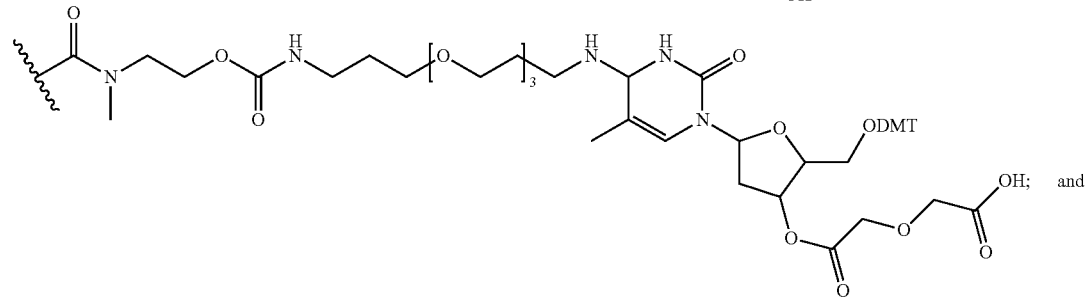 and
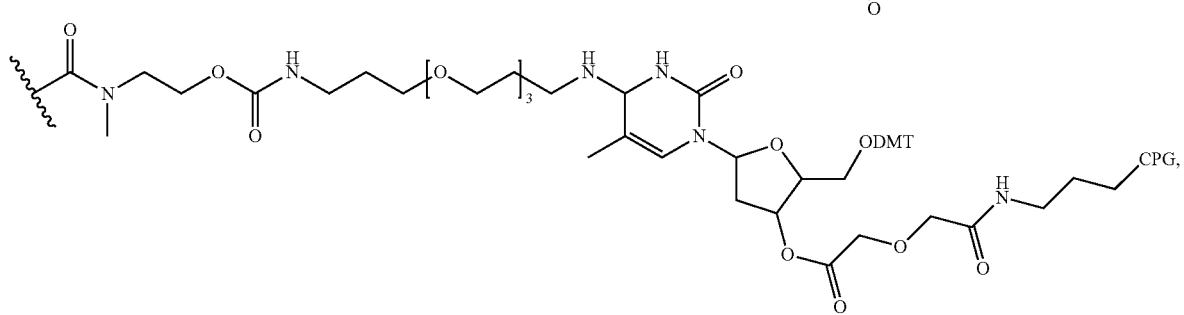

wherein said DMT is dimethoxytrityl and said CPG is controlled pore glass.
32. A xanthene dye having a formula which is:
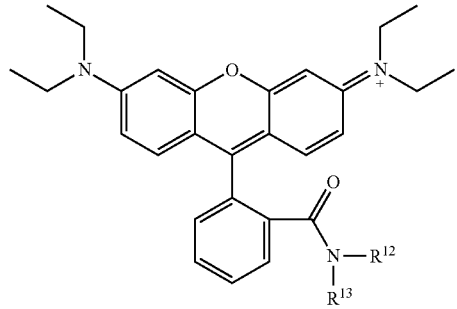
wherein C(O)NR$^{12}$R$^{13}$ is
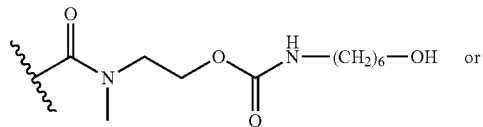
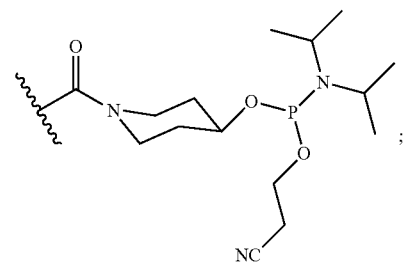
33. A xanthene dye having a formula which is:
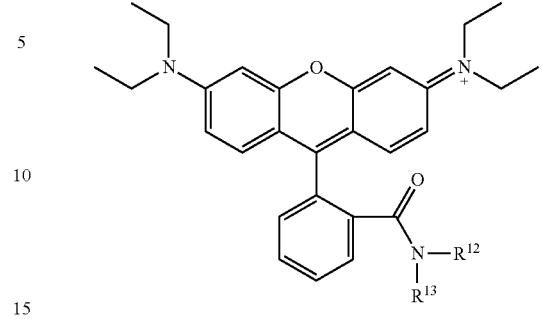
wherein C(O)NR$^{12}$R$^{13}$ is
34. A xanthene dye having a formula which is:
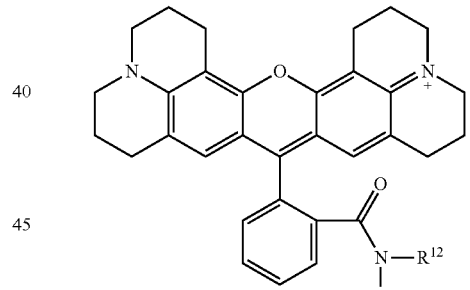
wherein C(O)NR$^{12}$R$^{13}$ is a member selected from the group consisting of:
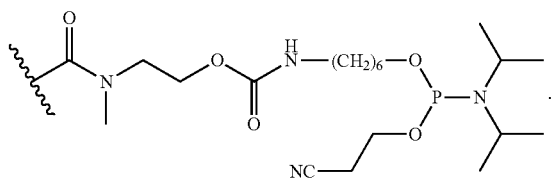

-continued
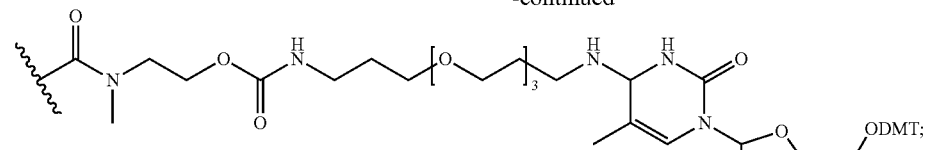
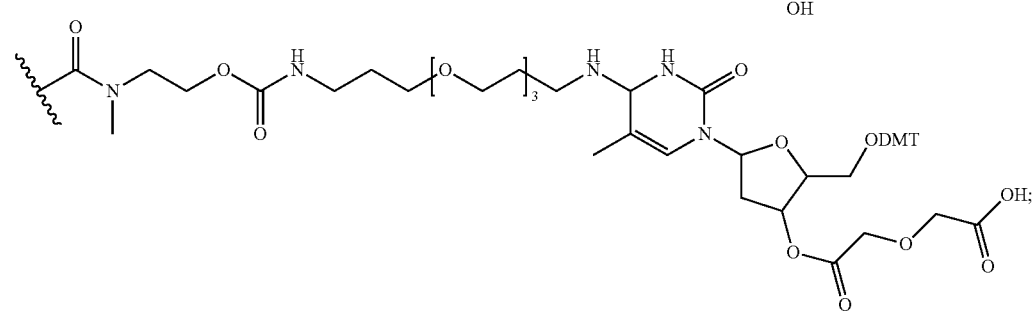
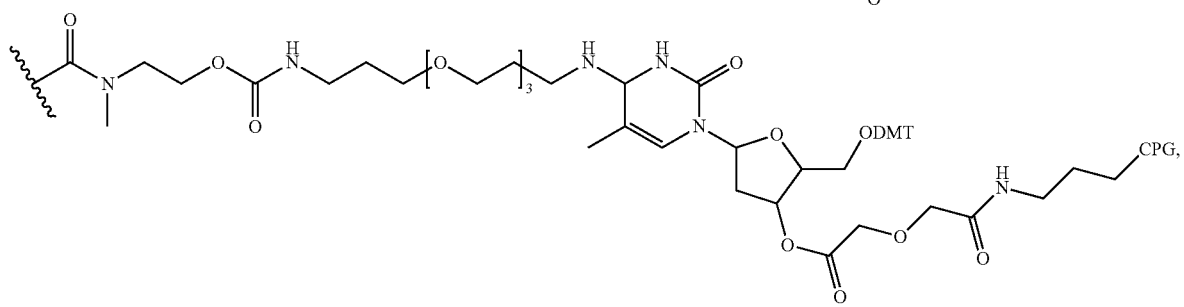
wherein said DMT is dimethoxytrityl and said CPG is controlled pore glass.
35. A xanthene dye having a formula which is:
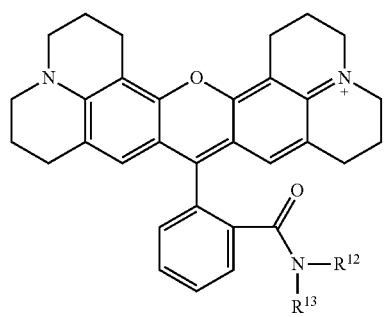
wherein C(O)NR$^{12}$R$^{13}$ is
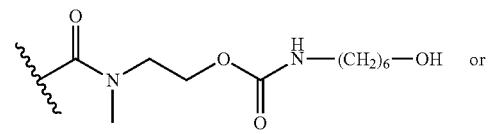 or
-continued
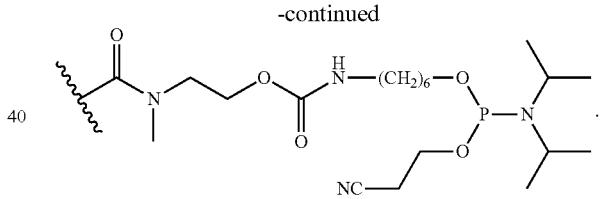
36. A xanthene dye having a formula which is:
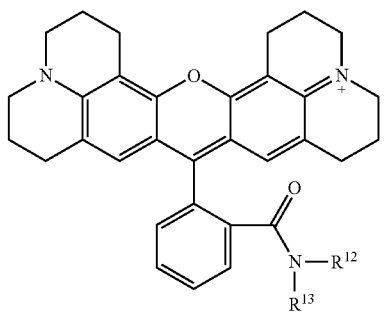

wherein C(O)NR$^{12}$R$^{13}$ is
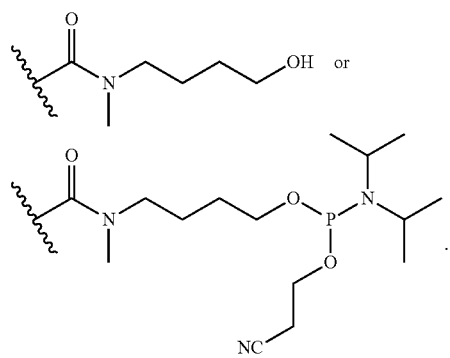 or
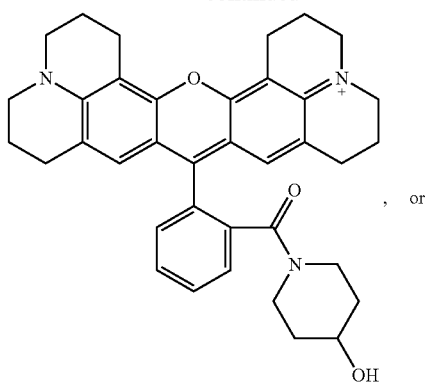, or
37. The xanthene dye of claim 7, having the formula:
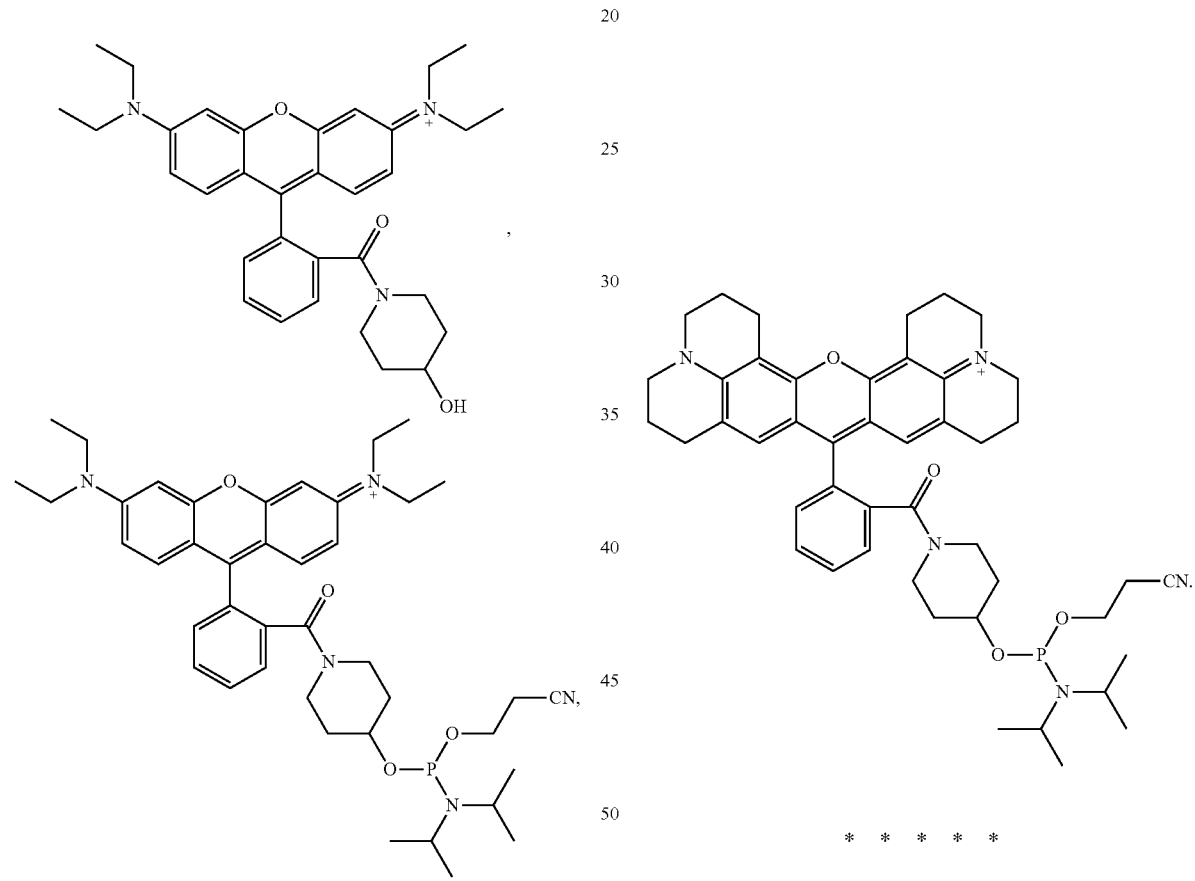
* * * * *